(12) United States Patent
Suga et al.

(10) Patent No.: US 11,946,042 B2
(45) Date of Patent: Apr. 2, 2024

(54) MODIFICATION OF D- AND T-ARMS OF tRNA ENHANCING D-AMINO ACID AND β-AMINO ACID UPTAKE

(71) Applicant: The University of Tokyo, Tokyo (JP)

(72) Inventors: Hiroaki Suga, Tokyo (JP); Takayuki Katoh, Tokyo (JP)

(73) Assignee: The University of Tokyo, Tokyo (JP)

( * ) Notice: Subject to any disclaimer, the term of this patent is extended or adjusted under 35 U.S.C. 154(b) by 867 days.

(21) Appl. No.: 16/755,942

(22) PCT Filed: Aug. 28, 2018

(86) PCT No.: PCT/JP2018/031814
§ 371 (c)(1),
(2) Date: Jun. 22, 2020

(87) PCT Pub. No.: WO2019/077887
PCT Pub. Date: Apr. 25, 2019

(65) Prior Publication Data
US 2020/0308572 A1    Oct. 1, 2020

(30) Foreign Application Priority Data

Oct. 16, 2017   (JP) ................................ 2017-200356

(51) Int. Cl.
*C12N 15/10*     (2006.01)
*C12N 15/113*    (2010.01)
*C40B 40/10*     (2006.01)

(52) U.S. Cl.
CPC ........ *C12N 15/1062* (2013.01); *C12N 15/113* (2013.01); *C40B 40/10* (2013.01)

(58) Field of Classification Search
None
See application file for complete search history.

(56) References Cited

U.S. PATENT DOCUMENTS

| 9,410,148 | B2 * | 8/2016  | Suga  | ........................ | C40B 40/10 |
| 2007/0083951 | A1 * | 4/2007 | Huang | ............... | C12N 15/8217 |
| | | | | | 435/468 |
| 2011/0275119 | A1 | 11/2011 | Suga | | |
| 2012/0208720 | A1 | 8/2012 | Kashiwagi | | |
| 2013/0316910 | A1 | 11/2013 | Suga | | |
| 2014/0018257 | A1 | 7/2014 | Suga | | |

FOREIGN PATENT DOCUMENTS

| EP | 2088202     |   | 8/2009  |
| EP | 2647720     |   | 10/2013 |
| EP | 2647721     |   | 10/2013 |
| EP | 2995683     |   | 3/2016  |
| JP | 2008125396  | A | 6/2008  |
| WO | 2011049157  | A1 | 4/2011 |
| WO | 2012074129  | A1 | 6/2012 |
| WO | 2012074130  | A | 6/2012  |
| WO | 2014194129  |   | 12/2014 |

OTHER PUBLICATIONS

Achenbach et al., "Outwitting EF-Tu and the ribosome: translation with D-amino acids", Jul. 13, 2015, pp. 5687-5698, vol. 43, No. 12, Publisher: Nucleic Acids Research.

Czekster et al., "In Vivo Biosynthesis of a-Amino Acid-Containing Protein", Apr. 18, 2016, pp. 5194-5497, vol. 138, No. 16, Publisher: J. Am. Chem. Soc.

Dedkova et al., "Construction of modified ribosomes for incorporation of D-amino acids into proteins", Dec. 26, 2006, pp. 15541-15551, vol. 45, No. 51, Publisher: Biochemistry.

Dedkova et al., "-Puromycin Selection of Modified Ribosomes for in Vitro Incorporation of -Amino Acids", Dec. 6, 2011, pp. 401-415, vol. 51, No. 1, Publisher: Biochemistry.

Dedkova et al., "Enhanced d-Amino Acid Incorporation into Protein by Modified Ribosomes", May 10, 2030, pp. 6616-6617, vol. 125, No. 22, Publisher: J. Am. Chem. Soc.

Fujino et al., "Reevaluation of the d-Amino Acid Compatibility with the Elongation Event in Translation", Jan. 9, 2013, pp. 1830-1837, vol. 135, No. 5, Publisher: J. Am. Chem. Soc.

Fujino et al., "Ribosomal Synthesis of Peptides with Multiple-Amino Acids", Jan. 25, 2016, pp. 1962-1969, vol. 138, No. 6, Publisher: J. Am. Chem. Soc.

Goto et al., "Flexizymes for genetic code reprogramming", May 12, 2011, pp. 779-790, vol. 6, Publisher: Nat Protoc.

Goto et al., "Initiating translation with D-amino acids", Jul. 2008, pp. 1390-1398, vol. 14, No. 7, Publisher: RNA.

Heckler et al., "Dipeptide formation with misacylated tRNAPhes", Apr. 10, 1983, pp. 4492-4495, vol. 258, No. 7, Publisher: J Biol Chem.

Iqbal et al., "Ribosomal incorporation of backbone modified amino acids via an editing-deficient aminoacyl-tRNA synthetase", Jan. 31, 2018, pp. 1073-1078, vol. 16, No. 7, Publisher: Organic & Biomolecular Chemistry.

Kato et al., "Essential structural elements in tRNA(Pro) for EF-P-mediated alleviation of translation stalling", May 24, 2016, p. 11657, vol. 7, Publisher: Nat Commun.

Katoh et al., Jan. 19, 2017, pp. 46-54, vol. 24, No. 1, Publisher: Cell Chemical Biology.

Katoh et al., "Logical engineering of D-arm and T-stem of tRNA that enhances d-amino acid incorporation", Dec. 15, 2007, pp. 12601-12610, vol. 45, No. 22, Publisher: Nucleic Acids Res.

(Continued)

*Primary Examiner* — Nancy J Leith
*Assistant Examiner* — Jessica D Parisi
(74) *Attorney, Agent, or Firm* — Suzannah K. Sundby, Esq.; Canady + Lortz LLP

(57) ABSTRACT

The purpose of the present invention is to provide, for translation in a cell-free translation system, a novel translation system capable of synthesizing a peptide having therein consecutive non-proteinogenic amino acids. The present invention provides a tRNA containing the base sequence represented by SEQ ID NO: 1 and encoding a non-proteinogenic amino acid.

15 Claims, 16 Drawing Sheets

Specification includes a Sequence Listing.

(56) References Cited

OTHER PUBLICATIONS

Kawakami et al., "Messenger RNA-programmed incorporation of multiple N-methyl-amino acids into linear and cyclic peptides", Jan. 2008, pp. 32-42, vol. 15, No. 1, Publisher: Chem Biol.

Kawakami et al., "Extensive reprogramming of the genetic code for genetically encoded synthesis of highly N-alkylated polycyclic peptidomimetics", Aug. 21, 2013, pp. 12297-12304, vol. 135, No. 33, Publisher: J Am Chem Soc.

Kojima et al., "Genetic Code Reprogramming", 2011, pp. 004-009, Publisher: Seibutsu Butsuri. Partial Translation.

Maini et al., "Incorporation of -amino acids into dihydrofolate reductase by ribosomes having modifications in the peptidyltransferase center", Mar. 1, 2013, pp. 1088-1096, vol. 21, No. 5, Publisher: Bioorganic and Medicinal Chemistry.

Maini et al., "Protein Synthesis with Ribosomes Selected for the Incorporation of -Amino Acids", Jun. 16, 2015, pp. 3694-3706, vol. 54, No. 23, Publisher: Biochemistry.

Murakami et al., "A highly flexible tRNA acylation method for non-natural polypeptide synthesis", May 2006, pp. 357-359, vol. 3, No. 5, Publisher: Nat. Methods.

Ohta et al., "Synthesis of polyester by means of genetic code reprogramming", Dec. 2007, pp. 1315-1322, vol. 14, No. 12, Publisher: Chem Biol.

Subtelny et al., "Ribosomal synthesis of N-methyl peptides", May 14, 2008, pp. 6131-6136, vol. 130, No. 19, Publisher: J Am Chem Soc.

Yamagishi et al., "Natural product-like macrocyclic N-methyl-peptide inhibitors against a ubiquitin ligase uncovered from a ribosome-expressed de novo library", Dec. 23, 2011, pp. 1562-1570, vol. 18, No. 12, Publisher: Chem Biol.

Ito et al., "Technologies for the synthesis of mRNA-encoding libraries and discovery of bioactive natural product-inspired non-traditional macrocyclic peptides", Mar. 18, 2013, pp. 3502-3528, vol. 18, No. 3, Publisher: Molecules.

\* cited by examiner

[Fig.1]
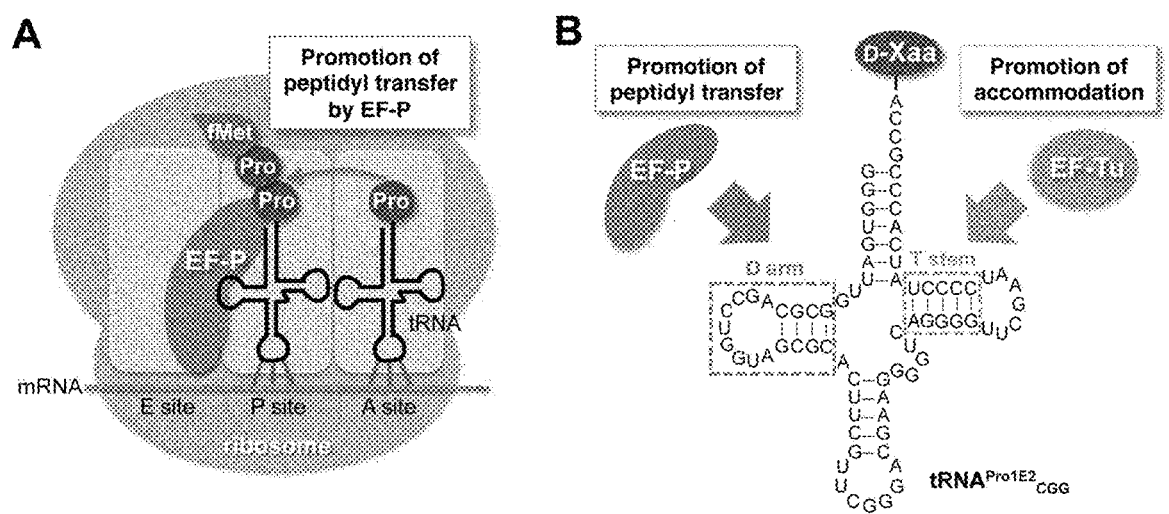

[Fig.2]
A   mRNA (mR1): AUG UAC AAG AAG UAC AAA AAG UAC AAA NNN NNN GGU flag UAA
    peptide (rP1-X₂): fM Y K K Y K K Y K X X G flag (stop)
    mRNA (mR2): AUG UAC AAG AAG UAC AAA AAG UAC AAA NNN NNN NNN flag UAA
    peptide (rP2-X₃): fM Y K K Y K K Y K X X X flag (stop)
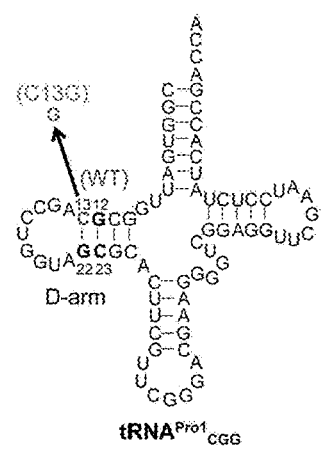
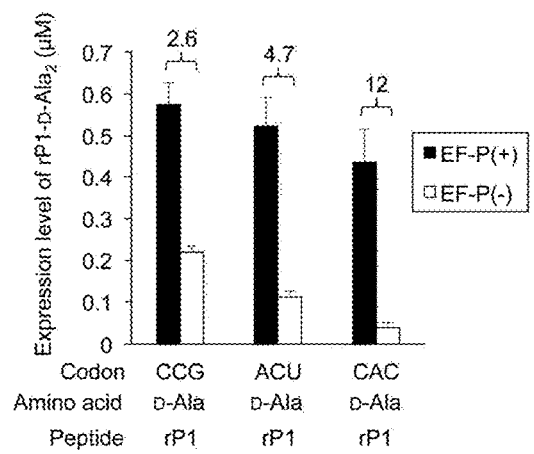
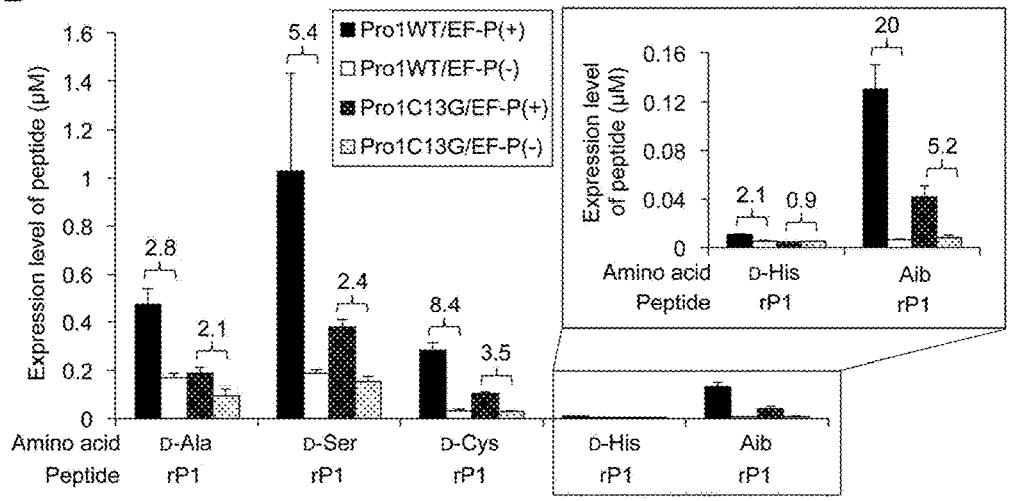
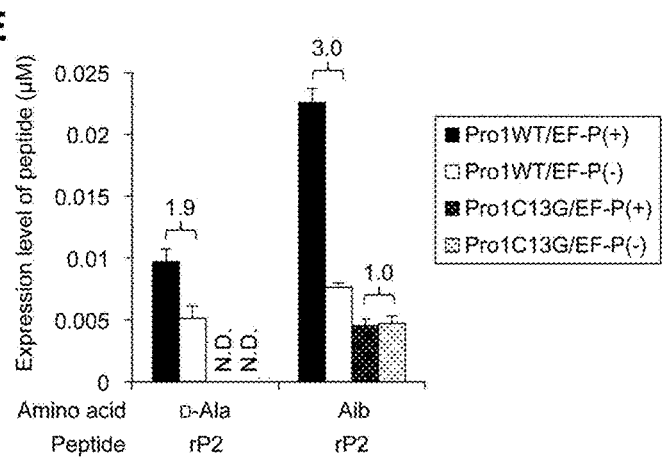

[Fig.3]
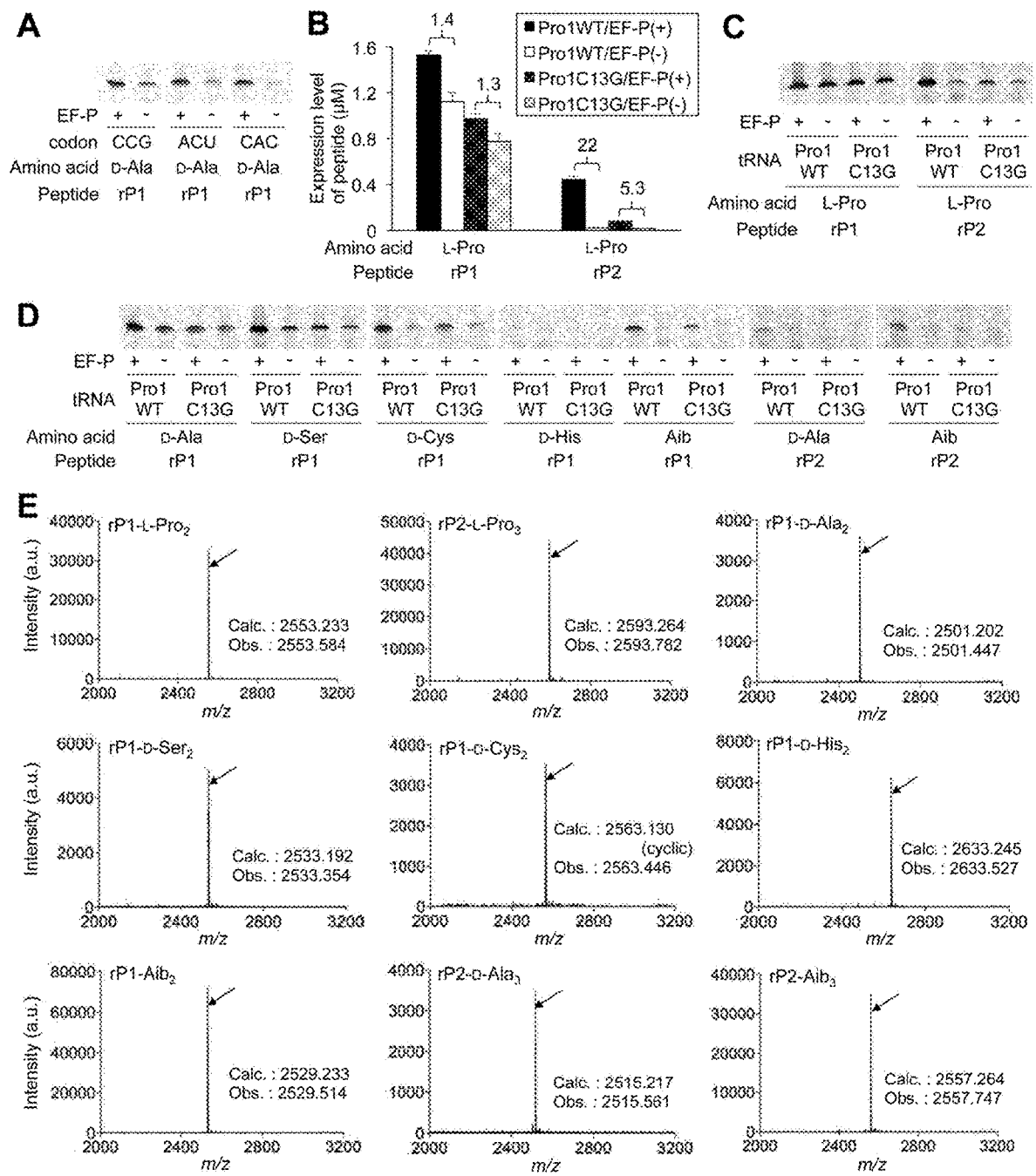

[Fig.4]
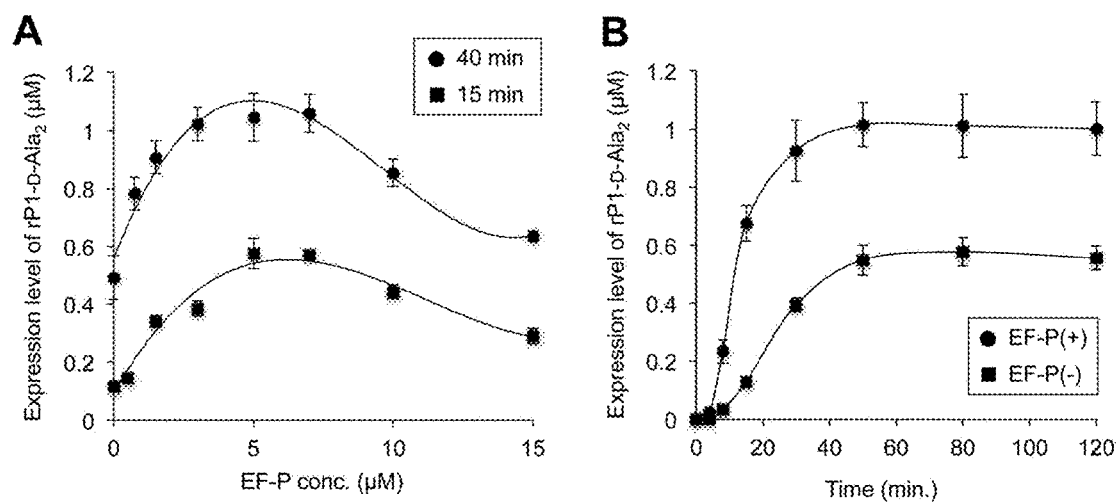

[Fig.5]
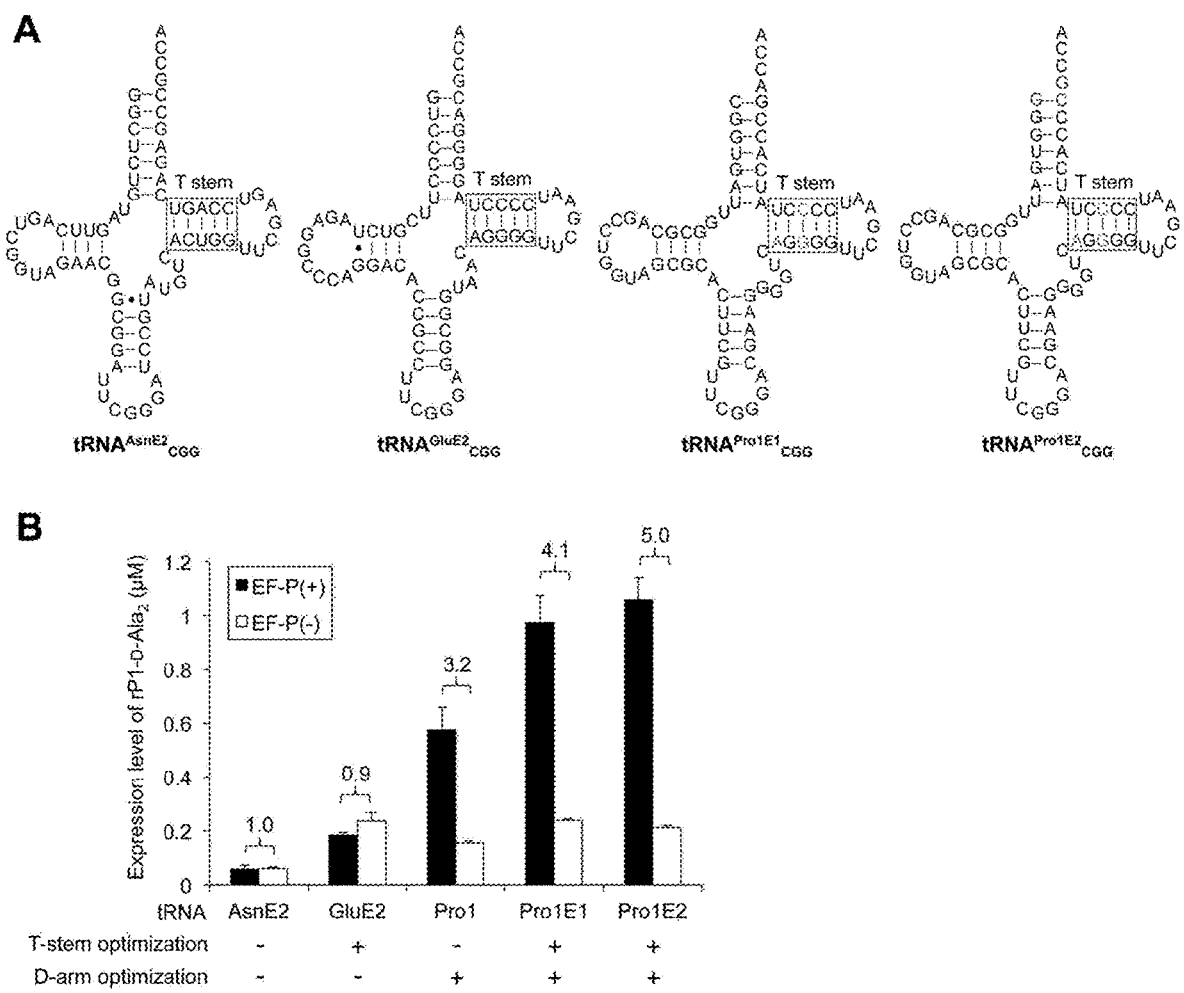

[Fig.6]
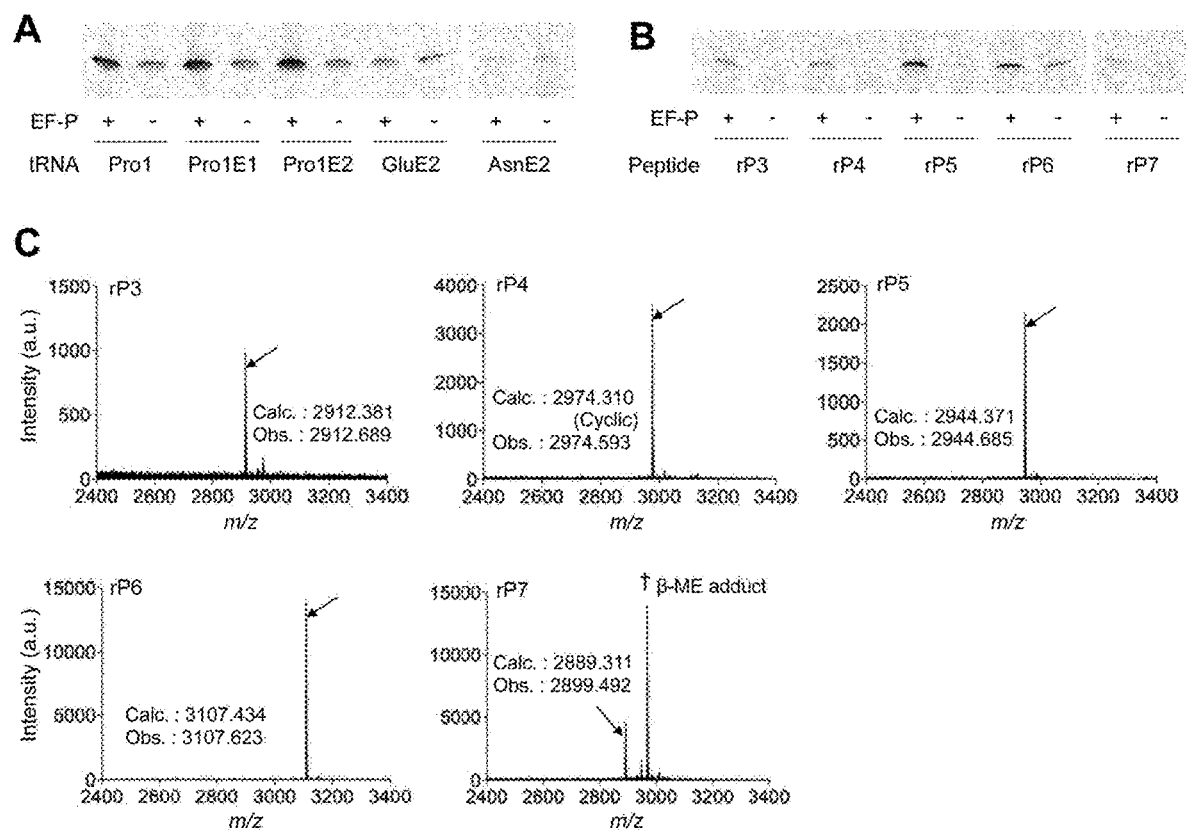

[Fig.7]
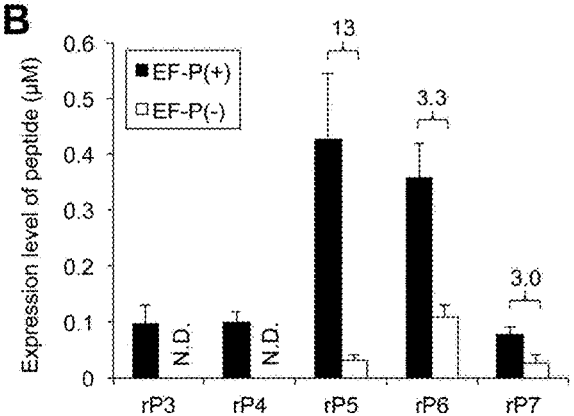

[Fig.8]
A
mRNA (mR8): AUG UAC AAG AAG UAC AAA AAG UAC AAA CAU ACU AUU ACU CAU flag UAA
peptide (rP8): fM Y K K Y K K Y K D-C D-S D-A D-S D-C flag (stop)
                                                    └─── S−S ───┘
mRNA (mR9): AUG GCU GCU CAU AAG AAG AAG flag UAA
peptide (rP9): D-ClAcF D-S D-S D-C K K K flag (stop)
               └──────── S ────────┘
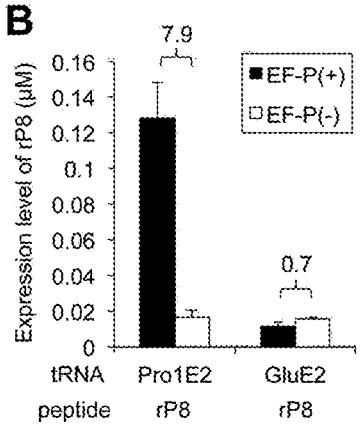 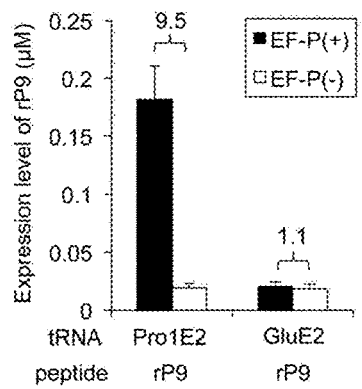

[Fig.9]
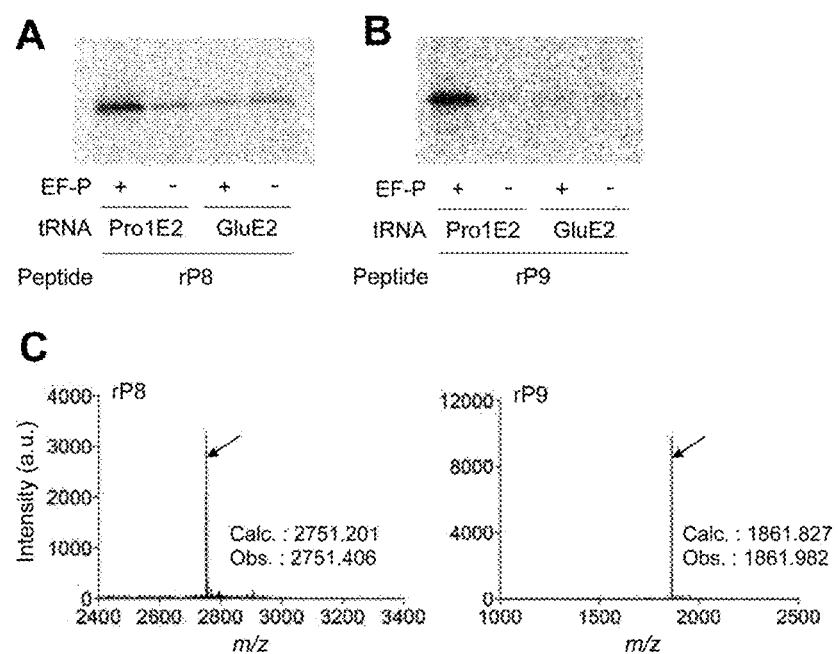

[Fig.10]
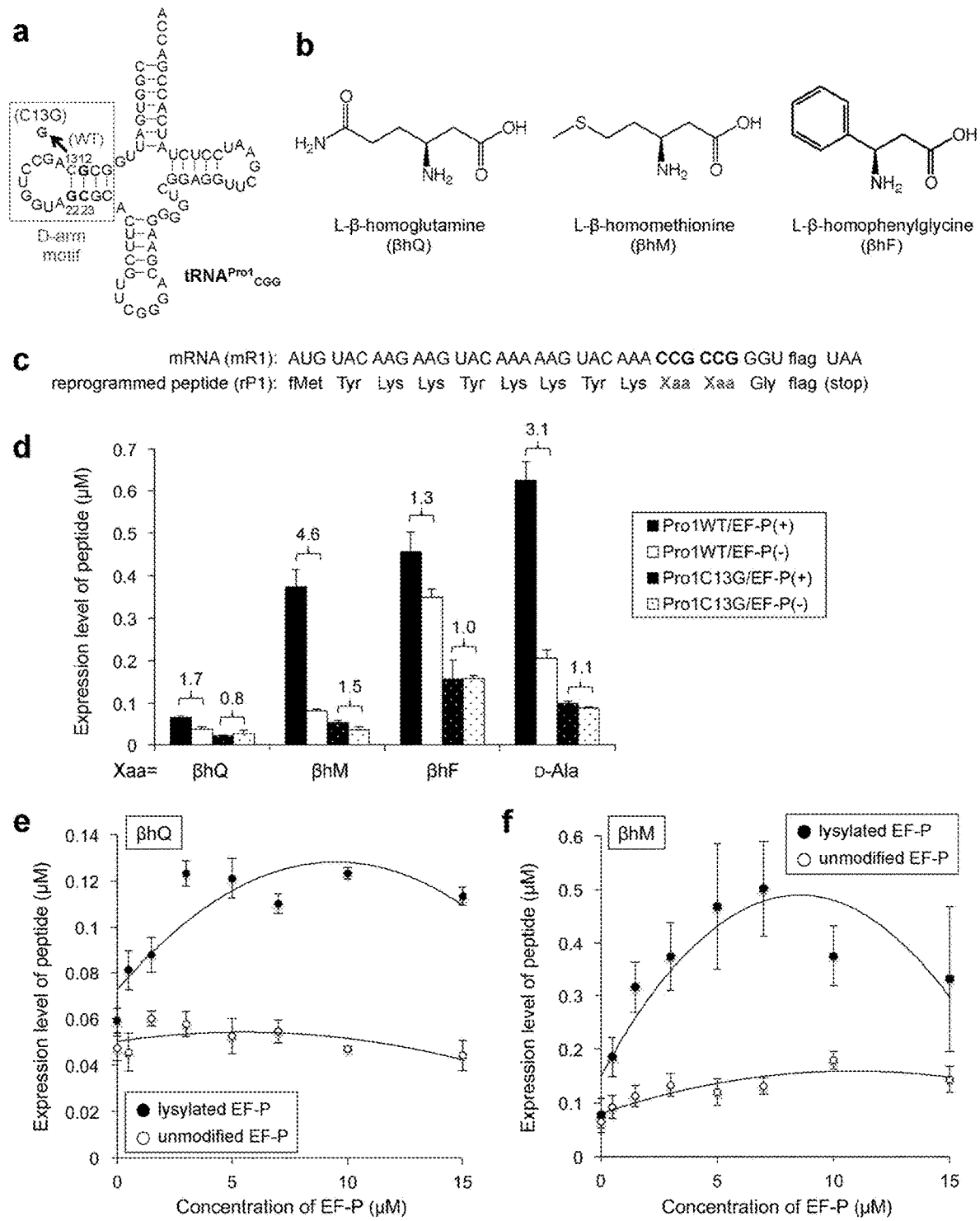

[Fig.11]
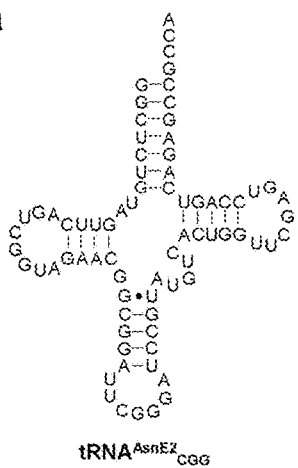
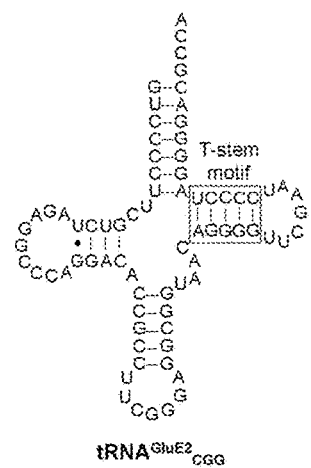
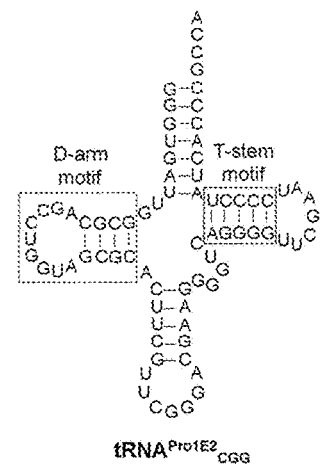
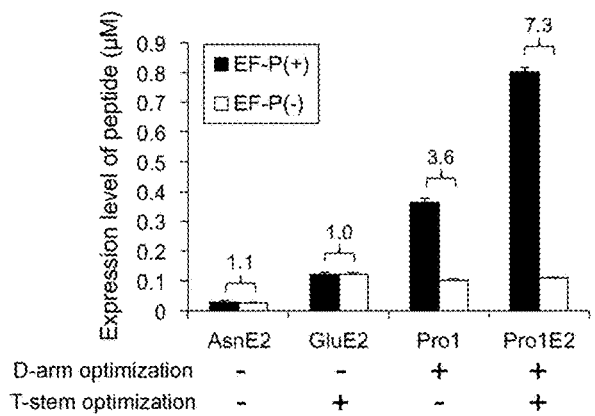
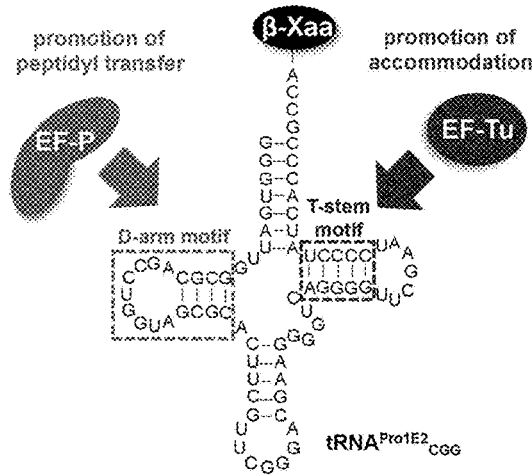

[Fig.12]
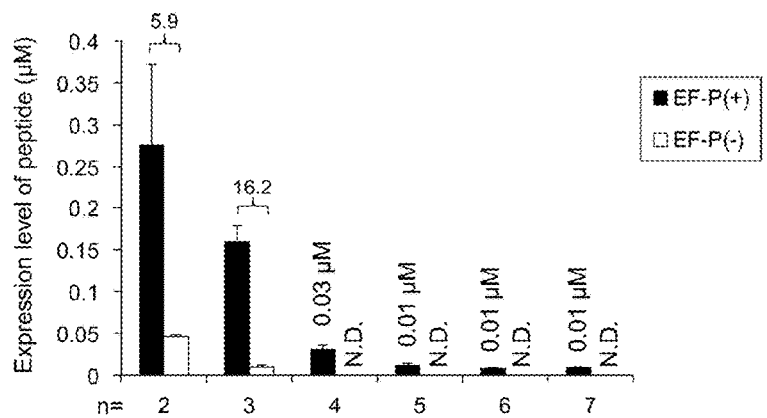
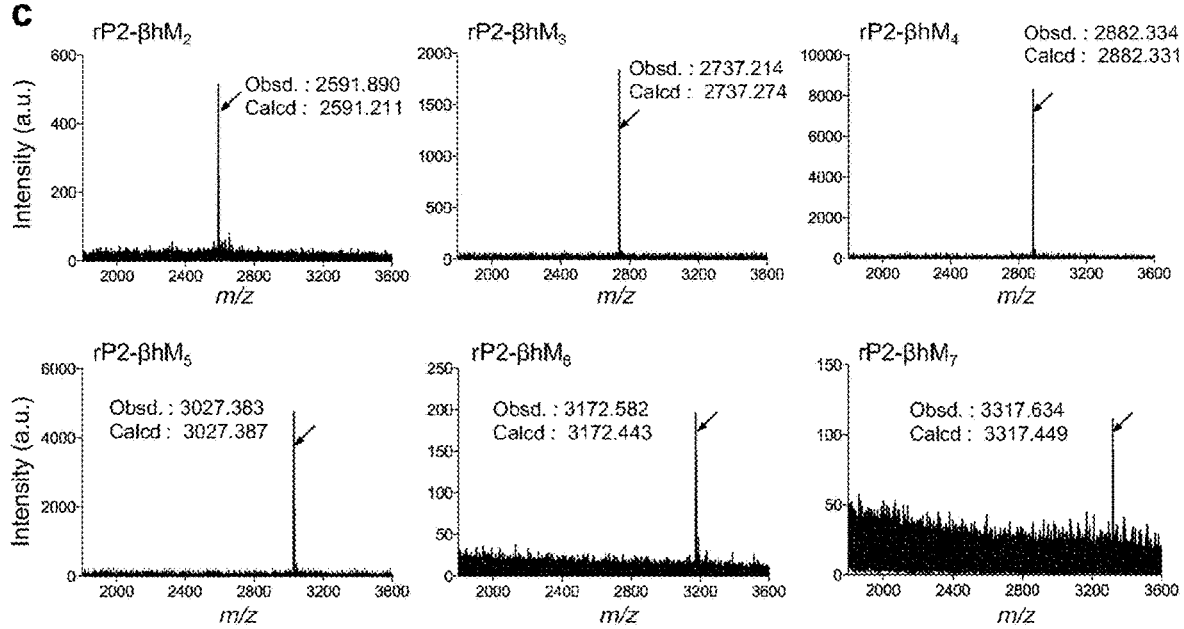

[Fig.13]

a mRNA (mR3-3): AUG UAC AAG AAG UAC AAA AAG UAC AAA AUU CAU AUU flag UAA
reprogrammed peptide (rP3-3): fMet Tyr Lys Lys Tyr Lys Lys Tyr Lys βhM βhF βhM flag (stop)

mRNA (mR3-4): AUG UAC AAG AAG UAC AAA AAG UAC AAA AUU CAU AUU CAU flag UAA
reprogrammed peptide (rP3-4): fMet Tyr Lys Lys Tyr Lys Lys Tyr Lys βhM βhF βhM βhF flag (stop)

mRNA (mR3-5): AUG UAC AAG AAG UAC AAA AAG UAC AAA AUU CAU AUU CAU AUU flag UAA
reprogrammed peptide (rP3-5): fMet Tyr Lys Lys Tyr Lys Lys Tyr Lys βhM βhF βhM βhF βhM flag (stop)

mRNA (mR3-6): AUG UAC AAG AAG UAC AAA AAG UAC AAA AUU CAU AUU CAU AUU CAU flag UAA
reprogrammed peptide (rP3-6): fMet Tyr Lys Lys Tyr Lys Lys Tyr Lys βhM βhF βhM βhF βhM βhF flag (stop)

mRNA (mR3-7): AUG UAC AAG AAG UAC AAA AAG UAC AAA AUU CAU AUU CAU AUU CAU AUU flag UAA
reprogrammed peptide (rP3-7): fMet Tyr Lys Lys Tyr Lys Lys Tyr Lys βhM βhF βhM βhF βhM βhF βhM flag (stop)

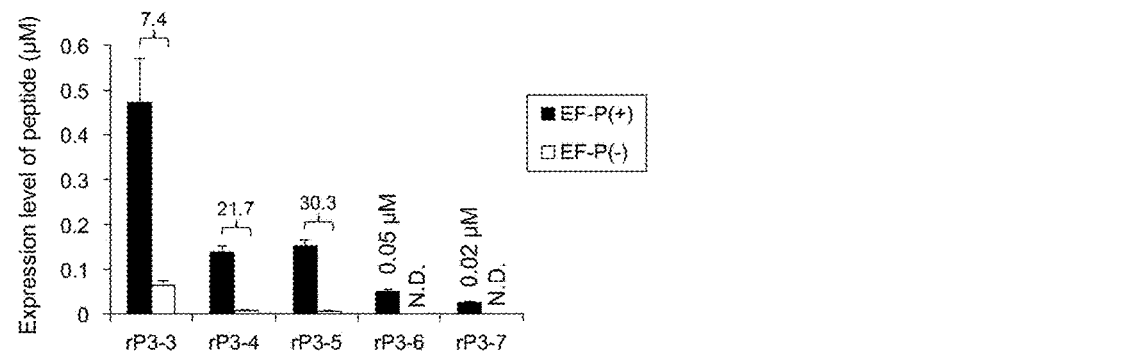

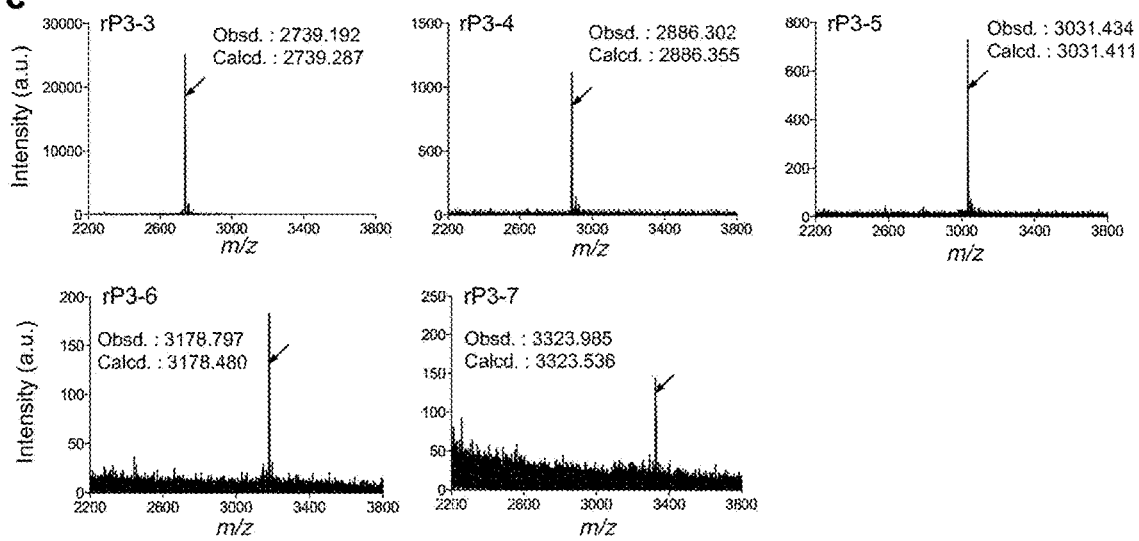

[Fig.14]

a mRNA (mR4): AUG UAC AAG AAG UAC AAA AAG UAC AAA CAU UAC AUU UAC CAU flag UAA
reprogrammed peptide (rP4): fMet Tyr Lys Lys Tyr Lys Lys Tyr Lys βhF Tyr βhM Tyr βhF flag (stop)

mRNA (mR5): AUG UAC AAG AAG UAC AAA AAG UAC AAA ACU UAC AUU UAC CAU flag UAA
reprogrammed peptide (rP5): fMet Tyr Lys Lys Tyr Lys Lys Tyr Lys βhQ Tyr βhM Tyr βhF flag (stop)

mRNA (mR6): AUG UAC AAG AAG UAC AAA AAG UAC AAA AUU AUU UAC UAC CAU CAU flag UAA
reprogrammed peptide (rP6): fMet Tyr Lys Lys Tyr Lys Lys Tyr Lys βhM βhM Tyr Tyr βhF βhF flag (stop)

mRNA (mR7): AUG UAC AAG AAG UAC AAA AAG UAC AAA AUU CAU UAC UAC AUU CAU flag UAA
reprogrammed peptide (rP7): fMet Tyr Lys Lys Tyr Lys Lys Tyr Lys βhM βhF Tyr Tyr βhM βhF flag (stop)

mRNA (mR8): AUG UAC AAG AAG UAC AAA AAG UAC AAA AUU AUU UAC UAC CAU CAU flag UAA
reprogrammed peptide (rP8): fMet Tyr Lys Lys Tyr Lys Lys Tyr Lys βhM βhM Tyr Tyr D-Ala D-Ala flag (stop)

mRNA (mR9): AUG UAC AAG AAG UAC AAA AAG UAC AAA CAU ACU AUU ACU CAU flag UAA
reprogrammed peptide (rP9): fMet Tyr Lys Lys Tyr Lys Lys Tyr Lys βhF D-Ser βhM D-Ser βhF flag (stop)

mRNA (mR10): AUG ACU ACU CAU AAG AAG AAG flag UAA
reprogrammed peptide (rP10): ClAcDF βhM βhM D-Cys Lys Lys Lys flag (stop)
                              └──────────S──────┘ mRNA (mR11): AUG ACU ACU ACU CAU AAG AAG AAG flag UAA
reprogrammed peptide (rP11): ClAcDF βhM βhM βhM D-Cys Lys Lys Lys flag (stop)
                              └────────────S──────────┘

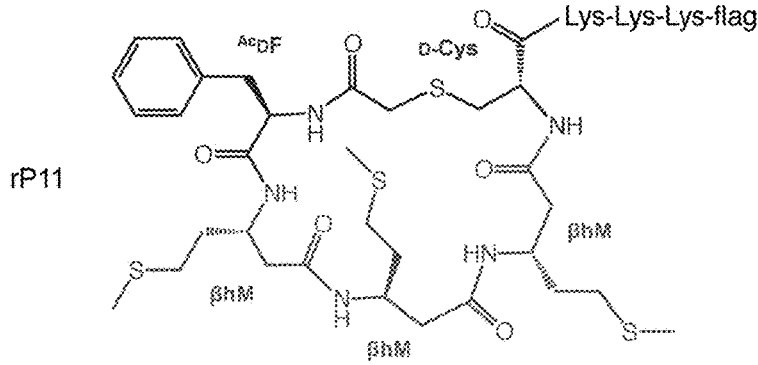

b  rP11

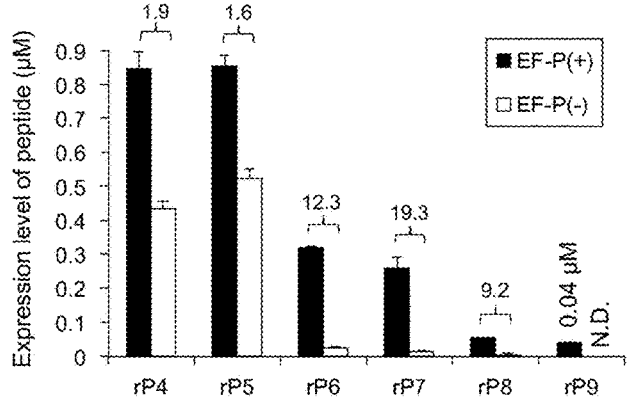

c

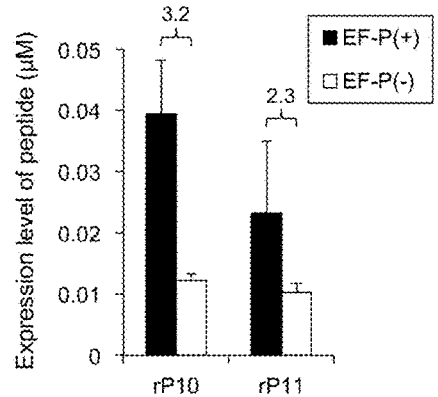

d

[Fig.15]
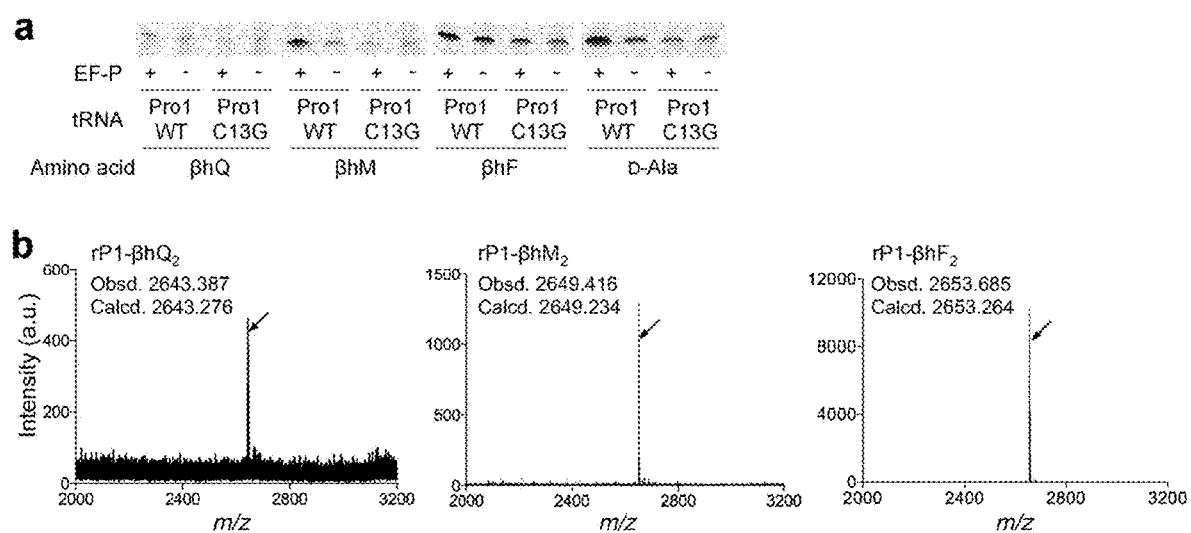

[Fig.16]
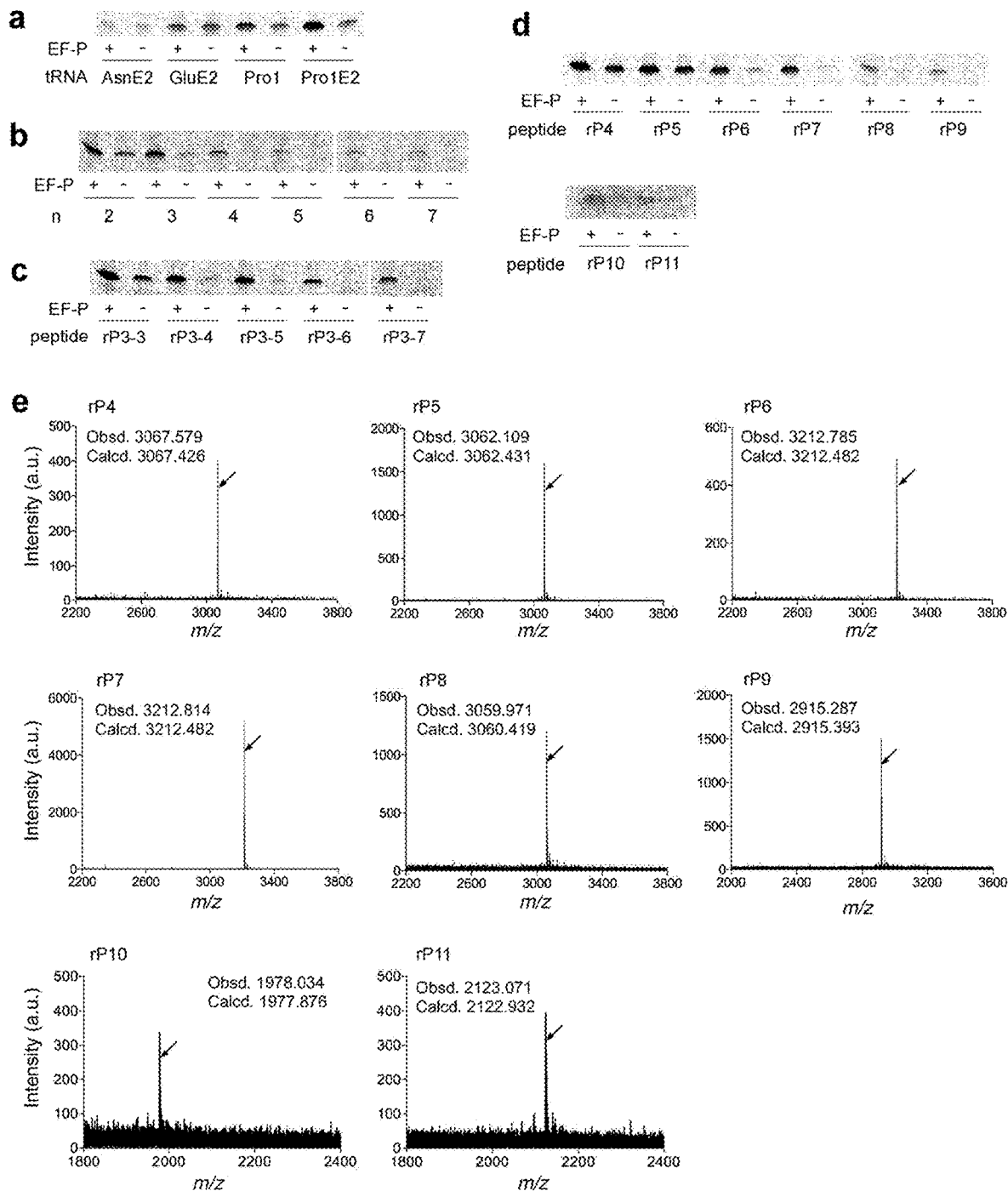

MODIFICATION OF D- AND T-ARMS OF tRNA ENHANCING D-AMINO ACID AND β-AMINO ACID UPTAKE

REFERENCE TO A SEQUENCE LISTING SUBMITTED VIA EFS-WEB

The content of the ASCII text file of the sequence listing named "20230526_034574_021 US1_ST25_sub" which is 42,674 bytes in size was created on May 18, 2023 and electronically submitted via EFS-Web is incorporated herein by reference in its entirety.

TECHNICAL FIELD

The present invention relates to engineering of D- and T-arms of tRNA for enhancing the incorporation of non-proteinogenic amino acids.

BACKGROUND ART

In nature, a ribosomal translation system makes use of 19 proteinogenic L-amino acids and glycine, but non-proteinogenic amino acids such as D-amino acids and β-amino acids are extruded from peptide synthesis or protein synthesis by the ribosomal translation system. D-amino acids and β-amino acids are found in various natural peptides and they are usually synthesized in a ribosomal-independent manner.

Various methods for introducing these non-proteinogenic amino acids are therefore being developed.

For example, non-proteinogenic amino acids such as D-amino acids, N-methylamino acids, β-amino acids, and α-hydroxy acids are introduced by genetic code reprogramming combined with a reconstructed in vitro translation system such as Flexible in vitro translation (FIT) system (Non-Patent Documents 1 to 9).

In spite of success in introduction of some D-amino acids into a peptide chain as disclosed in Non-Patent Documents 4, 5 and from 10 to 12, consecutive introduction of D-amino acids has still a large problem (Non-Patent Documents 4 and 12).

Non-Patent Document 5 discloses use of $tRNA^{GluE2}$ pre-charged with D amino acids prepared using a flexizyme to achieve the consecutive incorporation of the D-amino acids by means of the FIT system. In the method disclosed in Non-Patent Document 5, a higher concentration of EF-Tu is presumed to contribute to the enhancement of accommodation of D-aminoacyl-tRNA. However, the overall expression level of a peptide having two consecutive D-Alas was less than 0.3 μM and was still lower than that of total L-type peptides, that is, about 1.4 μM.

With regards to β-amino acids, in spite of success in introducing a specific β-amino acid into a peptide chain, there remains a large problem in consecutive introduction of β-amino acids (Non-Patent Documents 8, and from 13 to 18).

CITATION LIST

Non-Patent Documents

Non-Patent Document 1: Murakami, H. et al. Nat. Methods 3, 357-359 (2006).
Non-Patent Document 2: Goto, Y. et al. Nat. Protoc. 6, 779-790 (2011).
Non-Patent Document 3: Goto, Y. et al. RNA 14, 1390-1398 (2008).
Non-Patent Document 4: Fujino, T. et al. J. Am. Chem. Soc. 135, 1830-1837 (2013).
Non-Patent Document 5: Katoh, T. et al. Cell Chem. Biol. 24, 46-54 (2017).
Non-Patent Document 6: Kawakami, T. et al. Chem Biol 15, 32-42 (2008).
Non-Patent Document 7: Kawakami, T. et al. J Am Chem Soc 135, 12297-12304 (2013).
Non-Patent Document 8: Fujino, T. et al. J Am Chem Soc 138, 1962-1969 (2016).
Non-Patent Document 9: Ohta, A. et al. Chem Biol 14, 1315-1322 (2007). Non-Patent Document 10: Dedkova, L. M. et al. J. Am. Chem. Soc. 125, 6616-6617 (2003).
Non-Patent Document 11: Dedkova, L. M. et al. Biochemistry 45, 15541-15551 (2006).
Non-Patent Document 12: Achenbach, J. et al. Nucleic Acids Res 43, 5687-5698 (2015).
Non-Patent Document 13: Heckler, T. G. et al. J. Biol. Chem. 258, 4492-4495 (1983).
Non-Patent Document 14: Maini, R. et al. Biochemistry 54, 3694-3706 (2015). Non-Patent Document 15: Iqbal, E. S. et al. Org. Biomol. Chem. 16, 1073-1078 (2018).
Non-Patent Document 16: Dedkova, L. M. et al. Biochemistry 51, 401-415 (2011).
Non-Patent Document 17: Maini, R. et al. Bioorg. Med. Chem. 21, 1088-1096 (2013).
Non-Patent Document 18: Czekster, C. M. et al. J. Am. Chem. Soc. 138, 5194-5197 (2016).

SUMMARY

Technical Problem

The problem to be solved by the present invention is to provide, for translation in a cell-free translation system, a novel translation system capable of synthesizing peptides having therein consecutive non-proteinogenic amino acids.

Solution to Problem

As a result of intensive investigation, the present inventors have found that they can solve the above-described problem, paying attention to the D- and T-arms of aminoacyl-tRNA and completed the present invention.

The present invention is as follows:

(1) A tRNA containing a base sequence represented by SEQ ID NO: 1 and encoding a non-proteinogenic amino acid.

(SEQ ID NO: 1)
$N_1N_2GCN_3N_4N_5N_6N_7N_8N_9N_{10}N_{11}GCN_{12}N_{13}$ (in SEQ ID NO: 1,
$N_1$ to $N_{13}$ each represents an arbitrary base, $N_3$ to $N_{11}$ form a D-loop, and $N_1N_2GC$ forms a base pair with $N_{13}N_{12}CG$).

(2) The tRNA as described above in (1), further containing a base sequence represented by SEQ ID NO: 2.

(SEQ ID NO: 2)
$AGGGG(N_{14})_mCCCCU$ (in SEQ ID NO: 2,
$N_{14}$ represents an arbitrary base, m stands for an integer of 1 or more, $(N_{14})_m$ form a T-loop, and AGGGG forms a base pair with UCCCC).

(3) The tRNA as described above in (1) or (2), wherein a non-proteinogenic amino acid charged at a 3' terminal is a D-amino acid, a β-amino acid, or an α,α-disubstituted amino acid.

(4) A translation system for the synthesis of a peptide having two or more consecutive non-proteinogenic amino acids therein, containing the tRNA described above in any of (1) to (3).

(5) A method of constructing a peptide library, including a step of translating in a cell-free translation system by using the tRNA as described above in any of (1) to (3).

(6) A method of constructing a library of a complex between a peptide and an mRNA encoding the peptide, including a step of translating in a cell-free translation system by using the tRNA as described above in any of (1) to (3).

(7) A peptide library constructed by the method as described above in (5) or a peptide-mRNA complex library constructed by the method as described above in (6). (8) The peptide library or peptide-mRNA complex library as described above in (7), including a peptide having two or more consecutive non-proteinogenic amino acids.

(9) The peptide library or peptide-mRNA complex library as described above in (8), including a peptide having four or more consecutive non-proteinogenic amino acids and being intramolecularly crosslinked between the non-proteinogenic amino acids.

Advantageous Effects of Invention

The present invention makes it possible to provide, for translation in a cell-free translation system, a novel translation system capable of synthesizing a peptide having consecutive non-proteinogenic amino acids.

BRIEF DESCRIPTION OF DRAWINGS

FIG. 1 is a schematic view showing promotion of incorporation of proline and D-amino acid by EF-P. FIG. 1A shows EF-P, a prokaryotic translation factor that promotes peptide bond formation between two prolines (Pro). EF-P has a role of promoting incorporation of consecutive prolines. EF-P binds to ribosome in between an E site and a P site, interacts with the peptidyl-prolyl-tRNA at P site, and promotes peptidyl transfer between the peptidyl-prolyl-tRNA at P site and the prolyl-tRNA at A site. FIG. 1B shows the structure of tRNA$^{Pro1E2}$ having a chimeric structure of D-arm of tRNA$^{Pro1}$ and T-stem of tRNA$^{GluE2}$. The sequence in FIG. 1B is SEQ ID NO: 15.

FIG. 2 shows promotion of D-amino acid incorporation by EF-P. FIG. 2A shows the mRNA sequence of mR1 and mR2 and the peptide sequence of rP1 and rP2 respectively corresponding thereto, each used in Examples. An arbitrarily selected codon is introduced into NNN and is used for incorporation of D-amino acid (X) by using a pre-charged D-aminoacyl-tRNA. The amino acid sequence of flag is DYKDDDDK (SEQ ID NO: 113). FIG. 2B shows the structure of tRNA used for incorporation of D-amino acid at CCG codon. A wild type tRNA$^{Pro1}_{CGG}$ (WT) has a C/G base pair at positions 13 and 22. A tRNA$^{Pro1}_{CGG}$ (C13G) mutant has C-to-G mutation at position 13 to break formation of the base pair. The sequence of an anticodon loop can be arbitrarily changed for decoding different codons. FIG. 2C shows an expression level of rP1 peptide having two D-alanines introduced therein. Codons used for D-alanine incorporation are shown. Black bars indicate EF-P(+) translation system and white outlined bars show EF-P(−) translation system. Numbers above the bars mean a translation yield calculated as a ratio of EF-P(+) to EF-P(−). The EF-P concentration in the EF-P(+) translation system is 5 μM. Translation time is 15 minutes and error bars are s. d. (n=3). FIG. 2D and FIG. 2E show the expression level of rP1 peptide (FIG. 2D) and rP2 peptide (FIG. 2E) containing two or three consecutive D-amino acids or Aibs (2-aminobutyric acids). Wild-type tRNA$^{Pro1}_{CGG}$ (WT) (plain bars) or a C13G mutant of tRNA$^{Pro1}_{CGG}$ (dotted bars) were used for incorporation of D-amino acids or Aibs at CCG codon. Black bars indicate EF-P(+) translation system and white outlined bars indicate EF-P(−) translation system. Numbers above the bars mean a translation yield calculated as a ratio of EF-P(+) to EF-P(−). The concentration of EF-P in the EF-P(+) translation system was 5 μM. Translation time is 15 minutes and error bars are s. d. (n=3). An enlarged graph showing incorporation of D-Histidine and Aib is shown in the upper right side of FIG. 2D. FIG. 2D and FIG. 2E show that EF-P recognizes P-site peptidyl D-aminoacyl-tRNA as well as recognizing peptidyl-L-prolyl-tRNA. The sequences in FIG. 2A from top to bottom are SEQ ID NOs: 78, 120, 79, and 121, respectively. The sequence in FIG. 2B is SEQ ID NO: 10.

FIG. 3A shows the results of tricine SDS-PAGE analysis of rP1 peptide having two consecutive D-alanines (refer to FIG. 2C). FIG. 3B shows an expression level of rP1 peptide and rP2 peptide containing 2 or 3 consecutive L-prolines. Wild type tRNA$^{Pro1}_{CGG}$ (WT) (normal bar) or a C13G mutant of tRNA$^{Pro1}_{CGG}$ (dot bar) was used for L-proline incorporation at CCG codon. Black bars indicate EF-P(+) translation system and white outlined bars show EF-P(−) translation system. Numbers above the bars mean a translation yield calculated as a ratio of EF-P(+) to EF-P(−). The EF-P concentration in the EF-P(+) translation system was 5 μM. Translation time is 15 minutes and error bars are s. d. (n=3). FIG. 3C and FIG. 3D show the results of tricine SDS-PAGE analysis of rP1 peptide and rP2 peptide having two or three consecutive L-prolines (FIG. 3C) or D-amino acids or Aibs (FIG. 3D). Translation was performed in a 2.5 μL of a reaction solution at 37° C. for 15 minutes in the presence or absence of EF-P (refer to FIGS. 2D and 2E). FIG. 3E shows the MALDI-TOF-MS spectrum of rP1 peptide and rP2 peptide. Wild type tRNA$^{Pro1}$ was used for incorporation of L-proline, D-amino acid, and Aib. The arrows show peaks corresponding to the intended products. The calculated value and the observed value are indicated by m/z.

FIG. 4 shows the titration of EF-P and time-course analysis in the translation of a D-Ala-containing peptide. FIG. 4A shows the titration of an EF-P concentration in the translation of rP1 peptide containing two consecutive D-alanines at CCG codons. The translation time was set at 40 minutes (black circle) or 15 minutes (black square). Error bars are s. d. (n=3). FIG. 4B shows the time-course analysis of the translation of rP1 peptide containing two consecutive D-alanines. The black circle and black square show the results in the EF-P(+) and EF-P(−) translation systems, respectively. The concentration of EF-P in the EF-P(+) translation system was 5 μM. Error bars are s. d. (n=3).

FIG. 5 shows the effect of a tRNA structure on the EF-P-dependent promotion of D-amino acid incorporation. FIG. 5A shows the structure of tRNAs used for D-amino acid incorporation. The pale letters in tRNA$^{Pro1E1}_{CGG}$ and tRNA$^{Pro1E2}_{CGG}$ indicate a mutation from a wild-type tRNA$^{Pro1}_{CGG}$ sequence (An *Escherichia coli* prolyl-tRNA synthase cannot recognize tRNAs having such mutation introduced therein). FIG. 5B shows an expression level of rP1 peptide containing two consecutive D-alanines at CCG codon. tRNA used for D-Ala incorporation is indicated. Numbers above the bars mean a translation yield calculated as a ratio of EF-P(+) to EF-P(−). Translation time is 15 minutes and error bars are s. d. (n=3). The sequences in FIG. 5A from left to right are SEQ ID NOs: 20, 19, 14, and 15, respectively.

FIG. 6A shows the tricine SDS-PAGE analysis results of rP1 peptide synthesized using various tRNAs for incorporating two consecutive D-alanines therein. Translation was performed in a 2.5 μL of a reaction solution at 37° C. for 15 minutes in the presence or absence of EF-P (refer to FIG. 5B). FIG. 6B shows the tricine SDS-PAGE analysis results of rP3, rP4, rP5, rP6, and rP7 peptides. $tRNA^{Pro1E2}$ was used for D-amino acid incorporation. Translation was performed in a 2.5 μL of a reaction solution at 37° C. for 15 minutes in the presence or absence of EF-P (refer to FIG. 7B). FIG. 6C shows the MALDI-TOF-MS spectrum of rP3, rP4, rP5, rP6, and rP7 peptides synthesized using 5 μM EF-P and $tRNA^{Pro1E2}$. The arrows show peaks corresponding to the intended products. The calculated value and the observed value are indicated by m/z. It is to be noted that rP7 peptide was detected mainly as a 2-mercaptoethanol adduct to D-cysteine.

FIG. 7 shows D-amino acid incorporation into various peptide sequences promoted by EF-P. FIG. 7A shows mRNA sequences (mR3, mR4, mR5, mR6, and mR7) and peptide sequences (rP3, rP4, rP5, rP6, and rP7) corresponding thereto. FIG. 7B shows the expression level of peptides rP3, rP4, rP5, rP6, and rP7 for which a $tRNA^{Pro1E2}$ mutant was used for incorporation of a D-amino acid. Numbers above the bars mean a translation yield calculated as a ratio of EF-P(+) to EF-P(−). Translation time is 15 minutes and error bars are s. d. (n=3). The sequences in FIG. 7A from top to bottom are SEQ ID NOs: 80, 122, 81, 123, 82, 124, 83, 125, 84, and 126, respectively.

FIG. 8 shows translation of a cyclic D-peptide formed by a disulfide bond or a thioether bond. FIG. 8A shows mRNA sequences (mR8 and mR9) and peptide sequences (rP8 and rP9) corresponding thereto. Two D-cysteines contained in rP8 peptide form a disulfide bond to form a macrocyclic structure. The sulfhydryl group of the D-Cysteine in rP9 peptide attacks the α-carbon of the N-terminal chloroacetyl (ClAc) group to form a thioether bond and thereby form a macrocyclic structure. FIG. 8B and FIG. 8C show the expression level of rP8 peptide (FIG. 8B) and rP9 peptide (FIG. 8C) for which $tRNA^{Pro1E2}$ or $tRNA^{GluE2}$ was used for D-amino acid incorporation. Numbers above the bars mean a translation yield calculated as a ratio of EF-P(+) to EF-P(−). Translation time is 15 minutes and error bars are s. d. (n=3). The sequences in FIG. 8a from top to bottom are SEQ ID NOs: 85, 127, 86, and 128, respectively.

FIG. 9A and FIG. 9B show the tricine SDS-PAGE analysis results of rP8 peptide (FIG. 9A) and rP9 peptide (FIG. 9B). For D-amino acid incorporation, $tRNA^{Pro1E2}$ or $tRNA^{GluE2}$ was used. Translation was performed in a 2.5 μL of a reaction solution at 37° C. for 15 minutes in the presence or absence of EF-P (refer to FIGS. 8B and 8C). FIG. 9C shows the MALDI-TOF-MS spectrum of rP8 and rP9 peptides synthesized using 5 μM EF-P and $tRNA^{Pro1E2}$. The arrows show peaks corresponding to the intended products. The calculated value and the observed value are indicated by m/z.

FIG. 10 shows promotion of β-amino acid incorporation by EF-P. FIG. 10a shows the structure of tRNA used for β-amino acid incorporation at CCG codon. FIG. 10b shows the structure of a β-amino acid. FIG. 10c shows, similar to FIG. 2A, the mRNA sequence of mR1 used in Examples for β-amino acid incorporation and the peptide sequence of rP1 corresponding thereto. The CCG codon is used for β-amino acid (Xaa) incorporation by using a pre-charged β-aminoacyl-tRNA. The amino acid sequence of flag is DYKDDDDK. FIG. 10d shows the expression level of rP1 peptide containing two consecutive β-amino acids or D-alanine. Wild-type $tRNA^{Pro1}_{CGG}$ (WT) (plain bars) or $tRNA^{Pro1}_{CGG}$, that is, a C13G mutant (dotted bars) were used for incorporation of a β-amino acid or D-alanine at CCG codon. Black bars indicate an EF-P(+) translation system and white outlined bars indicate an EF-P(−) translation system. Numbers above the bars mean a translation yield calculated as a ratio of EF-P(+) to EF-P(−). The concentration of EF-P in the EF-P(+) translation system was 5 μM. Translation time is 15 minutes and error bars are s. d. (n=3). FIG. 10e and FIG. 10f show the titration of an EF-P concentration in the translation of rP1 peptide containing two consecutive β-amino acids. For the titration, lysylated (Lysylated) EF-P (black circle) or unmodified EF-P (white circle) were used. Error bars are s. d. (n=3). The sequence in FIG. 10a is SEQ ID NO: 10. The sequences in FIG. 10c from top to bottom are SEQ ID NOs: 87 and 102, respectively.

FIG. 11 shows the effect of a tRNA structure on the EF-P dependent promotion of β-amino acid incorporation. FIG. 11a shows the structure of tRNAs used for β-amino acid incorporation. The dot lines show a T-stem motif or a D-arm motif optimized for EF-Tu and EF-P binding. FIG. 11b shows the expression level of a rP1 peptide containing two consecutive βhM. tRNAs used for βhM incorporation are shown. Numbers above the bars mean a translation yield calculated as a ratio of EF-P(+) to EF-P(−). Translation time is 15 minutes and error bars are s. d. (n=3). FIG. 11c shows the structure of $tRNA^{Pro1E2}$ having a D-arm motif and a T-stem motif optimized for β-amino acid incorporation. The sequences in FIG. 11a from left to right are SEQ ID NOs: 20, 19, and 15, respectively. The sequence in FIG. 11c is SEQ ID NO: 15.

FIG. 12 shows incorporation of up to 7 consecutive β-amino acids. FIG. 12a shows, similar to FIG. 2A, the mRNA sequence of the mR2 used in Examples for β-amino acid incorporation and the peptide sequence of rP2 corresponding thereto. From 2 to 7 consecutive βhMs were incorporated at CCG codons (n=2 to 7) by $tRNA^{Pro1E2}_{CGG}$. FIG. 12b shows the expression level of rP2 peptide containing consecutive βhMs. Numbers above the bars mean a translation yield calculated as a ratio of EF-P(+) to EF-P(−) or an expression level (μM). N.D. means "not detected". Translation time is 15 minutes and error bars are s. d. (n=3). FIG. 12c shows the MALDI-TOF-MS spectrum of rP2 peptide having from 2 to 7 consecutive βhMs incorporated therein. In the translation system, 5 μM EF-P was present. The arrows show peaks corresponding to the intended products. The calculated value and the observed value are indicated by m/z. The sequences in FIG. 12a from top to bottom are SEQ ID NOs: 88 and 103, respectively.

FIG. 13 shows incorporation of two kinds of β-amino acids. FIG. 13a shows, similar to FIG. 2A, the mRNA sequence of from mR3-3 to mR3-7 used in Examples for β-amino acid incorporation and the peptide sequence of from rP3-3 to rP3-7 corresponding thereto. βhM and βhF were incorporated at AUU codon and CAU codon by using $tRNA^{Pro1E2}_{Gau}$ and $tRNA^{Pro1E2}_{GUG}$, respectively. FIG. 13b shows the expression level of from rP3-3 peptide to rP3-7 peptide. Numbers above the bars mean a translation yield calculated as a ratio of EF-P(+) to EF-P(−) or an expression level (μM). N.D. means "not detected". Translation time is 15 minutes and error bars are s. d. (n=3). FIG. 13c shows the MALDI-TOF-MS spectrum of rP3-3 peptide to rP3-7 peptide having βhM and βhF incorporated therein. In the translation system, 5 μM EF-P was present. The arrows show peaks corresponding to the intended products. The calculated value and the observed value are indicated by m/z. The sequences in FIG. 13a from top to bottom are SEQ ID NOs: 89, 104, 90, 105, 91, 106, 92, 107, 93, and 108, respectively.

FIG. 14 shows incorporation of a plurality of D-amino acids and β-amino acids. FIG. 14a shows, similar to FIG. 2A, the mRNA sequence of from mR4 to mR11 used in Examples for incorporation of D-amino acids and β-amino acids and the peptide sequence of from rP4 to rP11 corresponding thereto. βhM and βhF were incorporated at AUU codon and CAU codon by using tRNA$^{Pro1E2}_{GAU}$ and tRNA$^{Pro1E2}_{GUG}$, respectively whereas D-amino acids were incorporated at ACU codon by using tRNA$^{Pro1E2}_{GGU}$. FIG. 14b shows the structure of a macrocyclic peptide rP11. The thiol group of D-cysteine reacts with the N-terminal chloroacetyl group to form a thioether bond and thereby produce a macrocyclic structure. FIG. 14c and FIG. 14d show the expression level of from rP4 peptide to rP9 peptide and that of from rP10 peptide to rP11 peptide, respectively. Numbers above the bars mean a translation yield calculated as a ratio of EF-P(+) to EF-P(−) or an expression level (μM). N.D. means "not detected". Translation time is 15 minutes and error bars are s. d. (n=3). The sequences in FIG. 14a from top to bottom are SEQ ID NOs: 94, 109, 95, 110, 96, 11, 97, 112, 98, 129, 99, 130, 100, 131, 101, and 132, respectively.

FIG. 15a shows the results of tricine SDS-PAGE analysis of a rP1 peptide having β-amino acid(s) or D-alanine(s) incorporated therein. tRNAs used for the incorporation of these amino acids are shown. Refer to FIG. 10d about quantification of each band. FIG. 15b shows the MALDI-TOF-MS spectrum of rP1 peptide. Wild type tRNA$^{Pro1}$ was used for the incorporation of these amino acids. In the translation system, 5 μM EF-P was present. The arrows show peaks corresponding to the intended products. The calculated value and the observed value are indicated by m/z.

FIG. 16a to FIG. 16d respectively show the tricine SDS-PAGE analysis results of rP1 peptide (FIG. 16a), rP2 peptide (FIG. 16b), from rP3-3 peptide to rP3-7 peptide (FIG. 16c), and from rP4 peptide to rP11 peptide (FIG. 16d). Refer to FIG. 11b, FIG. 12b, FIG. 13b, and FIG. 14c and FIG. 14d about quantification of each band. FIG. 16e shows the MALDI-TOF-MS spectrum of from rP4 peptide to rP11 peptide. Wild type tRNA$^{Pro1}$ was used for the incorporation of these amino acids. In the translation system, 5 μM EF-P was present. The arrows show peaks corresponding to the intended products. The calculated value and the observed value are indicated by m/z.

DESCRIPTION OF EMBODIMENTS

The tRNA of the present invention is a tRNA containing a base sequence represented by SEQ ID NO: 1 and encoding a non-proteinogenic amino acids.

(SEQ ID NO: 1)
$N_1N_2GCN_3N_4N_5N_6N_7N_8N_9N_{10}N_{11}GCN_{12}N_{13}$

In SEQ ID NO: 1,
$N_1$ to $N_{13}$ each represents an arbitrary base, $N_3$ to $N_{11}$ form a D-loop, and $N_1N_2GC$ forms base pairs with $N_{13}N_{12}CG$.

An EF-P protein which is a translation factor has an important role in promoting elongation of proline-proline (Pro-Pro) bond formation and alleviates stalling of translation elongation (ribosomal stalling) caused by peptidyl-tRNA drop-off at the Pro-Pro sequence.

The EF-P protein recognizes a 9-nt D-loop having a structure closed with a stable 4-bp D-stem sequence, which is a specific D-arm motif found in tRNA$^{Pro}$ isoacceptors, for promotion of proline-selective peptidyl transfer and depends on tRNA$^{Pro}$ in the promotion of a Pro-Pro transfer reaction rate.

In the resent invention, the base sequence represented by SEQ ID NO: 1 is a D-arm composed of a D-loop and D-stem and by introducing the base sequence represented by SEQ ID NO: 1 into tRNA, peptidyl transfer by EF-P peptide can be promoted.

Another structure in the tRNA of the present invention containing a base sequence represented by SEQ ID NO: 1, that is, an acceptor stem, an anticodon stem, an anticodon loop, a variable loop, and T arm may have any base sequences. Of these, the anticodon loop may have, as needed, a base sequence corresponding to a codon to which a non-proteinogenic amino acid is assigned.

The tRNA, at the 3' terminal thereof, has a CCA sequence and binds to an arbitrary amino acid. The tRNA of the present invention binds to a non-proteinogenic amino acid.

The term "tRNA encodes a non-proteinogenic amino acid" as used herein means that the tRNA binds to the non-proteinogenic amino acid via the CCA sequence of the tRNA.

In SEQ ID NO: 1, any base can be selected insofar as $N_1N_2$ and $N_{13}N_{12}$ form a base pair, but $N^1$ and $N^{13}$ are preferably G and C, respectively and $N_2$ and $N_{12}$ are preferably C and G, respectively.

The base sequence represented by SEQ ID NO: 1 is preferably a base sequence represented by SEQ ID NO: 3.

(SEQ ID NO: 3)
$GCGCN_3N_4N_5N_6N_7N_8N_9N_{10}N_{11}GCGC$

In SEQ ID NO: 3
$N_3$ to $N_{11}$ have the same meanings as described above and GCGC forms a base pair with CGCG.

The base sequence of from $N_3$ to $N_{11}$ in SEQ ID NO: 1 and SEQ ID NO: 3 is preferably a base sequence represented by SEQ ID NO: 4.

(SEQ ID NO: 4)
AGCCUGGUA

The base sequence represented by SEQ ID NO: 4 forms a D-loop in tRNA.

In SEQ ID NO: 4, one base or some bases may be substituted.

The term "some bases may be substituted" means that in 9 bases forming the D-loop, 2, 3, 4, 5, 6, 7, 8, or 9 bases may be substituted. In the 9 bases forming the D-loop, from 1 to 4 bases may be substituted, from 1 to 3 bases may be substituted, from 1 to 2 bases may be substituted, or one base may be substituted.

The base sequence represented by SEQ ID NO: 1 is preferably a base sequence represented by SEQ ID NO: 5 and is preferably a base sequence represented by SEQ ID NO: 6.

$N_1N_2$GCGCAGCCUGGUAGCGCN$_{12}N_{13}$ (SEQ ID NO: 5)

In SEQ ID NO: 5,
$N_1$, $N_2$, $N_{12}$, and $N_{13}$ have the same meanings as described above and $N_1N_2$GC forms a base pair with $N_{13}N_{12}$CG.

GCGCGCAGCCUGGUAGCGCGC (SEQ. ID. NO: 6)

In SEQ ID NO: 5 and SEQ ID NO: 6, one base or some bases may be substituted.

The term "in SEQ ID NOS: 5 and 6, some bases may be substituted" means that in SEQ ID NO: 4 showing the 9 bases forming the D-loop, 2, 3, 4, 5, 6, 7, 8, or 9 bases may be substituted. In SEQ ID NO: 4 showing the 9 bases forming the D-loop, from 1 to 4 bases may be substituted, from 1 to 3 bases may be substituted, from 1 to 2 bases may be substituted, or one base may be substituted.

The T-stem of the aminoacyl-tRNA regulates the interaction with an EF-Tu protein and enhances incorporation of a non-proteinogenic amino acid such as N-methylamino acid.

In the present invention, the base sequence represented by SEQ ID NO: 2 is a T-arm composed of a T-loop and a T-stem and by introducing the base sequence represented by SEQ ID NO: 2 into the tRNA, accommodation by an EF-Tu protein is accelerated when a non-proteinogenic amino acid is introduced into a peptide or a protein.

The tRNA of the present invention is preferably a tRNA further containing the base sequence represented by SEQ ID NO: 2.

AGGGG($N_{14}$)$_m$CCCCU (SEQ ID NO: 2)

In SEQ ID NO: 2,
$N_{14}$ represents an arbitrary base, m stands for an integer of 1 or more, ($N_{14}$)$_m$ form a T-loop, and AGGGG forms a base pair with UCCCC.
m is not particularly limited insofar as ($N_{14}$)$_m$ form a T-loop, and it may be an integer of 2, 3, 4, 5, 6, 7, 8, 9, or 10 and is preferably an integer of from 6 to 8.
($N_{14}$)$_m$ are preferably a base sequence represented by SEQ ID NO: 7 derived from the T-loop of tRNA$^{GluE2}$.

UUCGAAU (SEQ ID NO: 7)

In SEQ ID NO: 7, one base or some bases may be substituted.

The term "some bases may be substituted" means that in 7 bases forming the T-loop, 2, 3, 4, 5, 6, or 7 bases may be substituted. In the 7 bases forming the T-loop, from 1 to 3 bases may be substituted, from 1 to 2 bases may be substituted, or one base may be substituted.

In SEQ ID NO: 2, AGGGG and UCCCC which form a base pair form a T-stem.

In the base sequence forming a T-stem, one base or some bases may be substituted insofar as a base pair is formed.

The term "in the T-stem of SEQ ID NO: 2, some bases may be substituted" means that in 10 bases forming the T-stem, 2, 3, 4, 5, 6, 7, 8, 9, or 10 bases may be substituted. In the 10 bases forming the T-stem, 2 bases may be substituted, 4 bases may be substituted, 6 bases may be substituted, or 1, 3, or 5 bases may be substituted insofar as a base pair is formed.

A tRNA preferred in the present invention contains both the base sequence represented by SEQ ID NO: 1 and the base sequence represented by SEQ ID NO: 2 in order to exhibit a promotion of peptidyl transfer by an EF-P protein and a promotion of accommodation by an EF-Tu protein.

The tRNA of the present invention is preferably a chimera of tRNA$^{Pro1}$ and tRNA$^{GluE2}$ and such a tRNA will hereinafter be called "tRNA$^{Pro1E2}$".

More specifically, tRNA$^{Pro1}$ has preferably the T-stem of tRNA$^{GluE2}$ introduced therein.

Using tRNA$^{Pro1E2}$ pre-charged with a non-proteinogenic amino acid such as D-amino acid or β-amino acid and an EF-P protein in combination enables enhancement of the expression level of not only a linear peptide but also a peptide containing such non-proteinogenic amino acids consecutively, for example, four or five consecutive non-proteinogenic amino acids.

In the tRNA to be used in the present invention, a base sequence other than SEQ ID NO: 1 and/or SEQ ID NO: 2 may be a sequence derived from a wild type tRNA or a sequence derived from a wild type tRNA derived from an *Escherichia coli*, or it may be an artificial tRNA prepared by in vitro transcription.

In the present invention, the translation system contains the tRNA of the present invention and because of containing the tRNA, this system is capable of synthesizing a peptide having amino acids generally difficult to be consecutively introduced consecutively bonded to each other. More specifically, it is a translation system capable of synthesizing a peptide having two or more non-proteinogenic amino acids consecutively bound to each other.

The translation system is not particularly limited insofar as it contains the tRNA of the present invention and it contains a component to be used in a cell-free translation system.

The translation system preferably contains an EF-P protein, and more preferably it further contains an EF-Tu protein.

In the translation system of the present invention, codon reassignment making use of a flexizyme is performed by assigning a non-proteinogenic amino acid to a codon selected as needed as NNN.

In the translation system of the present invention, a natural translation system may be used. In the natural translation system, a tRNA having an anticodon corresponding to each amino acid is present and the tRNA has an intrinsic sequence even in a region other than an anticodon loop.

In the present invention, insofar as the base sequence represented by SEQ ID NO: 1 and/or SEQ ID NO: 2 is introduced, base sequences of an acceptor stem, an anticodon stem, an anticodon loop, or a variable loop may be arbitrary in the sense that a sequence intrinsic to tRNA in such natural translation system can be assigned as another sequence.

In the translation system of the present invention, an arbitrary amino acid may be reassigned to all the NNNs (N represents an arbitrary base) by making use of a flexizyme and in this case, all the tRNAs may be artificial. In this case, elongator tRNAs corresponding to each NNN to be added to the translation system may have, as 85% or more or 90% or more of the full length thereof, the same base sequence.

Alternatively, a group of elongator tRNAs having almost the same sequences except the sequence of an anticodon can be used.

The term "anticodon loop" as used herein means a loop portion of a single strand of tRNA including an anticodon. The sequence of the anticodon loop can be determined as needed by those skilled in the art so as to complement the codon-anticodon interaction.

Translation of a peptide in a known cell-free translation system by using the tRNA of the present invention enables synthesis of a peptide having two or more consecutive non-proteinogenic amino acids therein.

The cell-free translation system used above is not particularly limited.

The method of constructing a peptide library can provide a library more abundant in variety because peptides containing a non-proteinogenic amino acid encoded by an appropriate codon and having two or more consecutive non-proteinogenic amino acids can be produced or peptides having two or more non-proteinogenic amino acids can be produced efficiently.

Provided in the present invention is a method of constructing a peptide library including:

a step of preparing an mRNA library containing mRNAs encoding each peptide of the peptide library, the mRNAs each containing one or more NNNs encoding a non-proteinogenic amino acid; and a step of translating the mRNAs of the mRNA library in a cell-free translation system having therein a tRNA having an anticodon corresponding to any of the codons of NNN and charged with a non-proteinogenic amino acid corresponding to the codon.

In the present invention, a method of constructing a peptide-mRNA complex library is performed by binding puromycin to the downstream region of ORF (Open reading frame) of each of the mRNAs upon preparation of the mRNA library in the above-described method of constructing a peptide library. Puromycin may be bound to the mRNA via a linker composed of a peptide or a nucleic acid. By binding puromycin to the downstream region of ORF of the mRNA, a ribosome that has translated the ORF of the mRNA incorporates puromycin therein to form an mRNA-peptide complex. Such a peptide-mRNA complex can link genotype to phenotype and can be applied to in vitro display.

In the present invention, first, NNN to which a non-proteinogenic amino acid is assigned is selected and a tRNA having an anticodon of the NNN in an anticodon loop and encoding the non-proteinogenic amino acid is prepared using a flexizyme or the like.

Then, by preparing and translating an mRNA library in which each mRNA contains one or more NNNs encoding a non-proteinogenic amino acid, a peptide containing the assigned non-proteinogenic amino acid(s) can be expressed.

The term "NNN" as used herein means a codon specifying an amino acid and three Ns forming the codon are each independently selected from adenine (A), guanine (G), cytosine (C), and uracil (U). A mRNA may contain a plurality of NNNs encoding a non-proteinogenic amino acid.

In the present invention, an arbitrary amino acid may be reassigned to NNN not encoding a non-proteinogenic amino acid or a codon-amino acid relation based on a natural genetic code may be used.

In reassignment, an amino acid having a codon-amino acid relation different from that in a natural genetic code table or that having the same relation may be assigned.

The term "natural genetic code table" means a table showing amino acids assigned to an mRNA triplet (codon) in a living body and it is shown in the following Table 1.

TABLE 1

| | | Second letter base | | | | | | | | |
|---|---|---|---|---|---|---|---|---|---|---|
| | | U | | C | | A | | G | | |
| | | Codon | Amino Acid | Codon | Amino Acid | Codon | Amino Acid | Codon | Amino Acid | |
| First letter base | U | UUU | Phenylalanine | UCU | Serine | UAU | Tyrosine | UGU | Cysteine | U | Third letter base |
| | | UUC | Phenylalanine | UCC | Serine | UAC | Tyrosine | UGC | Cysteine | C | |
| | | UUA | Leucine | UCA | Serine | UAA | Stop | UGA | Stop | A | |
| | | UUG | Leucine | UCG | Serine | UAG | Stop | UGG | Tryptophan | G | |
| | C | CUU | Leucine | CCU | Proline | CAU | Histidine | CGU | Arginine | U | |
| | | CUC | Leucine | CCC | Proline | CAC | Histidine | CGC | Arginine | C | |
| | | CUA | Leucine | CCA | Proline | CAA | Glutamine | CGA | Arginine | A | |
| | | CUG | Leucine | CCG | Proline | CAG | Glutamine | CGG | Arginine | G | |
| | A | AUU | Isoleucine | ACU | Threonine | AAU | Asparagine | AGU | Serine | U | |
| | | AUC | Isoleucine | ACC | Threonine | AAC | Asparagine | AGC | Serine | C | |
| | | AUA | Isoleucine | ACA | Threonine | AAA | Lysine | AGA | Arginine | A | |
| | | AUG | Methionine | ACG | Threonine | AAG | Lysine | AGG | Arginine | G | |
| | G | GUU | Valine | GCU | Alanine | GAU | Aspartic acid | GGU | Glycine | U | |
| | | GUC | Valine | GCC | Alanine | GAC | Aspartic acid | GGC | Glycine | C | |
| | | GUA | Valine | GCA | Alanine | GAA | Glutamic acid | GGA | Glycine | A | |
| | | GUG | Valine | GCG | Alanine | GAG | Glutamic acid | GGG | Glycine | G | |

Assignment of an amino acid different from that of the natural genetic code table to each codon is achieved by codon reassignment making use of, for example, an artificial aminoacylation ribozyme flexizyme (Flexizyme). Using the flexizyme enables aminoacylation of a desired amino acid on a tRNA having an arbitrary anticodon, so that an arbitrary amino acid can be assigned to an arbitrary codon.

The term "amino acid" as used herein embraces, in addition to proteinogenic amino acids, artificial amino acid mutants or derivatives. Examples include proteinogenic L-amino acids and compounds obtained by chemical synthesis and having properties known per se in the art as characteristics of amino acids.

When the proteinogenic amino acids (proteinogenic amino acids) are represented by a three-letter code known per se in the art, they are Arg, His, Lys, Asp, Glu, Ser, Thr, Asn, Gln, Cys, Gly, Pro, Ala, Ile, Leu, Met, Phe, Trp, Tyr, and Val.

The term "non-proteinogenic amino acids" (non-proteinogenic amino acids) means natural or unnatural amino acids other than the proteinogenic amino acids.

Examples of the unnatural amino acids include α,α-disubstituted amino acids (such as α-methylalanine), N-alkyl-α-amino acids, D-amino acids, β-amino acids, and α-hydroxy acids, each of which has a main chain structure different from that of natural amino acids; amino acids having a side chain structure different from that of natural amino acids (such as norleucine and homohistidine); amino acids having extra methylene in a side chain thereof (such as "homo"amino acids, homophenylalanine, and homohistidine); and amino acids obtained by substituting a carboxylic acid functional group in a side chain thereof by a sulfonic acid group (such as cysteic acid). Specific examples of the unnatural amino acid include amino acids described in WO2015/030014.

The non-proteinogenic amino acid is preferably a D-amino acid, a β-amino acid, or an α,α-disubstituted amino acid, with a D-amino acid or a β-amino acid being more preferred.

In the present invention, a peptide library including $1 \times 10^6$ or more kinds of peptides can be constructed.

The number of amino acids contained in each peptide and encoded by NNN is not particularly limited insofar as a non-proteinogenic amino acid is contained and it can be set at, for example, 4, 5, 6, 7, 8, 9, 10, 15, 20, 30, or the like. The position of NNN encoding a non-proteinogenic amino acid in each mRNA is not particularly limited and by using the tRNA of the present invention, a peptide having non-proteinogenic amino acids consecutively arranged therein is translated at the same level with library synthesis of proteinogenic amino acids, even from an mRNA in which NNNs encoding a non-proteinogenic amino acid are consecutively arranged.

Codon reassignment can make use of a translation system constructed by arbitrarily removing a component of a translation system according to the purpose and reconstituting only the necessary components. For example, when a translation system excluding a specific amino acid is reconstituted, a codon corresponding to the amino acid becomes an empty codon encoding no amino acid. When an arbitrary amino acid is linked to a tRNA having an anticodon complementary to the empty codon by making use of a flexizyme or the like, the linked product is added and translation is performed, the arbitrary amino acid is encoded by the codon and a peptide having the arbitrary amino acid introduced therein instead of the excluded amino acid is translated.

The term "cell-free translation system" as used herein means a translation system not containing cells. As the cell-free translation system, for example, an *Escherichia coli* extract, a wheat germ extract, a rabbit reticulocyte extract, or an insect cell extract can be used. A re-constituted type cell-free translation system may be used, which is constructed by reconstituting a ribosomal protein, aminoacyl-tRNA synthetase (aaRS), ribosomal RNA, amino acid, rRNA, GTP, ATP, translation initiation factor (IF), elongation factor (EF), release factor (RF), and ribosome recycling factor (RRF), each of which is purified, and other factor(s) necessary for translation.

The system may contain RNA polymerase for performing transcription from DNA simultaneously. Examples of a commercially available cell-free translation system include *Escherichia-coli* derived systems such as "RTS-100" (Registered trade mark) of Roche Diagnostics, reconstituted translation systems such as "PURESYSTEM" (Registered trade mark) of PGI and "PURExpressR In Vitro Protein Synthesis Kit" and the like of New England Biolabs, and systems using a wheat germ extract such as those of ZOEGENE Corporation and CellFree Sciences.

As a system using a ribosome of *Escherichia coli*, for example, a technology described in the following documents is known: H. F. Kung et al., 1977. The Journal of Biological Chemistry Vol. 252, No. 19, 6889-6894; M. C. Gonza et al., 1985, Proceeding of National Academy of Sciences of the United States of America Vol. 82, 1648-1652; M. Y. Pavlov and M. Ehrenberg, 1996, Archives of Biochemistry and Biophysics Vol. 328, No. 1, 9-16; Y. Shimizu et al., 2001, Nature Biotechnology Vol. 19, No. 8, 751-755; H. Ohashi et al., 2007, Biochemical and Biophysical Research Communications Vol. 352, No. 1, 270-276.

The cell-free translation system can provide a high-purity expression product without purification.

It is to be noted that the cell-free translation system of the present invention may be used not only for the translation but also for transcription after addition of a necessary component for transcription.

The peptide obtained in the present invention may be a cyclic peptide. It may be, for example, a cyclic peptide cyclized in combination of an amino acid having a functional group 1 and an amino acid having a functional group 2 corresponding thereto, each shown below in Table 1.

Either of the functional group 1 or 2 may be placed on the N terminal side; they may be placed at the N terminal and the C terminal, respectively; one of them may be a terminal amino acid and the other one may be a non-terminal amino acid; or both may be a non-terminal amino acid.

A linkage formed between the functional group 1 and the functional group 2 is said to be a chemical crosslinking structure for forming a molecular cyclic structure of a cyclic peptide.

TABLE 2

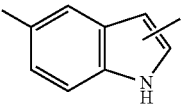

In the formulas, $X_1$ represents a leaving group and examples of the leaving group include halogen atoms such as Cl, Br, and I and Ar represents a substituted or unsubstituted aromatic ring.

As an amino acid having the functional group of (A-1), for example, a chloroacetylated amino acid can be used. Examples of the chloroacetylated amino acid include N-chloroacetyl-L-alanine, N-chloroacetyl-L-phenylalanine, N-chloroacetyl-L-tyrosine, N-chloroacetyl-L-tryptophan, N-3-(2-chloroacetamido)benzoyl-L-phenylalanine, N-3-(2-chloroacetamido)benzoyl-L-tyrosine, N-3-(2-chloroacetamido)benzoyl-L-tryptophan, β-N-chloroacetyl-L-diaminopropanoic acid, γ-N-chloroacetyl-L-diaminobutyric acid, δ-N-chloroacetyl-L-ornithine, and ε-N-chloroacetyl-L-lysine, and D-amino acid derivatives corresponding thereto.

As the amino acid having the functional group of (A-1), N-chloroacetyl-L-tryptophan and N-chloroacetyl-L-tyrosine are preferred, with D-forms being more preferred.

The present specification sometimes clearly describes that the amino acid used is an L-form, but it may be either an L-form or a D-form, or it may be a mixture, at any ratio, of an L-form and a D-form. Even when the present specification does not clearly describe that the amino acid used is an L-form or a D-form, it means that it may be either an L-form or a D-form, or it may be a mixture, at any ratio, of an L-form and a D-form.

Examples of an amino acid having the functional group (A-2) include cysteine, homocysteine, mercaptonorvaline, mercaptonorleucine, 2-amino-7-mercaptoheptanoic acid, and 2-amino-8-mercaptooctanoic acid.

As the amino acid having the functional group (A-2), cysteine is preferred.

Examples of a cyclization method with the amino acid having the functional group (A-1) and the amino acid having the functional group (A-2) include the methods described, for example, in Kawakami, T. et al., Nature Chemical Biology 5, 888-890 (2009); Yamagishi, Y. et al., ChemBioChem 10, 1469-1472 (2009); Sako, Y. et al., Journal of American Chemical Society 130, 7932-7934 (2008); Goto, Y. et al., ACS Chemical Biology 3, 120-129 (2008); and Kawakami T. et al, Chemistry & Biology 15, 32-42 (2008), and WO2008/117833.

As an amino acid having the functional group (B-1), for example, propargylglycine, homopropargylglycine, 2-amino-6-heptynoic acid, 2-amino-7-octynoic acid, and 2-amino-8-nonynoic acid can be used.

A 4-pentynoylated or 5-hexynoylated amino acid may also be used.

Examples of the 4-pentynoylated amino acid include N-(4-pentenoyl)-L-alanine, N-(4-pentenoyl)-L-phenylalanine, N-(4-pentenoyl)-L-tyrosine, N-(4-pentenoyl)-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophan, β-N-(4-pentenoyl)-L-diaminopropanoic acid, γ-N-(4-pentenoyl)-L-diaminobutyric acid, σ-N-(4-pentenoyl)-L-ornithine, and ε-N-(4-pentenoyl)-L-lysine, and D-amino acid derivatives corresponding thereto.

Examples of the 5-hexynolated amino acid include amino acids obtained by substituting the 4-pentynol group, of the compounds exemplified as the 4-pentynolated amino acid, by a 5-hexynol group.

Examples of an amino acid having the functional group (B-2) include azidoalanine, 2-amino-4-azidobutanoic acid, azidoptonovaline, azidonorleucine, 2-amino-7-azidoheptanoic acid, and 2-amino-8-azidooctanoic acid.

An azidoacetylated or 3-azidopentanoylated amino acid can also be used.

Examples of the azidoacetylated amino acid include N-azidoacetyl-L-alanine, N-azidoacetyl-L-phenylalanine, N-azidoacetyl-L-tyrosine, N-azidoacetyl-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophan, β-N-azidoacetyl-L-diaminopropanoic acid, γ-N-azidoacetyl-L-diaminobutyric acid, σ-N-azidoacetyl-L-ornithine, and ε-N-azidoacetyl-L-lysine, and D-amino acid derivatives corresponding thereto.

Examples of the 3-azidopentanoylated amino acid include amino acids obtained by substituting the azidoacetyl group of, the compounds exemplified as the azidoacetylated amino acid, by a 3-azidopentanoyl group.

Examples of a cyclization method with the amino acid having the functional group (B-1) and the amino acid having the functional group (B-2) include the methods described, for example, in Sako, Y. et al., Journal of American Chemical Society 130, 7932-7934 (2008) and WO2008/117833.

Examples of an amino acid having the functional group (C-1) include N-(4-aminomethyl-benzoyl)-phenylalanine (AMBF) and 3-aminomethyltyrosine.

Examples of an amino acid having the functional group (C-2) include 5-hydroxytryptophan (WOH).

Examples of a cyclization method with the amino acid having the functional group (C-1) and the amino acid having the functional group (C-2) include the method described, for example, in Yamagishi, Y. et al., ChemBioChem 10, 1469-1472 (2009) and WO2008/117833.

Examples of an amino acid having the functional group (D-1) include 2-amino-6-chloro-hexynoic acid, 2-amino-7-chloro-heptynoic acid, and 2-amino-8-chloro-octynoic acid.

Examples of an amino acid having the functional group (D-2) include cysteine, homocysteine, mercaptonorvaline, mercaptonorleucine, 2-amino-7-mercaptoheptanoic acid, and 2-amino-8-mercaptooctanoic acid.

Examples of a cyclization method with the amino acid having the functional group (D-1) and the amino acid having the functional group (D-2) include the method described, for example, in WO2012/074129.

Examples of an amino acid (E-1) include N-3-chloromethylbenzoyl-L-phenylalanine, N-3-chloromethylbenzoyl-L-tyrosine, and N-3-chloromethylbenzoyl-L-tryptophan, and D-amino acid derivatives corresponding thereto.

Examples of an amino acid (E-2) include cysteine, homocysteine, mercaptonorvaline, mercaptonorleucine, 2-amino-7-mercaptoheptanoic acid, and 2-amino-8-mercaptooctanoic acid.

A cyclization method with the amino acid having the functional group (E-1) and the amino acid having the functional group (E-2) can be performed with reference to, for example, the cyclization method with the (A-1) and (A-2) or the cyclization method with the (D-1) and (D-2).

The ring-forming amino acid is preferably a combination of the amino acid having the functional group (A-1) and the amino acid having the functional group (A-2), more preferably a combination of N-acetyltryptophan having a leaving group instead of H thereof and cysteine, much more preferably a combination of N-haloacetyl-D-tyrosine or N-haloacetyl-D-tryptophan, with N-chloroacetyl-D-tyrosine or N-chloroacetyl-D-tryptophan being more preferred, and cysteine (Cys).

The present invention also provides a peptide library or a peptide-mRNA complex library.

Construction of a peptide library with the tRNA of the present invention facilitates synthesis of a peptide containing a non-proteinogenic amino acid on almost an equal expression level to that of a peptide composed of an L-amino acid. Therefore, compared with a conventional peptide library, a peptide library abundant in variety in terms of the introduction of a non-proteinogenic amino acid can be obtained.

Above all, a library including a peptide having two or more consecutive non-proteinogenic amino acids can be obtained.

Construction of a peptide-mRNA complex library with the tRNA of the present invention facilitates synthesis of a peptide containing a non-proteinogenic amino acid on almost an equal expression level to that of a peptide composed of an L-amino acid. Therefore, compared with a conventional peptide-mRNA complex library, a peptide-mRNA complex library abundant in variety in terms of the introduction of a non-proteinogenic amino acid can be obtained.

Above all, a library including a peptide having two or more consecutive non-proteinogenic amino acids can be obtained.

In the present invention, a peptide library and a peptide-mRNA complex library having, as a peptide structure thereof, a structure having four or more consecutive non-proteinogenic amino acids and intramolecularly crosslinked between non-proteinogenic amino acids can be obtained.

For intramolecular crosslinking between non-proteinogenic amino acids in a structure having four or more consecutive non-proteinogenic amino acids, the intramolecular crosslink can be constructed by making use of non-proteinogenic amino acids used upon translation in a cell-free translation system and cyclization.

Preferred examples include a disulfide bond between D-cysteine and D-cysteine and a thioether bond between a non-proteinogenic amino acid having a ClAc group introduced therein and D-cysteine.

The present invention also provides a screening method using the peptide library constructed using the tRNA of the present invention, for identifying a peptide which binds to a target substance.

The screening method includes a step of bringing the peptide library constructed using the tRNA of the present invention into contact with a target substance and incubating the resulting mixture.

The target substance is not particularly limited herein and low molecular compounds, high molecular compounds, nucleic acids, peptides, proteins, sugars, and lipids can be used.

The screening method further includes a step of selecting a peptide bound to the target substance. The peptide bound to the target substance is selected, for example, by labeling peptides detectably by a known method and after the above-described step of bringing them into contact, washing a surface of a solid phase carrier with a buffer, and detecting a compound bound to the target substance.

Examples of the detectable label include enzymes such as peroxidase and alkaline phosphatase, radioactive substances such as 125I, 131I, 35S, and 3H, fluorescent substances such as fluorescein isothiocyanate, rhodamine, dansyl chloride, phycoerythrin and tetramethyl rhodamine isothiocyanate, and near infrared fluorescent materials, light-emitting substances such as luciferase, luciferin, and aequorin, and nanoparticles such as gold colloid and quantum dot. When the enzyme is used, detection can be achieved by adding a substrate of the enzyme to develop a color. Detection can also be achieved by binding biotin to a peptide and then binding avidin or streptavidin labeled with the enzyme or the like to the biotin-bound peptide.

Screening using the peptide-mRNA complex library can be carried out by applying the TRAP display method.

In this case, after the peptide-mRNA complex library is subjected to a reverse transcription reaction, the resulting library is brought into contact with a target substance. A complex that binds to the target substance is selected and its DNA is amplified by PCR. By adding the resulting DNA to a TRAP reaction system, a peptide-mRNA complex library is constructed again. A similar operation is repeated.

Since this concentrates the peptide-mRNA complex having high affinity for the target substance, a peptide that binds to the target substance can be identified efficiently by analyzing the DNA sequence of the concentrated complex.

Disclosure of all the Non-Patent Documents and Reference Literatures cited herein is incorporated herein by reference in their entirety.

EXAMPLES

The present invention will hereinafter be described in detail by Examples but the present invention is not limited to them. The present invention can be changed by those skilled in the art into various modes without departing from the significance of the present invention and such a change is also embraced within the scope of the present invention.
Preparation of flexizyme and tRNA A flexizyme (dFx or eFx) and tRNA (shown in Table 3) used for pre-charging D-amino acid, β-amino acid, 2-aminoisobutyric acid, and L-proline were transcribed by T7 RNA polymerase in vitro.

A template DNA having a T7 promoter before a flexizyme (dFx or eFx) or tRNA sequence was prepared by extension of a pair of forward and reverse extension primers (shown in Table 4) and then, PCR was performed using a pair of forward and reverse extension primers (shown in Table 5).

TABLE 3

| RNA name | RNA sequence |
| --- | --- |
| dFx | GGAUCGAAAGAUUUCCGCAUCCCCGAAAGGGUACAUGGCGUUAGGU |
| eFx | GGAUCGAAAGAUUUCCGCGGCCCCGAAAGGGGAUUAGCGUUAGGU |
| tRNA, Pro1 (CGG) | CGGUGAUUGGCGCAGCCUGGUAGCGCACUUCGUUCGGGACGAAGGGGUCGGAGGUUCGAAUCCUCUAUCACCGACCA |
| tRNA, Pro1 (GGU) | CGGUGAUUGGCGCAGCCUGGUAGCGCACUUCGUUGGUAACGAAGGGGUCGGAGGUUCGAAUCCUCUAUCACCGACCA |
| tRNA, Pro1 (GUG) | CGGUGAUUGGCGCAGCCUGGUAGCGCACUUCGUUGUGAACGAAGGGGUCGGAGGUUCGAAUCCUCUAUCACCGACCA |
| tRNA, Pro1C13G (CGG) | CGGUGAUUGGCGGAGCCUGGUAGCGCACUUCGUUCGGGACGAAGGGGUCGGAGGUUCGAAUCCUCUAUCACCGACCA |
| tRNA, Pro1E1 (CGG) | CGGUGAUUGGCGCAGCCUGGUAGCGCACUUCGUUCGGGACGAAGGGUCAGGGGUUCGAAUCCCCUAUCACCGACCA |
| tRNA, Pro1E2 (CGG) | GGGUGAUUGGCGCAGCCUGGUAGCGCACUUCGUUCGGGACGAAGGGUCAGGGGUUCGAAUCCCCUAUCACCCGCCA |

TABLE 3-continued

| RNA name | RNA sequence |
|---|---|
| tRNA, ProlE2 (GAU) | GGGUGAUUGGCGCAGCCUGGUAGCGCACUUCGCUGAUAACGAAGGGGUCAGGGGUUCGAAUCCCCUAUCACCCGCCA |
| tRNA, ProlE2 (GGU) | GGGUGAUUGGCGCAGCCUGGUAGCGCACUUCGUUGGUAACGAAGGGGUCAGGGGUUCGAAUCCCCUAUCACCCGCCA |
| tRNA, ProlE2 (GUG) | GGGUGAUUGGCGCAGCCUGGUAGCGCACUUCGUUGUGAACGAAGGGGUCAGGGGUUCGAAUCCCCUAUCACCCGCCA |
| tRNA, GluE2 (CGG) | GUCCCCUUCGUCUAGAGGCCCAGGACACCGCCUUCGGGAGGCGGUAACAGGGGUUCGAAUCCCCUAGGGGACGCCA |
| tRNA, AsnE2 (CGG) | GGCUCUGUAGUUCAGUCGGUAGAACGGCGGAUUCGGGAUCCGUAUGUCACUGGUUCGAGUCCAGUCAGAGCCGCCA |
| tRNA, fMet (CAU) | CGCGGGGUGGAGCAGCCUGGUAGCUCGUCGGGCUCAUAACCCGAAGAUCGUCGGUUCAAAUCCGGCCCCCGCAACCA |

The sequences in Table 3 from top to bottom are SEQ ID NOs: 8-21, respectively.

TABLE 4

| RNA name | Extension primer (forward) | Extension primer (reverse) |
|---|---|---|
| dFX | GTAATACGACTCACTATAGGATCGAAAGATTTCCGC | ACCTAACGCCATGTACCCTTTCGGGGATGCGGAAATCTTTCGATCC |
| eFx | GTAATACGACTCACTATAGGATCGAAAGATTTCCGC | ACCTAACGCTAATCCCCTTTCGGGGCCGCGGAAATCTTTCGATCC |
| tRNA, Pro1 (CGG) | GTAATACGACTCACTATACGGTGATTGGCGCAGCCTGGTAGCGCACTTCGTCGGGACG | TGGTCGGTGATAGAGGATTCGAACCTCCGACCCCTTCGTCCCGAACGAAGTGC |
| tRNA, Pro1 (GGU) | GTAATACGACTCACTATAAGGGTGATTGGCGCAGCCTGGTAGCGCACTTCG | TGGTCGGTGATAGAGGATTCGAACCTCCGACCCCTTCGTTACCAACGAAGTGCGCTACCAGG |
| tRNA, Pro1 GUG) | GTAATACGACTCACTATAAGGGTGATTGGCGCAGCCTGGTAGCGCACTTCG | TGGTCGGTGATAGAGGATTCGAACCTCCGACCCCTTCGTTCACAACGAAGTGCGCTACCAGG |
| tRNA, Pro1C13G (CGG) | GTAATACGACTCACTATACGGTGATTGGCGCGGAGCCTGGTAGCGCACTTCGTCGGGACG | TGGTCGGTGATAGAGGATTCGAACCTCCGACCCCTTCGTCCCGAACGAAGTGC |
| tRNA, Pro1E1 (CGG) | GTAATACGACTCACTATACGGTGATTGGCGCAGCCTGGTAGCGCACTTCG | TGGTCGGTGATAGGGATTCGAACCCCTGACCCCTTCGTCCCGAACGAAGTGCGCTACCAGG |
| tRNA, Pro1E2 (CGG) | GTAATACGACTCACTATAAGGGTGATTGGCGCAGCCTGGTAGCGCACTTCG | TGGCGGGTGATAGGGGATTCGAACCCCTGACCCCTTCGTCCCGAACGAAGTGCGCTACCAGG |
| tRNA, Pro1E2 (GAU) | GTAATACGACTCACTATAAGGGTGATTGGCGCAGCCTGGTAGCGCACTTCG | TGGCGGGTGATAGAGGATTCGAACCTCCGACCCCTTCGTTATCAGCGAAGTGCGCTACCAGG |
| tRNA, Pro1E2 (GGU) | GTAATACGACTCACTATAGGGGTGATTGGCGCAGCCTGGTAGCGCACTTCG | TGGCGGGTGATAGAGGATTCGAACCTCCGACCCCTTCGTTACCAACGAAGTGCGCTACCAGG |
| tRNA, Pro1E2 (GUG) | GTAATACGACTCACTATAAGGGTGATTGGCGCAGCCTGGTAGCGCACTTCG | TGGCGGGTGATAGAGGATTCGAACCTCCGACCCCTTCGTTCACAACGAAGTGCGCTACCAGG |
| tRNA, GluE2 (CGG) | CACTATAGTCCCCTTCGTCTAGAGGCCCAGGACACCGCCTTCGGGAGGCGGTAACAGGGGTTCG | TGGCGTCCCCTAGGGATTCGAACCCCTGTTACCGCC |
| tRNA, AsnE2 (CGG) | GTAATACGACTCACTATAAGGCTCTGTAGTTCAGTCGGTAGAACGGCGGA | TGGCGGCTCTGACTGGACTCGAACCAGTGACATACGGATCCCGAATCCGCCGTTCTACCGACTG |
| tRNA, fMet (CAU) | GTAATACGACTCACTATAACGCGGGGTGGAGCAGCCTGGTAGCTCGTCGGGCTCATAACCCGAAGATCG | TGGTTGCGGGGCCGGATTTGAACCGACGATCTTCGGGTTATGAGC |

The sequences in Table 4 (center column) from top to bottom are SEQ ID NOs: 22-35, respectively. The sequences in Table 4 (right column) from top to bottom are SEQ ID NOs: 36-49, respectively.

TABLE 5

| RNA name | PCR primer (forward) | PCR primer (reverse) |
|---|---|---|
| dFx | GGCGTAATACGACTCACTATAG | ACCTAACGCCATGTACCCT |
| eFx | GGCGTAATACGACTCACTATAG | ACCTAACGCTAATCCCCT |
| tRNA, Pro1 (CGG) | GGCGTAATACGACTCACTATAC | TGmGTCGGTGATAGAGGATTC |
| tRNA, Pro1 (GGU) | GGCGTAATACGACTCACTATAC | TGmGTCGGTGATAGAGGATTC |
| tRNA, Pro1 (GUG) | GGCGTAATACGACTCACTATAC | TGmGTCGGTGATAGAGGATTC |
| tRNA, Pro1C13G (CGG) | GGCGTAATACGACTCACTATAC | TGmGTCGGTGATAGAGGATTC |
| tRNA, Pro1E1 (CGG) | GGCGTAATACGACTCACTATAC | TGmGTCGGTGATAGGGGATTC |
| tRNA, Pro1E2 (CGG) | GGCGTAATACGACTCACTATAG | TGmGCGGGTGATAGGGGATTC |
| tRNA, Pro1E2 (GAU) | GGCGTAATACGACTCACTATAG | TGmGCGGGTGATAGGGGATTC |
| tRNA, Pro1E2 (GGU) | GGCGTAATACGACTCACTATAG | TGmGCGGGTGATAGGGGATTC |
| tRNA, Pro1E2 (GUG) | GGCGTAATACGACTCACTATAG | TGmGCGGGTGATAGGGGATTC |
| tRNA, GluE2 (CGG) | GTAATACGACTCACTATAGTCCCCTTCGTCTAG | TGmGCGTCCCCTAGGGATTC |

TABLE 5-continued

| RNA name | PCR primer (forward) | PCR primer (reverse) |
| --- | --- | --- |
| tRNA, AsnE2 (CGG) | GTAATACGACTCACTAT AG | TGmGCGGCTCTGACTG GAC |
| tRNA, fMet (CAU) | GGCGTAATACGACTCAC TATAC | TGmGTTGCGGGGGCCG GA |

The sequences in Table 5 (center column) from top to bottom are SEQ ID NOs: 50-63, respectively. The sequences in Table 4 (right column) from top to bottom are SEQ ID NOs: 64-77, respectively.

In Table 5, Gm represents 2'-O-methylguanosine.

The PCR product was subjected to phenol/chloroform extraction and ethanol precipitation, and then used for transcription at 37° C. for 16 hours in 250 μL of a reaction mixture containing 40 mM Tris-HCl (pH 8.0), 22.5 mM MgCl$_2$, 1 mM DTT, 1 mM spermidine, 0.01% Tripton X-100, 120 nM T7 RNA polymerase, 0.04 U/μL RNasin RNase inhibitor (Promega) and 3.75 mM NTP mix.

In preparing tRNA, 5 mM GMP or CMP was added to the above-described solution, depending on the nucleotide at the 5' end (G or C). The resulting RNA transcript was treated with RQ1 DNase (Promega) at 37° C. for 30 minutes and then purified by 8% (tRNA) or 12% (flexizyme) polyacrylamide gel containing 6 M urea.

Aminoacylation of tRNA

After a D-amino acid and a β-amino acid were pre-activated as 3,5-dinitrobenzyl ester (DBE) or cyanomethyl ester (CME), the tRNA was charged with the resulting amino acid by using an appropriate flexizyme (dFx for DBE activated amino acid, eFx for CME activated amino acid).

D-alanine, D-serine, and D-cysteine, L-β-homoglutamine (βhQ), L-β-homomethionine (βhM), L-β-homophenylglycine (βhF), L-proline, and 2-aminobutyric acid (Aib) were DBE-activated, while chloroacetyl D-phenylalanine (D-$^{ClAc}$Phe) was CME activated. The above-described activated amino acids were synthesized according to the method described in Non-Patent Document 1 and Reference Literature 18.

The flexizyme reaction (aminoacylation) was performed at 0° C. in a reaction mixture containing 50 mM HEPES-KOH (pH 7.5 for the D-amino acid, pH 8.7 for the β-amino acid), 600 mM MgCl$_2$, 20% DMSO, 25 μM dFx or eFx, 25 μM tRNA, and 5 mM activated amino acid.

The eFx was used for D-$^{ClAc}$Phe-CME, while the dFx was used for the other amino acids. The reaction was carried out for 2 hours for D-Ala, D-$^{ClAc}$Phe, L-Pro, and Aib; 6 hours for D-Ser and D-Cys; and 22 hours for the β-amino acid. The aminoacyl-tRNA was collected by ethanol precipitation. The pellet was then washed twice with 70% ethanol containing sodium acetate (pH 5.2) and once with 70% ethanol and dissolved in 1 mM sodium acetate (pH 5.2).

Preparation of EF-P

An *E. coli* EF-P gene was cloned into a modified pET28a vector having a PreScission protease recognition site instead of a thrombin site. *E. coli* EpmA and EpmB genes were cloned into a pETDuet-1 vector. The resulting vectors were co-introduced into *E. coli* Rosetta2 (DE3). The cells were cultured at 37° C. for 2 hours in an LB medium containing 0.5 mM IPTG and lysed by ultrasonication. The cell lysate was applied to a Ni-NTA column and histidine labeled EF-P was purified. The column was washed with a buffer A (20 mM Tris-HCl (pH 8.0), 200 mM NaCl, 2 mM imidazole, and 1 mM 2-mercaptoethanol) and the histidine-labeled EF-P was eluted by the buffer A containing 300 mM imidazole. Turbo3C protease was added to the eluate to cleave a histidine tag, followed by dialysis overnight at 4° C. against the buffer A. The sample was applied to a Ni-NTA column and the flow-through and the washing fraction were collected as EF-P without a histidine tag. Then, the protein was concentrated through Amicon ultra 10 k centrifugal filter (Merck Millipore). The modification of EF-P was confirmed by mass spectrometric analysis described in Reference Literature 3.

Translation and Quantification of Model Peptide

The translation of a model peptide was performed in a modified FIT (Flexible in vitro translation) system in which the concentrations of IF2, EF-G, and EF-Tu/Ts (3, 0.1, and 20 μM, respectively) were optimized for incorporation of a D-amino acid and a β-amino acid (refer to Non-Patent Document 5).

The modified FIT system has the following constitution: 50 mM HEPES-KOH (pH7.6), 100 mM potassium acetate, 12.3 mM magnesium acetate, 2 mM ATP, 2 mM GTP, 1 mM CTP, 1 mM UTP, 20 mM creatine phosphoric acid, 0.1 mM 10-formyl-5,6,7,8-tetrahydrofolic acid, 2 mM spermidine, 1 mM DTT, 1.5 mg/mL *E. coli* total tRNA, 1.2 μM *E. coli* ribosome, 0.6 μM methionyl-tRNA formyltransferase, 2.7 μM IF1, 3 μM IF2, 1.5 μM IF3, 0.1 μM EF-G, 20 μM EF-Tu/Ts, 0.25 μM RF2, 0.17 μM RF3, 0.5 μM RRF, 4 μg/mL creatine kinase, 3 μg/mL myokinase, 0.1 μM inorganic pyrophosphatase, 0.1 μM nucleotide diphosphate kinase, 0.1 μM T7 RNA polymerase, 0.13 μM AspRS, 0.11 μM LysRS, 0.03 μM MetRS, 0.02 μM TyrRS, 0.05 mM [$^{14}$C] aspartic acid, 0.5 mM lysine, 0.5 mM methionine, 0.5 mM tyrosine, 25 μM each pre-charged aminoacyl-tRNA, and 0.5 μM DNA template. For the translation of rP1 and rP2 or β-amino acid-containing peptide, 0.09 μM GlyRS and 0.5 mM glycine were added to the above solution.

The translation reaction was made at 37° C. in 2.5 μL of a solution. An equal volume of a stop solution (0.9M Tris-HCl (pH 8.45), 8% SDS, 30% glycerol, and 0.01% xylene cyanol) was added to stop the reaction, followed by incubation at 95° C. for 2 or 3 minutes. Next, the sample was analyzed by autoradiography using 15% tricine SDS-PAGE and Typhoon FLA 7000 (GE Healthcare). A peptide yield was normalized by the intensity of [$^{14}$C]-Asp band.

For MALDI-TOF mass spectrometric analysis, 0.5 mM non-radioactive aspartic acid was added to the above solution instead of [$^{14}$C] aspartic acid. Translation was performed at 37° C. for 20 minutes or 40 minutes, followed by dilution with an equal volume of 2×HBS buffer (100 mM HEPES-KOH (pH 7.6), 300 mM NaCl). Then, the peptide was purified by anti-FLAG M2 affinity gel (Sigma). The reaction mixture was added to 5 μL of gel beads and the mixture was incubated at 25° C. for 30 minutes. The peptide on the gel beads was washed with 25 μL of 1×HBS buffer (50 mM HEPES-KOH (pH 7.6), 150 mM NaCl) and was eluted from the beads by 15 μL of 0.2% trifluoroacetic acid. Then, the peptide was desalted with SPE C-tip (Nikkyo Technos) and eluted by 1.2 μL of 80% acetonitrile which was a 0.5% acetic acid solution containing 50% saturated (R) cyano-4-hydroxycinnamic acid. MALDI-TOF-mass spectrometric analysis was performed in a reflector/positive mode by using ultrafleXtreme (Bruker Daltonics). Peptide Mass Standard II (Bruker Daltonics) was used for external mass calibration.

Essential D-Arm Structure of tRNA$^{Pro1}$ Recognized by EF-P for Promoting Consecutive D-Amino Acid Incorporation The following test was carried out to confirm that the ability of EF-P enhancing a peptidyl transfer (PT) rate in Pro-Pro elongation promoted the slow incorporation of some D-amino acids in a nascent peptide chain.

First, two mRNA constructs (mR1 and mR2) each of which encoded two and three consecutive D-amino acids were prepared (FIG. 2A).

The D-amino acids were pre-charged on a tRNA$^{Pro1}$ derivative having a corresponding anticodon by the flexizyme technology and they were used in the FIT system containing 5 µM EF-P protein in order to synthesize an rP1 peptide or rP2 peptide.

In this particular FIT system, [$^{14}$C]Asp, cold Met, Tyr, Lys, and Gly and ARSs corresponding thereto were added and other amino acids/ARSs pair not encoded by the mRNAs (mR1 and mR2) was omitted. Instead, D-aminoacyl-tRNA was added to assign the D-amino acid at NNN codon. The concentrations of IF-2, EF-Tu, and EF-G were set at 3 µM, 20 µM, and 0.1 µM, respectively, which were values optimized in advance for the consecutive incorporation of the D-amino acids (Non-Patent Documents 2 and 5). A wild type (WT) tRNA$^{Pro1}{}_{CGG}$ has a C/G base pair at positions 13 and 22 located at the end of the D-stem, whereas a mutant tRNA$^{Pro1}{}_{CGG}$ has a C-to-G point mutation at position 13 and disrupts base pair formation (FIG. 2B). EF-P strictly recognized the 9-nt D-loop closed with the stable D-stem structure of 4 base pairs of WT tRNA$^{Pro1}$ and therefore, the C13G mutation decreased the recognition by EF-P. To decode the NNN codon designating a D-amino acid in the mR1 and mR2, tRNA$^{Pro1}{}_{CGG}$ and the C13G mutant as a negative control were used. The anticodon of tRNA$^{Pro1}$ was changed into another one for decoding the target codon (FIG. 2C).

Three respectively different codons (NNN=CCG, ACU, or CAC) for introducing two consecutive D-alanines into an rP1 peptide (rP1-D-Ala$_2$) were tested in the mR1 by using WT D-Ala-tRNA$^{Pro1}$ (FIG. 2C, FIG. 3A).

The peptide thus obtained was separated by tricine-SDS-PAGE and quantified by autoradiography. Addition of EF-P brought an important improvement on the expression level of the rP1 peptide (rP1-D-Ala$_2$) within a similar range (from 0.4 to 0.6 µM) without depending on codons. The apparent level of the enhancement effect however differed depending on codons due to a difference in the background level of EF-P-free D-Ala incorporation (2.6-, 4.7- and 12-fold for CCG, ACU and CAC, respectively). As a result of EF-P enhancement of the consecutive incorporation of L-Pro present at the position of X residues in rP1-L-Pro$_2$ and rP2-L-Pro$_3$ peptides by using L-Pro-tRNA$^{Pro1}$ as a positive control, 1.4- and 22-fold improvement effects were observed, respectively (FIGS. 3B and 3C).

Next, it was studied whether or not EF-P was able to enhance the incorporation of D-Ser, D-Cys and D-His charged onto tRNA$^{Pro1}{}_{CGG}$ suppressing the CCG codon on mR1 (FIG. 2D and FIG. 3D). The enhancement effect was 5.4-, 8.4-, and 2.1-fold, respectively, indicating that EF-P enhanced two consecutive incorporation of these D-amino acids within a range of from 2- to 10-fold. On the other hand, when the C13G mutant of tRNA$^{Pro1}{}_{CGG}$ was used, the EF-P enhancement effect was 2.1-, 2.4-, 3.5- and 0.9-fold for D-Ala, D-Ser, D-Cys and D-His in rP1-D-X$_2$ peptide, respectively and it decreased. Since the absolute expression level was enhanced by 2-fold or more by the use of WT/EF-P over C13G/EF-P, the EF-P effect was definitely observed in each case. Accurate expression of these peptides was confirmed by MALDI-TOF mass spectrometric analysis (FIG. 3E).

Then, an achiral α,α-dimethyl substituted amino acid (Aib, 2-aminobutyric acid) was used (FIG. 2D and FIGS. 3D and 3E).

It has been confirmed that the α,α-disubstitution set a similar situation in the ribosome PT center like a D-amino acid and very low efficiency of consecutive incorporation of Aib was observed. The EF-P enhancement for the incorporation of Aib into rP1-Aib$_2$ peptide was 20-fold by the use of WT tRNA$^{Pro1}$, while that by the C13G mutant was 5-fold. The expression level was enhanced 3-fold or more by the WT/EF-P combination.

Next, three consecutive incorporation of D-Alas and Aibs into the nascent chain of rP2 peptide was studied (FIG. 2E and FIGS. 3D and 3E). The enhancement effect on the incorporation of D-Ala into rP2-D-Ala$_3$ peptide by EF-P was 1.9-fold using WT tRNA$^{Pro1}{}_{CGG}$, while the expression using the C13G mutant was undetectable level even in the presence of EF-P. The enhancement effect by EF-P was 3-fold when rP2-Aib$_3$ was expressed using WT tRNA$^{Pro1}{}_{CGG}$, while no effect was observed when the C13G mutant was used. The above-described results show that EF-P stimulates the expression level of consecutive D-amino acid incorporation.

In addition, the EF-P concentration was titrated as a function of the expression level of rP1-D-Ala$_2$ peptide in the presence of WT D-Ala-tRNA$^{Pro1}{}_{CGG}$ (FIG. 4A). In the titration experiments at 40- and 15-min time points, 5-7 µM EF-P showed the maximum level of rP1-D-Ala$_2$ expression, whereas higher concentrations of EF-P (10 and 15 µM) declined the EF-P effect. In consideration that the concentration of ribosome in the translation system of Examples was 1.2 µM, the optimum concentration of EF-P was about 5-fold of the ribosome concentration.

Time course analysis of the translation of rP1-D-Ala$_2$ peptide was carried out in the presence of EF-P (5 µM) and absence of EF-P. In both conditions, the yield of full-length peptide plateaued in 50 minutes (FIG. 4B). In 50 min, the expression level of rP1-D-Ala$_2$ peptide reached approximately 1 µM in the presence of 5 µM EF-P. Such a concentration was comparable to the expression level of a full-L-peptide containing L-Ala$_2$ (Reference Literature 3).

Engineering of T-Stem Structure of tRNA$^{Pro1}$ for Further Enhancing Consecutive D-Alanine Incorporation The T-stem of tRNA$^{GluE2}$ was introduced into tRNA$^{Pro1}$ to form a chimeric tRNA called herein tRNA$^{Pro1E1}$ (FIG. 5A, tRNA$^{Pro1E1}{}_{CGG}$).

Further, another chimeric tRNA called herein tRNA$^{Pro1E2}{}_{CGG}$ having additional mutation at a discriminator base recognized by ProRS (Reference Literature 9) was formed. Due to introduction of such mutation, tRNA$^{Pro1E2}{}_{CGG}$ was prevented from being charged with Pro by ProRS. This means that it has orthogonality to ProRS.

Ability of incorporating two consecutive D-alanines into rP1-D-Ala$_2$ was compared among WT tRNA$^{Pro1}{}_{CGG}$, tRNA$^{Pro1E1}{}_{CGG}$, tRNA$^{Pro1E2}{}_{CGG}$, tRNA$^{GluE2}{}_{CGG}$, and tRNA$^{AsnE2}{}_{CGG}$ (FIG. 5A) (FIG. 5B and FIG. 6A).

As a result, it was confirmed from comparison with other tested tRNAs that a peptide expression level was enhanced by 4-fold or more by using EF-P with tRNA$^{Pro1E1}{}_{CGG}$ (4.1-fold) or with tRNA$^{Pro1E2}{}_{CGG}$ (5.0-fold) in combination. This clearly means that the chimeric tRNA$^{Pro1E1}$ and tRNA$^{Pro1E2}$ derived from the T-stem of chimeric tRNA$^{GluE2}$ and the D-arm of tRNA$^{Pro1}$ enhance a total PT rate, assisted by EF-P and EF-Tu.

Incorporation of a Plurality of D-Amino Acids Enhanced by EF-P

The combination of D-Ala-tRNA$^{Pro1E2}$ and EF-P enables enhancement of the expression level of rPA-D-Ala$_2$.

Five respectively different template mRNAs were prepared (FIG. 7A, mR3 to mR7) and peptides corresponding thereto containing, in the sequence thereof, one to three respectively different D-amino acids were synthesized (FIG. 7A, rP3 to rP7 peptides).

In these mRNAs, D-Ala-tRNA$^{Pro1E2}_{GAU}$, D-Cys-tRNA$^{Pro1E2}_{GUG}$, and D-Ser-tRNA$^{Pro1E2}_{GGU}$ were assigned to AUU, CAU and ACU codons, respectively. It was confirmed that respective rP3 and rP4 expression was enhanced in the presence of 5 μM EF-P (FIG. 6B). On the other hand, no band was detected in the absence of EF-P. This means that markedly enhanced expression was observed in the rP3 and rP4 containing two kinds of two-consecutive D-amino acids (D-Ala$_2$-YY-D-Ala$_2$ (SEQ ID NO: 114) or D-Ala$_2$-YY-D-Cys$_2$ (SEQ ID NO: 115); Y=L-Tyr).

The rP5 peptide containing two kinds of two-consecutive D-amino acids (D-Ala$_2$-YY-D-Ser$_2$ (SEQ ID NO: 116)) expressed a detectable level of a rP5 peptide even in the absence of EF-P, but addition of EF-P enhanced the expression level by 13-fold (FIG. 6B and FIG. 7B).

The expression of rP6 and rP7 peptides alternately containing L- and D-amino acids was low but detectable in the presence of EF-P. On the other hand, the addition of EF-P enhanced the expression level by 3.3- and 3.0-fold, respectively (FIG. 6B and FIG. 7B).

MALDI-TOF mass spectrometric analysis showed that the peptides each had an expected molecular weight in the presence of EF-P (FIG. 6C).

The above-described results suggest that the combination of EF-P and D-aminoacyl-tRNA$^{Pro1E2}$ has a remarkable impact on the enhancement of the expression level of a peptide containing multiple kinds of D-amino acids.

Ribosomal Synthesis of Cyclic D-Peptide Stimulated by EF-P

As a result of demonstration of the expression of a macrocyclic D-peptide using a tRNA$^{GluE2}$ derivative by the FIT system, the expression level of the macrocyclic D-peptide was 4-fold lower than that of a macrocyclic L-peptide.

tRNA$^{Pro1E2}$ was therefore used, which enhanced the expression level of the macrocyclic D-peptide. More specifically, use of EF-P led to a success in enhancing the expression level of two model D-peptides of rP8 and rP9 peptides (FIG. 8).

The rP8 contains D-Cys-D-Ser-D-Ala-D-Ser-D-Cys (SEQ ID NO: 117).

MALDI-TOF mass spectrometric analysis of rP8 peptide expressed using tRNA$^{Pro1E2}$ as an elongator carrier with EF-P showed that the above D-amino acids were introduced correctly and two D-Cys residues formed a disulfide bond to give a macrocyclic structure (FIG. 9C).

Tricine-SDS-PAGE analysis of rP8 peptide showed that EF-P paired with D-aminoacyl-tRNA$^{Pro1E2}$ enhanced the expression level by about 8-fold compared with EF-P-inactive D-aminoacyl-tRNA$^{GlueE2}$ (FIG. 8B and FIG. 9A).

In a similar manner, rP9 peptide was designed as another model peptide containing a D-$^{ClAc}$Phe-D-Ser-D-Ser-D-Cys (SEQ ID NO: 118) continuous stretch. The N-terminal chloroacetyl group of D-$^{ClAc}$Phe reacted with the sulfhydryl group of D-Cys and formed a thioether macrocyclic structure (FIG. 8A). EF-P paired with D-aminoacyl-tRNA$^{Pro1E2}$ enhanced rP9 peptide expression by about 10-fold compared with tRNA$^{GluE2}$ (FIG. 8C), showing that a thioether macrocyclic D-peptide was produced efficiently (FIG. 9C).

Incorporation of Consecutive β-Amino Acids Enhanced by EF-P

Incorporation of D-amino acids was conducted as described below according to the above-described method.

Wild type (WT) tRNA$^{Pro1}_{CGG}$ or C13G mutant tRNA$^{Pro1}_{CGG}$ (FIG. 10a) was pre-charged with βhQ, βhM, and βhF (FIG. 10b) by the flexizyme technology and was used for the translation of a template mRNA of mR1 (FIG. 10c) in the FIT system containing 5 μM EF-protein to synthesize an rP1 peptide.

The Tyr-Lys-Lys-Tyr-Lys-Lys-Tys-Lys (SEQ ID NO: 119) sequence before the β-amino acid is a sequence introduced for the detection of the expressed peptide in tricine SDS-PAGE or MALDI-TOF mass spectrometric analysis.

The peptide was expressed in the presence of [$^{14}$C]Asp, subjected to 15% tricine SDS-PAGE, and quantified using autoradiography by the intensity of [$^{14}$C]Asp introduced into the flag-tag region at the C-terminal (FIG. 10d and FIG. 15a).

In the presence of cold Asp, expression of the same peptide was confirmed by MALDI-TOF mass spectrometric analysis even in the absence of EF-P (FIG. 15b). When the WT tRNA$^{Pro1}_{CGG}$ was used, the incorporation of 3-amino acids increased due to the presence of EF-P (FIG. 10d, 1.7-fold for βhQ, 4.6-fold for βhM, and 1.3-fold for βhF).

The above-described results clearly show that EF-P recognizes the D-arm structure of tRNA$^{Pro1}$. It promotes the incorporation of β-amino acids responding thereto.

Then, the optimized concentration of EF-P in the incorporation of βhQ and βhM into rP1 peptide was studied (Reference Literatures 1 and 2) and the EF-P concentration was preferably from about 5 to 10 μM in the incorporation of β-amino acids. A similar tendency was confirmed in the incorporation of D-alanine.

Based on the above-described results, it has been presumed that EF-P occupies the E site of ribosome and inhibits the translocation of deacyl tRNA from P site to E site.

Engineering of T-Stem Structure of tRNA$^{Pro1}$ for Enhancing EF-Tu Binding in Consecutive β-Alanine Incorporation tRNAs shown in FIG. 11a were charged with βhM by the flexizyme technology and whether or not further incorporation enhancement occurred was compared among the tRNAs charged with βhM.

In contrast with tRNA$^{AsnE2}$ based on Escherichia coli tRNA$^{Asn}$ and having a T-stem and a D-arm each of which was not optimized, tRNA$^{GluE2}$ derived from tRNA$^{Glu}$ having a T-stem optimized for EF-Tu binding, and tRNA$^{Pro1}$, βhM-tRNA$^{Pro1E2}$ showed a 7.3-fold incorporation enhancement effect in the presence of RF—P and showed almost a 2-fold incorporation enhancement effect over βhM-tRNA$^{Pro1}$ in the presence of EF-P (FIG. 11b).

Incorporation of 7 Consecutive β-Amino Acids

βhM was introduced into from 2 to 7 consecutive CGG codons of mR2 by using tRNA$^{GluE2}_{CGG}$ charged with βhM to synthesize rP2-βhM$_n$ peptides corresponding to mR2 (FIG. 12 and FIG. 16b).

Although the translation efficiency of rP2-βhM$_n$ peptides decreased with an increase in the number of consecutive βhMs, a full-length rP2 peptide containing 7-consecutive βhMs was detected in the presence of EF-P (FIG. 12b and FIG. 12c).

In addition, a marked incorporation enhancement effect by EF-P was confirmed in rP2-βhM$_2$ peptide and rP2-βhM$_3$ peptide (5.9-fold and 16.2-fold, respectively).

Similarly, tRNA$^{Pro1E2}_{GAU}$ and tRNA$^{Pro1E2}_{GUG}$ were pre-charged with βhM and βhF respectively and peptides of from rP3-3 to rP3-7 having each of them incorporated therein by AUU codon and CAU codon were synthesized (FIG. 13a).

Expression of the peptides of from rP3-3 to rP3-7 was confirmed in the presence of EF-P (FIG. 13b, FIG. 13c, and FIG. 16c).

In the peptides of from rP3-3 to rP3-5, a marked incorporation enhancement effect by EFP was confirmed (7.4-fold, 21.7-fold, and 30.3-fold, respectively). In addition, in the peptides of from rP3-6 to rP3-7, an expression enhancement effect by EF-P from N.D. to a detectable level was confirmed.

Incorporation of a Plurality of D-Amino Acids and β-Amino Acids

To show the versatility of the present method, eight kinds of peptides, that is, rP4 to rP11 having some of three kinds of β-amino acids and four kinds of D-amino acids incorporated at various positions thereof were synthesized (FIG. 14a and FIG. 14b).

The peptides of from rP4 to rP5 showed an incorporation enhancement effect by EF-P (1.9-fold and 1.6-fold, respectively in FIG. 14c and FIG. 16d). The peptides of from rP6 to rP7, which had two sets of consecutive β-amino acids incorporated therein, showed an incorporation enhancement effect by EF-P (12.3-fold and 19.3-fold, respectively in FIG. 14c and FIG. 16d). The peptides of from rP8 to rP9, which had a combination of β-amino acids and D-amino acids incorporated therein, showed an incorporation enhancement effect by EP to elevate an expression level to a detectable one (9.2-fold for rP8 peptide and 0.04 µM for rP8 peptide in FIG. 14c and FIG. 16d).

Macrocyclic peptides formed by a thioether bond (from rP10 peptide to rP11 peptide) having consecutive β-amino acids incorporated therein were synthesized (FIG. 14a). An initiator codon was assigned to D-$^{ClAc}$Phe and the chloroacetyl group of the D-$^{ClAc}$Phe reacted with a side-chain thiol group of D-cysteine downstream thereof to form a thioether bond. rP10 peptide and rP11 peptide also showed an incorporation enhancement effect by EF-P (3.2-fold and 2.3-fold, respectively, in FIG. 14d and FIG. 16d).

A by-product was produced due to an incorporation mistake and synthesis of the peptides was confirmed by MALDI-TOF mass spectrometric analysis (FIG. 16e).

REFERENCE LITERATURES

1. Ude, S. et al. Translation elongation factor EF-P alleviates ribosome stalling at polyproline stretches. Science 339, 82-5 (2013).
2. Doerfel, L. K. et al. EF-P is essential for rapid synthesis of proteins containing consecutive proline residues. Science 339, 85-8 (2013).
3. Katoh, T., Wohlgemuth, I., Nagano, M., Rodnina, M. V. & Suga, H. Essential structural elements in tRNA(Pro) for EF-P-mediated alleviation of translation stalling. Nat Commun 7, 11657 (2016).
4. LaRiviere, F. J., Wolfson, A. D. & Uhlenbeck, O. C. Uniform binding of aminoacyl-tRNAs to elongation factor Tu by thermodynamic compensation. Science 294, 165-8 (2001).
5. Dale, T., Sanderson, L. E. & Uhlenbeck, O. C. The affinity of elongation factor Tu for an aminoacyl-tRNA is modulated by the esterified amino acid. Biochemistry 43, 6159-66 (2004).
6. Becker, H. D. & Kern, D. *Thermus thermophilus*: a link in evolution of the tRNA-dependent amino acid amidation pathways. Proc Natl Acad Sci USA 95, 12832-7 (1998).
7. Stanzel, M., Schon, A. & Sprinzl, M. Discrimination against misacylated tRNA by chloroplast elongation factor Tu. Eur J Biochem 219, 435-9 (1994).
8. Schrader, J. M., Chapman, S. J. & Uhlenbeck, O. C. Tuning the affinity of aminoacyl-tRNA to elongation factor Tu for optimal decoding. Proc Natl Acad Sci USA 108, 5215-20 (2011).
9. Hasegawa, T. & Yokogawa, T. *Escherichia coli* proline tRNA: structure and recognition sites for prolyl-tRNA synthetase. Nucleic Acids Symp. Ser. 44, 7-8 (2000).
10. Pavlov, M. Y. et al. Slow peptide bond formation by proline and other N-alkylamino acids in translation. Proc Natl Acad Sci USA 106, 50-4 (2009).
11. Doerfel, L. K. et al. Entropic Contribution of Elongation Factor P to Proline Positioning at the Catalytic Center of the Ribosome. J Am Chem Soc 137, 12997-3006 (2015).
12. Wohlgemuth, I., Brenner, S., Beringer, M. & Rodnina, M. V. Modulation of the rate of peptidyl transfer on the ribosome by the nature of substrates. J Biol Chem 283, 32229-35 (2008).
13. Johansson, M. et al. pH-sensitivity of the ribosomal peptidyl transfer reaction dependent on the identity of the A-site aminoacyl-tRNA. Proc Natl Acad Sci USA 108, 79-84 (2011).
14. Melnikov, S. et al. Molecular insights into protein synthesis with proline residues. EMBO Rep 17, 1776-1784 (2016).
15. Driggers, E. M., Hale, S. P., Lee, J. & Terrett, N. K. The exploration of macrocycles for drug discovery—an underexploited structural class. Nat Rev Drug Discov 7, 608-24 (2008).
16. Hipolito, C. J. & Suga, H. Ribosomal production and in vitro selection of natural product-like peptidomimetics: the FIT and RaPID systems. Curr Opin Chem Biol 16, 196-203 (2012).
17. Passioura, T., Katoh, T., Goto, Y. & Suga, H. Selection-based discovery of druglike macrocyclic peptides. Annu Rev Biochem 83, 727-52 (2014).
18. Saito, H., Kourouklis, D. & Suga, H. An in vitro evolved precursor tRNA with aminoacylation activity. EMBO J 20, 1797-806 (2001).

What is claimed is:

1. A tRNA comprising the base sequence of SEQ ID NO: 1 and encoding a non-proteinogenic amino acid $$N_1N_2GCN_3N_4N_5N_6N_7N_8N_9N_{10}N_{11}GCN_{12}N_{13} \quad \text{(SEQ ID NO: 1)}$$

wherein $N_1$ to $N_{13}$ each represents an arbitrary base, $N_3$ to $N_{11}$ form a D-loop, and $N_1N_2GC$ forms a base pair with $N_{13}N_{12}CG$, and said tRNA is an elongator tRNA whereby the base at its 5' end forms a base pair with corresponding base on the 3' side of its acceptor stem.

2. The tRNA according to claim 1, further comprising the base sequence of SEQ ID NO: 2

$$AGGGG(N_{14})_mCCCCU \quad \text{(SEQ ID NO: 2)}$$

wherein $N_{14}$ represents an arbitrary base, m stands for an integer of 1 or more, $(N_{14})_m$ form a T-loop, and AGGGG forms a base pair with UCCCC.

3. The tRNA according to claim 2, wherein the non-proteinogenic amino acid is a D-amino acid, a β-amino acid, or an α,α-disubstituted amino acid.

4. A translation system for the synthesis of a peptide having two or more consecutive non-proteinogenic amino acids, comprising the tRNA of claim 2.

5. A method of constructing a peptide library, comprising a step of translating in a cell-free translation system by using the tRNA of claim 2.

6. A method of constructing a library of a complex between a peptide and an mRNA encoding the peptide, comprising a step of translating in a cell-free translation system by using the tRNA of claim 2.

7. The tRNA according to claim 1, wherein the non-proteinogenic amino acid is a D-amino acid, a β-amino acid, or an α,α-disubstituted amino acid.

8. A translation system for the synthesis of a peptide having two or more consecutive non-proteinogenic amino acids, comprising the tRNA of claim 7.

9. A method of constructing a peptide library, comprising a step of translating in a cell-free translation system by using the tRNA of claim 7.

10. A method of constructing a library of a complex between a peptide and an mRNA encoding the peptide, comprising a step of translating in a cell-free translation system by using the tRNA of claim 7.

11. A translation system for the synthesis of a peptide having two or more consecutive non-proteinogenic amino acids, comprising the tRNA of claim 1.

12. A method of constructing a peptide library, comprising a step of translating in a cell-free translation system by using the tRNA of claim 1.

13. A method of constructing a library of a complex between a peptide and an mRNA encoding the peptide, comprising a step of translating in a cell-free translation system by using the tRNA of claim 1.

14. A tRNA comprising the base sequence of SEQ ID NO: 1 and encoding a non-proteinogenic amino acid $$N_1N_2GCN_3N_4N_5N_6N_7N_8N_9N_{10}N_{11}GCN_{12}N_{13} \quad \text{(SEQ ID NO: 1)}$$

wherein $N_1$ to $N_{13}$ each represents an arbitrary base, $N_3$ to $N_{11}$ form a D-loop, and $N_1N_2GC$ forms a base pair with $N_{13}N_{12}CG$, and further comprising the base sequence of SEQ ID NO: 2

$$AGGGG(N_{14})_mCCCCU \quad \text{(SEQ ID NO: 2)}$$

wherein $N_{14}$ represents an arbitrary base, m stands for an integer of 1 or more, $(N_{14})_m$ form a T-loop, and AGGGG forms a base pair with UCCCC, and said tRNA is an elongator tRNA whereby the base at its 5' end forms a base pair with corresponding base on the 3' side of its acceptor stem.

15. The tRNA according to claim 14, wherein the integer is 2 or more.

* * * * *

SEQUENCE LISTING

```
<160> NUMBER OF SEQ ID NOS: 132

<210> SEQ ID NO 1
<211> LENGTH: 17
<212> TYPE: RNA
<213> ORGANISM: Artificial Sequence
<220> FEATURE:
```

-continued

```
<223> OTHER INFORMATION: D-arm of tRNA
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (5)..(13)
<223> OTHER INFORMATION: n is a, c, g, or u
<220> FEATURE:
<221> NAME/KEY: misc_feature
<222> LOCATION: (16)..(17)
<223> OTHER INFORMATION: n is a, c, g, or u

<400> SEQUENCE: 1
nngcnnnnnn nnngcnn                                                    17

<210> SEQ ID NO 2
<211> LENGTH: 11
<212> TYPE: RNA
<213> ORGANISM: Artificial Sequence
<220> FEATURE:
<223> OTHER INFORMATION: T-arm of tRNA
<220> FEATURE:
<221> NAME/KEY: misc_feature
<222> LOCATION: (6)..(6)
<223> OTHER INFORMATION: n is a, c, g, or u

<400> SEQUENCE: 2
aggggncccc u                                                          11

<210> SEQ ID NO 3
<211> LENGTH: 17
<212> TYPE: RNA
<213> ORGANISM: Artificial Sequence
<220> FEATURE:
<223> OTHER INFORMATION: D-arm of tRNA
<220> FEATURE:
<221> NAME/KEY: misc_feature
<222> LOCATION: (5)..(13)
<223> OTHER INFORMATION: n is a, c, g, or u

<400> SEQUENCE: 3
gcgcnnnnnn nnngcgc                                                    17

<210> SEQ ID NO 4
<211> LENGTH: 9
<212> TYPE: RNA
<213> ORGANISM: Artificial Sequence
<220> FEATURE:
<223> OTHER INFORMATION: D-loop of tRNA

<400> SEQUENCE: 4 agccuggua                                                              9

<210> SEQ ID NO 5
<211> LENGTH: 21
<212> TYPE: RNA
<213> ORGANISM: Artificial Sequence
<220> FEATURE:
<223> OTHER INFORMATION: D-arm of tRNA
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 5
```
nngcgcagcc ugguagcgcn n                                              21

<210> SEQ ID NO 6
<211> LENGTH: 21
<212> TYPE: RNA
<213> ORGANISM: Artificial Sequence
<220> FEATURE:
<223> OTHER INFORMATION: D-arm of tRNA

<400> SEQUENCE: 6
gcgcgcagcc ugguagcgcg c                                              21

<210> SEQ ID NO 7
<211> LENGTH: 7
<212> TYPE: RNA
<213> ORGANISM: Artificial Sequence
<220> FEATURE:
<223> OTHER INFORMATION: T-loop of tRNA

<400> SEQUENCE: 7 uucgaau                                                              7

<210> SEQ ID NO 8
<211> LENGTH: 46
<212> TYPE: RNA
<213> ORGANISM: Artificial Sequence
<220> FEATURE:
<223> OTHER INFORMATION: dFx

<400> SEQUENCE: 8
ggaucgaaag auuuccgcau ccccgaaagg guacauggcg uuaggu                    46

<210> SEQ ID NO 9
<211> LENGTH: 45
<212> TYPE: RNA
<213> ORGANISM: Artificial Sequence
<220> FEATURE:
<223> OTHER INFORMATION: eFx

<400> SEQUENCE: 9
ggaucgaaag auuuccgcgg ccccgaaagg ggauuagcgu uaggu                     45

<210> SEQ ID NO 10
<211> LENGTH: 77
<212> TYPE: RNA
<213> ORGANISM: Artificial Sequence
<220> FEATURE:
<223> OTHER INFORMATION: tRNA, Pro1(CGG)

<400> SEQUENCE: 10
cggugauugg cgcagccugg uagcgcacuu cguucgggac gaaggggucg gagguucgaa     60
uccucuauca ccgacca                                                   77

<210> SEQ ID NO 11
<211> LENGTH: 77
<212> TYPE: RNA
<213> ORGANISM: Artificial Sequence
<220> FEATURE:
<223> OTHER INFORMATION: tRNA, Pro1(GGU)

<400> SEQUENCE: 11
cggugauugg cgcagccugg uagcgcacuu cguugguaac gaaggggucg gagguucgaa     60
uccucuauca ccgacca                                                   77

<210> SEQ ID NO 12
<211> LENGTH: 77
<212> TYPE: RNA
<213> ORGANISM: Artificial Sequence
<220> FEATURE:
<223> OTHER INFORMATION: tRNA, Pro1(GUG)

<400> SEQUENCE: 12
cggugauugg cgcagccugg uagcgcacuu cguugugaac gaaggggucg gagguucgaa    60
uccucuauca ccgacca                                                  77

<210> SEQ ID NO 13
<211> LENGTH: 77
<212> TYPE: RNA
<213> ORGANISM: Artificial Sequence
<220> FEATURE:
<223> OTHER INFORMATION: tRNA, Pro1C13G(CGG)

<400> SEQUENCE: 13
cggugauugg cggagccugg uagcgcacuu cguucgggac gaaggggucg gagguucgaa    60
uccucuauca ccgacca                                                  77

<210> SEQ ID NO 14
<211> LENGTH: 77
<212> TYPE: RNA
<213> ORGANISM: Artificial Sequence
<220> FEATURE:
<223> OTHER INFORMATION: tRNA, Pro1E1(CGG)

<400> SEQUENCE: 14
cggugauugg cgcagccugg uagcgcacuu cguucgggac gaagggguca gggguucgaa    60
uccccuauca ccgacca                                                  77

<210> SEQ ID NO 15
<211> LENGTH: 77
<212> TYPE: RNA
<213> ORGANISM: Artificial Sequence
<220> FEATURE:
<223> OTHER INFORMATION: tRNA, Pro1E2(CGG)

<400> SEQUENCE: 15
gggugauugg cgcagccugg uagcgcacuu cguucgggac gaagggguca ggggu ucgaa    60 uccccuauca cccgcca                                                  77

<210> SEQ ID NO 16
<211> LENGTH: 77
<212> TYPE: RNA
<213> ORGANISM: Artificial Sequence
<220> FEATURE:
<223> OTHER INFORMATION: tRNA, Pro1E2(GAU)

<400> SEQUENCE: 16
gggugauugg cgcagccugg uagcgcacuu cgcugauaac gaagggguca ggggu ucgaa    60 uccccuauca cccgcca                                                  77

<210> SEQ ID NO 17
<211> LENGTH: 77
<212> TYPE: RNA
<213> ORGANISM: Artificial Sequence
<220> FEATURE:
<223> OTHER INFORMATION: tRNA, Pro1E2(GGU)

<400> SEQUENCE: 17

-continued gggugauugg cgcagccugg uagcgcacuu cguugguaac gaaggggauca gggguucgaa    60 uccccuauca cccgcca    77

<210> SEQ ID NO 18
<211> LENGTH: 77
<212> TYPE: RNA
<213> ORGANISM: Artificial Sequence
<220> FEATURE:
<223> OTHER INFORMATION: tRNA, ProlE2(GUG)

<400> SEQUENCE: 18
gggugauugg cgcagccugg uagcgcacuu cguugugaac gaaggggauca gggguucgaa    60 uccccuauca cccgcca    77

<210> SEQ ID NO 19
<211> LENGTH: 76
<212> TYPE: RNA
<213> ORGANISM: Artificial Sequence
<220> FEATURE:
<223> OTHER INFORMATION: tRNA, GluE2(CGG)

<400> SEQUENCE: 19
guccccuucg ucuagaggcc caggacaccg ccuucgggag gcgguaacag ggguucgaau    60
ccccuagggg acgcca    76

<210> SEQ ID NO 20
<211> LENGTH: 76
<212> TYPE: RNA
<213> ORGANISM: Artificial Sequence
<220> FEATURE:
<223> OTHER INFORMATION: tRNA, AsnE2(CGG)

<400> SEQUENCE: 20
ggcucuguag uucagucggu agaacggcgg auucgggauc cguaugucac ugguucgagu    60
ccagucagag ccgcca    76

<210> SEQ ID NO 21
<211> LENGTH: 77
<212> TYPE: RNA
<213> ORGANISM: Artificial Sequence
<220> FEATURE:
<223> OTHER INFORMATION: tRNA, fMet(CAU)

<400> SEQUENCE: 21
cgcgggguga agcagccugg uagcucgucg ggcucauaac ccgaagaucg ucgguucaaa    60
uccggccccc gcaacca    77

<210> SEQ ID NO 22
<211> LENGTH: 36
<212> TYPE: DNA
<213> ORGANISM: Artificial Sequence
<220> FEATURE:
<223> OTHER INFORMATION: Extension primer (forward) for dFx

<400> SEQUENCE: 22
gtaatacgac tcactatagg atcgaaagat ttccgc    36

<210> SEQ ID NO 23
<211> LENGTH: 36
<212> TYPE: DNA
<213> ORGANISM: Artificial Sequence
<220> FEATURE:

<223> OTHER INFORMATION: Extension primer (forward) for eFx

<400> SEQUENCE: 23
gtaatacgac tcactatagg atcgaaagat ttccgc                              36

<210> SEQ ID NO 24
<211> LENGTH: 59
<212> TYPE: DNA
<213> ORGANISM: Artificial Sequence
<220> FEATURE:
<223> OTHER INFORMATION: Extension primer (forward) for tRNA, Pro1(CGG)

<400> SEQUENCE: 24
gtaatacgac tcactatacg gtgattggcg cagcctggta gcgcacttcg ttcgggacg     59

<210> SEQ ID NO 25
<211> LENGTH: 50
<212> TYPE: DNA
<213> ORGANISM: Artificial Sequence
<220> FEATURE:
<223> OTHER INFORMATION: Extension primer (forward) for tRNA, Pro1(GGU)

<400> SEQUENCE: 25
gtaatacgac tcactatagg gtgattggcg cagcctggta gcgcacttcg               50

<210> SEQ ID NO 26
<211> LENGTH: 50
<212> TYPE: DNA
<213> ORGANISM: Artificial Sequence
<220> FEATURE:
<223> OTHER INFORMATION: Extension primer (forward) for tRNA, Pro1(GUG)

<400> SEQUENCE: 26
gtaatacgac tcactatagg gtgattggcg cagcctggta gcgcacttcg               50

<210> SEQ ID NO 27
<211> LENGTH: 59
<212> TYPE: DNA
<213> ORGANISM: Artificial Sequence
<220> FEATURE:
<223> OTHER INFORMATION: Extension primer (forward) for tRNA,
      Pro1C13G(CGG)

<400> SEQUENCE: 27
gtaatacgac tcactatacg gtgattggcg gagcctggta gcgcacttcg ttcgggacg     59

<210> SEQ ID NO 28
<211> LENGTH: 50
<212> TYPE: DNA
<213> ORGANISM: Artificial Sequence
<220> FEATURE:
<223> OTHER INFORMATION: Extension primer (forward) for tRNA,
      Pro1E1(CGG)

<400> SEQUENCE: 28
gtaatacgac tcactatacg gtgattggcg cagcctggta gcgcacttcg               50

<210> SEQ ID NO 29
<211> LENGTH: 50
<212> TYPE: DNA
<213> ORGANISM: Artificial Sequence
<220> FEATURE:
<223> OTHER INFORMATION: Extension primer (forward) for tRNA,
      Pro1E2(CGG)

<400> SEQUENCE: 29

```
gtaatacgac tcactatagg gtgattggcg cagcctggta gcgcacttcg          50
```

<210> SEQ ID NO 30
<211> LENGTH: 50
<212> TYPE: DNA
<213> ORGANISM: Artificial Sequence
<220> FEATURE:
<223> OTHER INFORMATION: Extension primer (forward) for tRNA,
      Pro1E2(GAU)

<400> SEQUENCE: 30

```
gtaatacgac tcactatagg gtgattggcg cagcctggta gcgcacttcg          50
```

<210> SEQ ID NO 31
<211> LENGTH: 50
<212> TYPE: DNA
<213> ORGANISM: Artificial Sequence
<220> FEATURE:
<223> OTHER INFORMATION: Extension primer (forward) for tRNA,
      Pro1E2(GGU)

<400> SEQUENCE: 31

```
gtaatacgac tcactatagg gtgattggcg cagcctggta gcgcacttcg          50
```

<210> SEQ ID NO 32
<211> LENGTH: 50
<212> TYPE: DNA
<213> ORGANISM: Artificial Sequence
<220> FEATURE:
<223> OTHER INFORMATION: Extension primer (forward) for tRNA,
      Pro1E2(GUG)

<400> SEQUENCE: 32

```
gtaatacgac tcactatagg gtgattggcg cagcctggta gcgcacttcg          50
```

<210> SEQ ID NO 33
<211> LENGTH: 64
<212> TYPE: DNA
<213> ORGANISM: Artificial Sequence
<220> FEATURE:
<223> OTHER INFORMATION: Extension primer (forward) for tRNA, GluE2(CGG)

<400> SEQUENCE: 33

```
cactatagtc cccttcgtct agaggcccag gacaccgccu ucgggaggcg gtaacagggg   60
ttcg                                                              64
```

<210> SEQ ID NO 34
<211> LENGTH: 49
<212> TYPE: DNA
<213> ORGANISM: Artificial Sequence
<220> FEATURE:
<223> OTHER INFORMATION: Extension primer (forward) for tRNA, AsnE2(CGG)

<400> SEQUENCE: 34

```
gtaatacgac tcactatagg ctctgtagtt cagtcggtag aacggcgga            49
```

<210> SEQ ID NO 35
<211> LENGTH: 68
<212> TYPE: DNA
<213> ORGANISM: Artificial Sequence
<220> FEATURE:
<223> OTHER INFORMATION: Extension primer (forward) for tRNA, fMet(CAU)

<400> SEQUENCE: 35

```
gtaatacgac tcactatacg cggggtggag cagcctggta gctcgtcggg ctcataaccc   60
``` gaagatcg                                                                68

<210> SEQ ID NO 36
<211> LENGTH: 46
<212> TYPE: DNA
<213> ORGANISM: Artificial Sequence
<220> FEATURE:
<223> OTHER INFORMATION: Extension primer (reverse) for dFx

<400> SEQUENCE: 36
acctaacgcc atgtaccctt tcggggatgc ggaaatcttt cgatcc               46

<210> SEQ ID NO 37
<211> LENGTH: 45
<212> TYPE: DNA
<213> ORGANISM: Artificial Sequence
<220> FEATURE:
<223> OTHER INFORMATION: Extension primer (reverse) for eFx

<400> SEQUENCE: 37
acctaacgct aatccccttt cggggccgcg gaaatcttc gatcc                 45

<210> SEQ ID NO 38
<211> LENGTH: 53
<212> TYPE: DNA
<213> ORGANISM: Artificial Sequence
<220> FEATURE:
<223> OTHER INFORMATION: Extension primer (reverse) for tRNA, Pro1(CGG)

<400> SEQUENCE: 38
tggtcggtga tagaggattc gaacctccga ccccttcgtc ccgaacgaag tgc       53

<210> SEQ ID NO 39
<211> LENGTH: 62
<212> TYPE: DNA
<213> ORGANISM: Artificial Sequence
<220> FEATURE:
<223> OTHER INFORMATION: Extension primer (reverse) for tRNA, Pro1(GGU)

<400> SEQUENCE: 39
tggtcggtga tagaggattc gaacctccga ccccttcgtt accaacgaag tgcgctacca  60
gg                                                                62

<210> SEQ ID NO 40
<211> LENGTH: 62
<212> TYPE: DNA
<213> ORGANISM: Artificial Sequence
<220> FEATURE:
<223> OTHER INFORMATION: Extension primer (reverse) for tRNA, Pro1(GUG)

<400> SEQUENCE: 40
tggtcggtga tagaggattc gaacctccga ccccttcgtt cacaacgaag tgcgctacca  60
gg                                                                62

<210> SEQ ID NO 41
<211> LENGTH: 53
<212> TYPE: DNA
<213> ORGANISM: Artificial Sequence
<220> FEATURE:
<223> OTHER INFORMATION: Extension primer (reverse) for tRNA,
      Pro1C13G(CGG)

<400> SEQUENCE: 41
tggtcggtga tagaggattc gaacctccga ccccttcgtc ccgaacgaag tgc       53

<210> SEQ ID NO 42
<211> LENGTH: 62
<212> TYPE: DNA
<213> ORGANISM: Artificial Sequence
<220> FEATURE:
<223> OTHER INFORMATION: Extension primer (reverse) for tRNA,
      Pro1E1(CGG)

<400> SEQUENCE: 42
tggtcggtga tagggattc gaaccccctga ccccttcgtc ccgaacgaag tgcgctacca    60
gg                                                                  62

<210> SEQ ID NO 43
<211> LENGTH: 62
<212> TYPE: DNA
<213> ORGANISM: Artificial Sequence
<220> FEATURE:
<223> OTHER INFORMATION: Extension primer (reverse) for tRNA,
      Pro1E2(CGG)

<400> SEQUENCE: 43
tggcgggtga tagggattc gaaccccctga ccccttcgtc ccgaacgaag tgcgctacca    60
gg                                                                  62

<210> SEQ ID NO 44
<211> LENGTH: 62
<212> TYPE: DNA
<213> ORGANISM: Artificial Sequence
<220> FEATURE:
<223> OTHER INFORMATION: Extension primer (reverse) for tRNA,
      Pro1E2(GAU)

<400> SEQUENCE: 44
tggcgggtga tagaggattc gaacctccga ccccttcgtt atcagcgaag tgcgctacca    60
gg                                                                  62

<210> SEQ ID NO 45
<211> LENGTH: 62
<212> TYPE: DNA
<213> ORGANISM: Artificial Sequence
<220> FEATURE:
<223> OTHER INFORMATION: Extension primer (reverse) for tRNA,
      Pro1E2(GGU)

<400> SEQUENCE: 45
tggcgggtga tagaggattc gaacctccga ccccttcgtt accaacgaag tgcgctacca    60
gg                                                                  62

<210> SEQ ID NO 46
<211> LENGTH: 62
<212> TYPE: DNA
<213> ORGANISM: Artificial Sequence
<220> FEATURE:
<223> OTHER INFORMATION: Extension primer (reverse) for tRNA,
      Pro1E2(GUG)

<400> SEQUENCE: 46
tggcgggtga tagaggattc gaacctccga ccccttcgtt cacaacgaag tgcgctacca    60
gg                                                                  62

<210> SEQ ID NO 47
<211> LENGTH: 41
<212> TYPE: DNA

```
<213> ORGANISM: Artificial Sequence
<220> FEATURE:
<223> OTHER INFORMATION: Extension primer (reverse) for tRNA, GluE2(CGG)

<400> SEQUENCE: 47
tggcgtcccc tagggattc gaacccctgt taccgccttc g                          41

<210> SEQ ID NO 48
<211> LENGTH: 64
<212> TYPE: DNA
<213> ORGANISM: Artificial Sequence
<220> FEATURE:
<223> OTHER INFORMATION: Extension primer (reverse) for tRNA, AsnE2(CGG)

<400> SEQUENCE: 48
tggcggctct gactggactc gaaccagtga catacggatc ccgaatccgc cgttctaccg    60
actg                                                                  64

<210> SEQ ID NO 49
<211> LENGTH: 46
<212> TYPE: DNA
<213> ORGANISM: Artificial Sequence
<220> FEATURE:
<223> OTHER INFORMATION: Extension primer (reverse) for tRNA, fMet(CAU)

<400> SEQUENCE: 49
tggttgcggg ggccggattt gaaccgacga tcttcgggtt atgagc                    46

<210> SEQ ID NO 50
<211> LENGTH: 22
<212> TYPE: DNA
<213> ORGANISM: Artificial Sequence
<220> FEATURE:
<223> OTHER INFORMATION: PCR primer (foward) for dFx

<400> SEQUENCE: 50
ggcgtaatac gactcactat ag                                              22

<210> SEQ ID NO 51
<211> LENGTH: 22
<212> TYPE: DNA
<213> ORGANISM: Artificial Sequence
<220> FEATURE:
<223> OTHER INFORMATION: PCR primer (foward) for eFx

<400> SEQUENCE: 51
ggcgtaatac gactcactat ag                                              22

<210> SEQ ID NO 52
<211> LENGTH: 22
<212> TYPE: DNA
<213> ORGANISM: Artificial Sequence
<220> FEATURE:
<223> OTHER INFORMATION: PCR primer (foward) for tRNA, Pro1(CGG)

<400> SEQUENCE: 52
ggcgtaatac gactcactat ac                                              22

<210> SEQ ID NO 53
<211> LENGTH: 22
<212> TYPE: DNA
<213> ORGANISM: Artificial Sequence
<220> FEATURE:
<223> OTHER INFORMATION: PCR primer (foward) for tRNA, Pro1(GGU)

<400> SEQUENCE: 53
```
ggcgtaatac gactcactat ac                                              22

<210> SEQ ID NO 54
<211> LENGTH: 22
<212> TYPE: DNA
<213> ORGANISM: Artificial Sequence
<220> FEATURE:
<223> OTHER INFORMATION: PCR primer (foward) for tRNA, Pro1(GUG)

<400> SEQUENCE: 54
ggcgtaatac gactcactat ac                                              22

<210> SEQ ID NO 55
<211> LENGTH: 22
<212> TYPE: DNA
<213> ORGANISM: Artificial Sequence
<220> FEATURE:
<223> OTHER INFORMATION: PCR primer (foward) for tRNA, Pro1C13G(CGG)

<400> SEQUENCE: 55
ggcgtaatac gactcactat ac                                              22

<210> SEQ ID NO 56
<211> LENGTH: 22
<212> TYPE: DNA
<213> ORGANISM: Artificial Sequence
<220> FEATURE:
<223> OTHER INFORMATION: PCR primer (foward) for tRNA, Pro1E1(CGG)

<400> SEQUENCE: 56
ggcgtaatac gactcactat ac                                              22

<210> SEQ ID NO 57
<211> LENGTH: 22
<212> TYPE: DNA
<213> ORGANISM: Artificial Sequence
<220> FEATURE:
<223> OTHER INFORMATION: PCR primer (foward) for tRNA, Pro1E2(CGG)

<400> SEQUENCE: 57
ggcgtaatac gactcactat ag                                              22

<210> SEQ ID NO 58
<211> LENGTH: 22
<212> TYPE: DNA
<213> ORGANISM: Artificial Sequence
<220> FEATURE:
<223> OTHER INFORMATION: PCR primer (foward) for tRNA, Pro1E2(GAU)

<400> SEQUENCE: 58
ggcgtaatac gactcactat ag                                              22

<210> SEQ ID NO 59
<211> LENGTH: 22
<212> TYPE: DNA
<213> ORGANISM: Artificial Sequence
<220> FEATURE:
<223> OTHER INFORMATION: PCR primer (foward) for tRNA, Pro1E2(GGU)

<400> SEQUENCE: 59
ggcgtaatac gactcactat ag                                              22

<210> SEQ ID NO 60
<211> LENGTH: 22
<212> TYPE: DNA

```
<213> ORGANISM: Artificial Sequence
<220> FEATURE:
<223> OTHER INFORMATION: PCR primer (foward) for tRNA, Pro1E2(GUG)

<400> SEQUENCE: 60
ggcgtaatac gactcactat ag                                              22

<210> SEQ ID NO 61
<211> LENGTH: 37
<212> TYPE: DNA
<213> ORGANISM: Artificial Sequence
<220> FEATURE:
<223> OTHER INFORMATION: PCR primer (foward) for tRNA, GluE2(CGG)

<400> SEQUENCE: 61
gtaatacgac tcactatagt ccccttcgtc tagttcg                              37

<210> SEQ ID NO 62
<211> LENGTH: 19
<212> TYPE: DNA
<213> ORGANISM: Artificial Sequence
<220> FEATURE:
<223> OTHER INFORMATION: PCR primer (foward) for tRNA, AsnE2(CGG)

<400> SEQUENCE: 62
gtaatacgac tcactatag                                                  19

<210> SEQ ID NO 63
<211> LENGTH: 22
<212> TYPE: DNA
<213> ORGANISM: Artificial Sequence
<220> FEATURE:
<223> OTHER INFORMATION: PCR primer (foward) for tRNA, fMet(CAU)

<400> SEQUENCE: 63
ggcgtaatac gactcactat ac                                              22

<210> SEQ ID NO 64
<211> LENGTH: 19
<212> TYPE: DNA
<213> ORGANISM: Artificial Sequence
<220> FEATURE:
<223> OTHER INFORMATION: PCR primer (reverse) for dFx

<400> SEQUENCE: 64
acctaacgcc atgtaccct                                                  19

<210> SEQ ID NO 65
<211> LENGTH: 18
<212> TYPE: DNA
<213> ORGANISM: Artificial Sequence
<220> FEATURE:
<223> OTHER INFORMATION: PCR primer (reverse) for eFx

<400> SEQUENCE: 65
acctaacgct aatcccct                                                   18

<210> SEQ ID NO 66
<211> LENGTH: 20
<212> TYPE: DNA
<213> ORGANISM: Artificial Sequence
<220> FEATURE:
<223> OTHER INFORMATION: PCR primer (reverse) for tRNA, Pro1(CGG)
<220> FEATURE:
<221> NAME/KEY: misc_feature
<222> LOCATION: (2)..(2)
<223> OTHER INFORMATION: gm
```

<400> SEQUENCE: 66
tngtcggtga tagaggattc                                               20

<210> SEQ ID NO 67
<211> LENGTH: 20
<212> TYPE: DNA
<213> ORGANISM: Artificial Sequence
<220> FEATURE:
<223> OTHER INFORMATION: PCR primer (reverse) for tRNA, Pro1(GGU)
<220> FEATURE:
<221> NAME/KEY: misc_feature
<222> LOCATION: (2)..(2)
<223> OTHER INFORMATION: gm

<400> SEQUENCE: 67
tngtcggtga tagaggattc                                               20

<210> SEQ ID NO 68
<211> LENGTH: 20
<212> TYPE: DNA
<213> ORGANISM: Artificial Sequence
<220> FEATURE:
<223> OTHER INFORMATION: PCR primer (reverse) for tRNA, Pro1(GUG)
<220> FEATURE:
<221> NAME/KEY: misc_feature
<222> LOCATION: (2)..(2)
<223> OTHER INFORMATION: gm

<400> SEQUENCE: 68
tngtcggtga tagaggattc                                               20

<210> SEQ ID NO 69
<211> LENGTH: 20
<212> TYPE: DNA
<213> ORGANISM: Artificial Sequence
<220> FEATURE:
<223> OTHER INFORMATION: PCR primer (reverse) for tRNA, Pro1C13G(CGG)
<220> FEATURE:
<221> NAME/KEY: misc_feature
<222> LOCATION: (2)..(2)
<223> OTHER INFORMATION: gm

<400> SEQUENCE: 69
tngtcggtga tagaggattc                                               20

<210> SEQ ID NO 70
<211> LENGTH: 20
<212> TYPE: DNA
<213> ORGANISM: Artificial Sequence
<220> FEATURE:
<223> OTHER INFORMATION: PCR primer (reverse) for tRNA, Pro1E1(CGG)
<220> FEATURE:
<221> NAME/KEY: misc_feature
<222> LOCATION: (2)..(2)
<223> OTHER INFORMATION: gm

<400> SEQUENCE: 70
tngtcggtga tagggattc                                                20

<210> SEQ ID NO 71
<211> LENGTH: 20
<212> TYPE: DNA
<213> ORGANISM: Artificial Sequence
<220> FEATURE:
<223> OTHER INFORMATION: PCR primer (reverse) for tRNA, Pro1E2(CGG)
<220> FEATURE:
<221> NAME/KEY: misc_feature
<222> LOCATION: (2)..(2)

<223> OTHER INFORMATION: gm

<400> SEQUENCE: 71
tngcgggtga tagggattc                                            20

<210> SEQ ID NO 72
<211> LENGTH: 20
<212> TYPE: DNA
<213> ORGANISM: Artificial Sequence
<220> FEATURE:
<223> OTHER INFORMATION: PCR primer (reverse) for tRNA, Pro1E2(GAU)
<220> FEATURE:
<221> NAME/KEY: misc_feature
<222> LOCATION: (2)..(2)
<223> OTHER INFORMATION: gm

<400> SEQUENCE: 72
tngcgggtga tagggattc                                            20

<210> SEQ ID NO 73
<211> LENGTH: 20
<212> TYPE: DNA
<213> ORGANISM: Artificial Sequence
<220> FEATURE:
<223> OTHER INFORMATION: PCR primer (reverse) for tRNA, Pro1E2(GGU)
<220> FEATURE:
<221> NAME/KEY: misc_feature
<222> LOCATION: (2)..(2)
<223> OTHER INFORMATION: gm

<400> SEQUENCE: 73
tngcgggtga tagggattc                                            20

<210> SEQ ID NO 74
<211> LENGTH: 20
<212> TYPE: DNA
<213> ORGANISM: Artificial Sequence
<220> FEATURE:
<223> OTHER INFORMATION: PCR primer (reverse) for tRNA, Pro1E2(GUG)
<220> FEATURE:
<221> NAME/KEY: misc_feature
<222> LOCATION: (2)..(2)
<223> OTHER INFORMATION: gm

<400> SEQUENCE: 74
tngcgggtga tagggattc                                            20

<210> SEQ ID NO 75
<211> LENGTH: 24
<212> TYPE: DNA
<213> ORGANISM: Artificial Sequence
<220> FEATURE:
<223> OTHER INFORMATION: PCR primer (reverse) for tRNA, GluE2(CGG)
<220> FEATURE:
<221> NAME/KEY: misc_feature
<222> LOCATION: (2)..(2)
<223> OTHER INFORMATION: gm

<400> SEQUENCE: 75
tngcgtcccc tagggattc ttcg                                       24

<210> SEQ ID NO 76
<211> LENGTH: 18
<212> TYPE: DNA
<213> ORGANISM: Artificial Sequence
<220> FEATURE:
<223> OTHER INFORMATION: PCR primer (reverse) for tRNA, AsnE2(CGG)
<220> FEATURE:
<221> NAME/KEY: misc_feature

```
<222> LOCATION: (2)..(2)
<223> OTHER INFORMATION: gm

<400> SEQUENCE: 76
tngcggctct gactggac                                                   18

<210> SEQ ID NO 77
<211> LENGTH: 17
<212> TYPE: DNA
<213> ORGANISM: Artificial Sequence
<220> FEATURE:
<223> OTHER INFORMATION: PCR primer (reverse) for tRNA, fMet(CAU)
<220> FEATURE:
<221> NAME/KEY: misc_feature
<222> LOCATION: (2)..(2)
<223> OTHER INFORMATION: gm

<400> SEQUENCE: 77
tngttgcggg ggccgga                                                    17

<210> SEQ ID NO 78
<211> LENGTH: 63
<212> TYPE: RNA
<213> ORGANISM: Artificial Sequence
<220> FEATURE:
<223> OTHER INFORMATION: mRNA (mR1) for D-amino acid
<220> FEATURE:
<221> NAME/KEY: misc_feature
<222> LOCATION: (28)..(33)
<223> OTHER INFORMATION: n is a, c, g, or u

<400> SEQUENCE: 78
auguacaaga aguacaaaaa guacaaannn nnnggugacu acaaggacga cgacgacaag     60
uaa                                                                   63

<210> SEQ ID NO 79
<211> LENGTH: 63
<212> TYPE: RNA
<213> ORGANISM: Artificial Sequence
<220> FEATURE:
<223> OTHER INFORMATION: mRNA (mR2) for D-amino acid
<220> FEATURE:
<221> NAME/KEY: misc_feature
<222> LOCATION: (28)..(36)
<223> OTHER INFORMATION: n is a, c, g, or u

<400> SEQUENCE: 79
auguacaaga aguacaaaaa guacaaannn nnnnnngacu acaaggacga cgacgacaag     60
uaa                                                                   63

<210> SEQ ID NO 80
<211> LENGTH: 72
<212> TYPE: RNA
<213> ORGANISM: Artificial Sequence
<220> FEATURE:
<223> OTHER INFORMATION: mRNA (mR3) for D-amino acid

<400> SEQUENCE: 80
auguacaaga aguacaaaaa guacaaaauu auuuacuaca uuauugacua caaggacgac     60
gacgacaagu aa                                                         72

<210> SEQ ID NO 81
<211> LENGTH: 72
<212> TYPE: RNA
<213> ORGANISM: Artificial Sequence
<220> FEATURE:
```

<223> OTHER INFORMATION: mRNA (mR4) for D-amino acid

<400> SEQUENCE: 81
auguacaaga aguacaaaaa guacaaaauu auuuacuacc aucaugacua caaggacgac    60
gacgacaagu aa    72

<210> SEQ ID NO 82
<211> LENGTH: 72
<212> TYPE: RNA
<213> ORGANISM: Artificial Sequence
<220> FEATURE:
<223> OTHER INFORMATION: mRNA (mR5) for D-amino acid

<400> SEQUENCE: 82
auguacaaga aguacaaaaa guacaaaauu auuuacuaca cuacugacua caaggacgac    60
gacgacaagu aa    72

<210> SEQ ID NO 83
<211> LENGTH: 75
<212> TYPE: RNA
<213> ORGANISM: Artificial Sequence
<220> FEATURE:
<223> OTHER INFORMATION: mRNA (mR6) for D-amino acid

<400> SEQUENCE: 83
auguacaaga aguacaaaaa guacaaaauu uacacuuaca uuuacacuga cuacaaggac    60
gacgacgaca aguaa    75

<210> SEQ ID NO 84
<211> LENGTH: 69
<212> TYPE: RNA
<213> ORGANISM: Artificial Sequence
<220> FEATURE:
<223> OTHER INFORMATION: mRNA (mR7) for D-amino acid

<400> SEQUENCE: 84
auguacaaga aguacaaaaa guacaaaacu uacauuuacc augacuacaa ggacgacgac    60
gacaaguaa    69

<210> SEQ ID NO 85
<211> LENGTH: 69
<212> TYPE: RNA
<213> ORGANISM: Artificial Sequence
<220> FEATURE:
<223> OTHER INFORMATION: mRNA (mR8) for D-amino acid

<400> SEQUENCE: 85
auguacaaga aguacaaaaa guacaaacau acuauuacuc augacuacaa ggacgacgac    60
gacaaguaa    69

<210> SEQ ID NO 86
<211> LENGTH: 48
<212> TYPE: RNA
<213> ORGANISM: Artificial Sequence
<220> FEATURE:
<223> OTHER INFORMATION: mRNA (mR9) for D-amino acid

<400> SEQUENCE: 86
auggcugcuc auaagaagaa ggacuacaag gacgacgacg acaaguaa    48

<210> SEQ ID NO 87
<211> LENGTH: 63

```
<212> TYPE: RNA
<213> ORGANISM: Artificial Sequence
<220> FEATURE:
<223> OTHER INFORMATION: mRNA (mR1) for beta amino acid

<400> SEQUENCE: 87
auguacaaga aguacaaaaa guacaaaccg ccgggugacu acaaggacga cgacgacaag    60
uaa                                                                  63

<210> SEQ ID NO 88
<211> LENGTH: 63
<212> TYPE: RNA
<213> ORGANISM: Artificial Sequence
<220> FEATURE:
<223> OTHER INFORMATION: mRNA (mR2) for beta amino acid

<400> SEQUENCE: 88
auguacaaga aguacaaaaa guacaaaccg ccgggugacu acaaggacga cgacgacaag    60
uaa                                                                  63

<210> SEQ ID NO 89
<211> LENGTH: 63
<212> TYPE: RNA
<213> ORGANISM: Artificial Sequence
<220> FEATURE:
<223> OTHER INFORMATION: mRNA (mR3-3) for beta amino acid

<400> SEQUENCE: 89
auguacaaga aguacaaaaa guacaaaauu cauauugacu acaaggacga cgacgacaag    60
uaa                                                                  63

<210> SEQ ID NO 90
<211> LENGTH: 66
<212> TYPE: RNA
<213> ORGANISM: Artificial Sequence
<220> FEATURE:
<223> OTHER INFORMATION: mRNA (mR3-4) for beta amino acid

<400> SEQUENCE: 90
auguacaaga aguacaaaaa guacaaaauu cauauucaug acuacaagga cgacgacgac    60
aaguaa                                                               66

<210> SEQ ID NO 91
<211> LENGTH: 69
<212> TYPE: RNA
<213> ORGANISM: Artificial Sequence
<220> FEATURE:
<223> OTHER INFORMATION: mRNA (mR3-5) for beta amino acid

<400> SEQUENCE: 91
auguacaaga aguacaaaaa guacaaaauu cauauucaua uugacuacaa ggacgacgac    60
gacaaguaa                                                            69

<210> SEQ ID NO 92
<211> LENGTH: 72
<212> TYPE: RNA
<213> ORGANISM: Artificial Sequence
<220> FEATURE:
<223> OTHER INFORMATION: mRNA (mR3-6) for beta amino acid

<400> SEQUENCE: 92
auguacaaga aguacaaaaa guacaaaauu cauauucaua uucaugacua caaggacgac    60
```
gacgacaagu aa 72

<210> SEQ ID NO 93
<211> LENGTH: 75
<212> TYPE: RNA
<213> ORGANISM: Artificial Sequence
<220> FEATURE:
<223> OTHER INFORMATION: mRNA (mR3-7) for beta amino acid

<400> SEQUENCE: 93
auguacaaga aguacaaaaa guacaaaauu cauauucaua uucauauuga cuacaaggac    60
gacgacgaca aguaa    75

<210> SEQ ID NO 94
<211> LENGTH: 69
<212> TYPE: RNA
<213> ORGANISM: Artificial Sequence
<220> FEATURE:
<223> OTHER INFORMATION: mRNA (mR4) for beta amino acid

<400> SEQUENCE: 94
auguacaaga aguacaaaaa guacaaacau uacauuuacc augacuacaa ggacgacgac    60
gacaaguaa    69

<210> SEQ ID NO 95
<211> LENGTH: 69
<212> TYPE: RNA
<213> ORGANISM: Artificial Sequence
<220> FEATURE:
<223> OTHER INFORMATION: mRNA (mR5) for beta amino acid

<400> SEQUENCE: 95
auguacaaga aguacaaaaa guacaaaacu uacauuuacc augacuacaa ggacgacgac    60
gacaaguaa    69

<210> SEQ ID NO 96
<211> LENGTH: 72
<212> TYPE: RNA
<213> ORGANISM: Artificial Sequence
<220> FEATURE:
<223> OTHER INFORMATION: mRNA (mR6) for beta amino acid

<400> SEQUENCE: 96
auguacaaga aguacaaaaa guacaaaauu auuuacuacc aucaugacua caaggacgac    60
gacgacaagu aa    72

<210> SEQ ID NO 97
<211> LENGTH: 72
<212> TYPE: RNA
<213> ORGANISM: Artificial Sequence
<220> FEATURE:
<223> OTHER INFORMATION: mRNA (mR7) for beta amino acid

<400> SEQUENCE: 97
auguacaaga aguacaaaaa guacaaaauu cauuacuaca uucaugacua caaggacgac    60
gacgacaagu aa    72

<210> SEQ ID NO 98
<211> LENGTH: 72
<212> TYPE: RNA
<213> ORGANISM: Artificial Sequence
<220> FEATURE:
<223> OTHER INFORMATION: mRNA (mR8) for beta amino acid -continued

<400> SEQUENCE: 98
auguacaaga aguacaaaaa guacaaaauu auuuacuacc aucaugacua caaggacgac    60
gacgacaagu aa    72

<210> SEQ ID NO 99
<211> LENGTH: 69
<212> TYPE: RNA
<213> ORGANISM: Artificial Sequence
<220> FEATURE:
<223> OTHER INFORMATION: mRNA (mR9) for beta amino acid

<400> SEQUENCE: 99
auguacaaga aguacaaaaa guacaaacau acuauuacuc augacuacaa ggacgacgac    60
gacaaguaa    69

<210> SEQ ID NO 100
<211> LENGTH: 48
<212> TYPE: RNA
<213> ORGANISM: Artificial Sequence
<220> FEATURE:
<223> OTHER INFORMATION: mRNA (mR10) for beta amino acid

<400> SEQUENCE: 100
augacuacuc auaagaagaa ggacuacaag gacgacgacg acaaguaa    48

<210> SEQ ID NO 101
<211> LENGTH: 51
<212> TYPE: RNA
<213> ORGANISM: Artificial Sequence
<220> FEATURE:
<223> OTHER INFORMATION: mRNA (mR11) for beta amino acid

<400> SEQUENCE: 101
augacuacua cucauaagaa gaaggacuac aaggacgacg acgacaagua a    51

<210> SEQ ID NO 102
<211> LENGTH: 20
<212> TYPE: PRT
<213> ORGANISM: Artificial Sequence
<220> FEATURE:
<223> OTHER INFORMATION: reprogrammed peptide (rP1) for beta amino acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(11)
<223> OTHER INFORMATION: L-beta-homoglutamine, L-beta-homomethionine or
      L-beta-homophenylglycine

<400> SEQUENCE: 102

Met Tyr Lys Lys Tyr Lys Lys Tyr Lys Xaa Xaa Gly Asp Tyr Lys Asp
1               5                   10                  15

Asp Asp Asp Lys
            20

<210> SEQ ID NO 103
<211> LENGTH: 20
<212> TYPE: PRT
<213> ORGANISM: Artificial Sequence
<220> FEATURE:
<223> OTHER INFORMATION: reprogrammed peptide (rP2) for beta amino acid
<220> FEATURE:
<221> NAME/KEY: MISC_FEATURE
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(11)
<223> OTHER INFORMATION: L-beta-homoglutamine, L-beta-homomethionine or
      L-beta-homophenylglycine

<400> SEQUENCE: 103

Met Tyr Lys Lys Tyr Lys Lys Tyr Lys Xaa Xaa Gly Asp Tyr Lys Asp
1               5                   10                  15

Asp Asp Asp Lys
            20

<210> SEQ ID NO 104
<211> LENGTH: 20
<212> TYPE: PRT
<213> ORGANISM: Artificial Sequence
<220> FEATURE:
<223> OTHER INFORMATION: reprogrammed peptide (rP3-3) for beta amino
      acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: L-beta-homomethionine
<220> FEATURE:
<221> NAME/KEY: MISC_FEATURE
<222> LOCATION: (11)..(11)
<223> OTHER INFORMATION: L-beta-homophenylglycine
<220> FEATURE:
<221> NAME/KEY: MISC_FEATURE
<222> LOCATION: (12)..(12)
<223> OTHER INFORMATION: L-beta-homomethionine

<400> SEQUENCE: 104

Met Tyr Lys Lys Tyr Lys Lys Tyr Lys Xaa Xaa Xaa Asp Tyr Lys Asp
1               5                   10                  15

Asp Asp Asp Lys
            20

<210> SEQ ID NO 105
<211> LENGTH: 21
<212> TYPE: PRT
<213> ORGANISM: Artificial Sequence
<220> FEATURE:
<223> OTHER INFORMATION: reprogrammed peptide (rP3-4) for beta amino
      acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: L-beta-homomethionine
<220> FEATURE:
<221> NAME/KEY: MISC_FEATURE
<222> LOCATION: (11)..(11)
<223> OTHER INFORMATION: L-beta-homophenylglycine
<220> FEATURE:
<221> NAME/KEY: MISC_FEATURE
<222> LOCATION: (12)..(12)
<223> OTHER INFORMATION: L-beta-homomethionine
<220> FEATURE:
<221> NAME/KEY: MISC_FEATURE
<222> LOCATION: (13)..(13)
<223> OTHER INFORMATION: L-beta-homophenylglycine

<400> SEQUENCE: 105

```
Met Tyr Lys Lys Tyr Lys Lys Tyr Lys Xaa Xaa Xaa Xaa Asp Tyr Lys
1               5                   10                  15

Asp Asp Asp Asp Lys
            20

<210> SEQ ID NO 106
<211> LENGTH: 22
<212> TYPE: PRT
<213> ORGANISM: Artificial Sequence
<220> FEATURE:
<223> OTHER INFORMATION: reprogrammed peptide (rP3-5) for beta amino
      acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: L-beta-homomethionine
<220> FEATURE:
<221> NAME/KEY: MISC_FEATURE
<222> LOCATION: (11)..(11)
<223> OTHER INFORMATION: L-beta-homophenylglycine
<220> FEATURE:
<221> NAME/KEY: MISC_FEATURE
<222> LOCATION: (12)..(12)
<223> OTHER INFORMATION: L-beta-homomethionine
<220> FEATURE:
<221> NAME/KEY: MISC_FEATURE
<222> LOCATION: (13)..(13)
<223> OTHER INFORMATION: L-beta-homophenylglycine
<220> FEATURE:
<221> NAME/KEY: MISC_FEATURE
<222> LOCATION: (14)..(14)
<223> OTHER INFORMATION: L-beta-homomethionine

<400> SEQUENCE: 106

Met Tyr Lys Lys Tyr Lys Lys Tyr Lys Xaa Xaa Xaa Xaa Xaa Asp Tyr
1               5                   10                  15

Lys Asp Asp Asp Asp Lys
            20

<210> SEQ ID NO 107
<211> LENGTH: 23
<212> TYPE: PRT
<213> ORGANISM: Artificial Sequence
<220> FEATURE:
<223> OTHER INFORMATION: reprogrammed peptide (rP3-6) for beta amino
      acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: L-beta-homomethionine
<220> FEATURE:
<221> NAME/KEY: MISC_FEATURE
<222> LOCATION: (11)..(11)
<223> OTHER INFORMATION: L-beta-homophenylglycine
<220> FEATURE:
<221> NAME/KEY: MISC_FEATURE
<222> LOCATION: (12)..(12)
<223> OTHER INFORMATION: L-beta-homomethionine
<220> FEATURE:
<221> NAME/KEY: MISC_FEATURE
<222> LOCATION: (13)..(13)
<223> OTHER INFORMATION: L-beta-homophenylglycine
<220> FEATURE:
<221> NAME/KEY: MISC_FEATURE
<222> LOCATION: (14)..(14)
```

```
<223> OTHER INFORMATION: L-beta-homomethionine
<220> FEATURE:
<221> NAME/KEY: MISC_FEATURE
<222> LOCATION: (15)..(15)
<223> OTHER INFORMATION: L-beta-homophenylglycine

<400> SEQUENCE: 107

Met Tyr Lys Lys Tyr Lys Tyr Lys Xaa Xaa Xaa Xaa Xaa Xaa Asp
1               5                   10                  15

Tyr Lys Asp Asp Asp Asp Lys
            20

<210> SEQ ID NO 108
<211> LENGTH: 24
<212> TYPE: PRT
<213> ORGANISM: Artificial Sequence
<220> FEATURE:
<223> OTHER INFORMATION: reprogrammed peptide (rP3-7) for beta amino
      acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: L-beta-homomethionine
<220> FEATURE:
<221> NAME/KEY: MISC_FEATURE
<222> LOCATION: (11)..(11)
<223> OTHER INFORMATION: L-beta-homophenylglycine
<220> FEATURE:
<221> NAME/KEY: MISC_FEATURE
<222> LOCATION: (12)..(12)
<223> OTHER INFORMATION: L-beta-homomethionine
<220> FEATURE:
<221> NAME/KEY: MISC_FEATURE
<222> LOCATION: (13)..(13)
<223> OTHER INFORMATION: L-beta-homophenylglycine
<220> FEATURE:
<221> NAME/KEY: MISC_FEATURE
<222> LOCATION: (14)..(14)
<223> OTHER INFORMATION: L-beta-homomethionine
<220> FEATURE:
<221> NAME/KEY: MISC_FEATURE
<222> LOCATION: (15)..(15)
<223> OTHER INFORMATION: L-beta-homophenylglycine
<220> FEATURE:
<221> NAME/KEY: MISC_FEATURE
<222> LOCATION: (16)..(16)
<223> OTHER INFORMATION: L-beta-homomethionine

<400> SEQUENCE: 108

Met Tyr Lys Lys Tyr Lys Tyr Lys Xaa Xaa Xaa Xaa Xaa Xaa Xaa
1               5                   10                  15

Asp Tyr Lys Asp Asp Asp Asp Lys
            20

<210> SEQ ID NO 109
<211> LENGTH: 22
<212> TYPE: PRT
<213> ORGANISM: Artificial Sequence
<220> FEATURE:
<223> OTHER INFORMATION: reprogrammed peptide (rP4) for beta amino acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: L-beta-homophenylglycine
<220> FEATURE:
```

<221> NAME/KEY: MISC_FEATURE
<222> LOCATION: (12)..(12)
<223> OTHER INFORMATION: L-beta-homomethionine
<220> FEATURE:
<221> NAME/KEY: MISC_FEATURE
<222> LOCATION: (14)..(14)
<223> OTHER INFORMATION: L-beta-homophenylglycine

<400> SEQUENCE: 109

Met Tyr Lys Lys Tyr Lys Lys Tyr Lys Xaa Tyr Xaa Tyr Xaa Asp Tyr
1               5                   10                  15

Lys Asp Asp Asp Asp Lys
            20

<210> SEQ ID NO 110
<211> LENGTH: 22
<212> TYPE: PRT
<213> ORGANISM: Artificial Sequence
<220> FEATURE:
<223> OTHER INFORMATION: reprogrammed peptide (rP5) for beta amino acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: L-beta-homoglutamine
<220> FEATURE:
<221> NAME/KEY: MISC_FEATURE
<222> LOCATION: (12)..(12)
<223> OTHER INFORMATION: L-beta-homomethionine
<220> FEATURE:
<221> NAME/KEY: MISC_FEATURE
<222> LOCATION: (14)..(14)
<223> OTHER INFORMATION: L-beta-homophenylglycine

<400> SEQUENCE: 110

Met Tyr Lys Lys Tyr Lys Lys Tyr Lys Xaa Tyr Xaa Tyr Xaa Asp Tyr
1               5                   10                  15

Lys Asp Asp Asp Asp Lys
            20

<210> SEQ ID NO 111
<211> LENGTH: 23
<212> TYPE: PRT
<213> ORGANISM: Artificial Sequence
<220> FEATURE:
<223> OTHER INFORMATION: reprogrammed peptide (rP6) for beta amino acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: L-beta-homomethionine
<220> FEATURE:
<221> NAME/KEY: MISC_FEATURE
<222> LOCATION: (11)..(11)
<223> OTHER INFORMATION: L-beta-homomethionine
<220> FEATURE:
<221> NAME/KEY: MISC_FEATURE
<222> LOCATION: (14)..(14)
<223> OTHER INFORMATION: L-beta-homophenylglycine
<220> FEATURE:
<221> NAME/KEY: MISC_FEATURE
<222> LOCATION: (15)..(15)
<223> OTHER INFORMATION: L-beta-homophenylglycine

<400> SEQUENCE: 111

Met Tyr Lys Lys Tyr Lys Lys Tyr Lys Xaa Xaa Tyr Tyr Xaa Xaa Asp

Tyr Lys Asp Asp Asp Asp Lys
            20

<210> SEQ ID NO 112
<211> LENGTH: 23
<212> TYPE: PRT
<213> ORGANISM: Artificial Sequence
<220> FEATURE:
<223> OTHER INFORMATION: reprogrammed peptide (rP7) for beta amino acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: L-beta-homomethionine
<220> FEATURE:
<221> NAME/KEY: MISC_FEATURE
<222> LOCATION: (11)..(11)
<223> OTHER INFORMATION: L-beta-homophenylglycine
<220> FEATURE:
<221> NAME/KEY: MISC_FEATURE
<222> LOCATION: (14)..(14)
<223> OTHER INFORMATION: L-beta-homophenylglycine
<220> FEATURE:
<221> NAME/KEY: MISC_FEATURE
<222> LOCATION: (15)..(15)
<223> OTHER INFORMATION: L-beta-homophenylglycine

<400> SEQUENCE: 112

Met Tyr Lys Lys Tyr Lys Lys Tyr Lys Xaa Xaa Tyr Tyr Xaa Xaa Asp
1               5                   10                  15

Tyr Lys Asp Asp Asp Asp Lys
            20

<210> SEQ ID NO 113
<211> LENGTH: 8
<212> TYPE: PRT
<213> ORGANISM: Artificial Sequence
<220> FEATURE:
<223> OTHER INFORMATION: flag

<400> SEQUENCE: 113

Asp Tyr Lys Asp Asp Asp Asp Lys
1               5

<210> SEQ ID NO 114
<211> LENGTH: 6
<212> TYPE: PRT
<213> ORGANISM: Artificial Sequence
<220> FEATURE:
<223> OTHER INFORMATION: partial structure of rP3 peptide
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (5)..(6)
<223> OTHER INFORMATION: D-Ala

<400> SEQUENCE: 114

Ala Ala Tyr Tyr Ala Ala
1               5

<210> SEQ ID NO 115
<211> LENGTH: 6
<212> TYPE: PRT

```
<213> ORGANISM: Artificial Sequence
<220> FEATURE:
<223> OTHER INFORMATION: partial structure of rP4 peptide
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (5)..(6)
<223> OTHER INFORMATION: D-Cys

<400> SEQUENCE: 115

Ala Ala Tyr Tyr Cys Cys
1               5

<210> SEQ ID NO 116
<211> LENGTH: 6
<212> TYPE: PRT
<213> ORGANISM: Artificial Sequence
<220> FEATURE:
<223> OTHER INFORMATION: partial structure of rP5 peptide
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (5)..(6)
<223> OTHER INFORMATION: D-Ser

<400> SEQUENCE: 116

Ala Ala Tyr Tyr Ser Ser
1               5

<210> SEQ ID NO 117
<211> LENGTH: 5
<212> TYPE: PRT
<213> ORGANISM: Artificial Sequence
<220> FEATURE:
<223> OTHER INFORMATION: partial structure of rP8 peptide
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (4)..(4)
<223> OTHER INFORMATION: D-Ser
<220> FEATURE:
<221> NAME/KEY: MOD_RES
<222> LOCATION: (5)..(5)
<223> OTHER INFORMATION: D-Cys

<400> SEQUENCE: 117

Cys Ser Ala Ser Cys
1               5

<210> SEQ ID NO 118
<211> LENGTH: 4
<212> TYPE: PRT
<213> ORGANISM: Artificial Sequence
<220> FEATURE:
<223> OTHER INFORMATION: partial structure of rP9 peptide
<220> FEATURE:
```

```
<221> NAME/KEY: MOD_RES
<222> LOCATION: (1)..(1)
<223> OTHER INFORMATION: N-chloroacetyl-D-phenylalanine
<220> FEATURE:
<221> NAME/KEY: MOD_RES
<222> LOCATION: (2)..(3)
<223> OTHER INFORMATION: D-Ser
<220> FEATURE:
<221> NAME/KEY: MOD_RES
<222> LOCATION: (4)..(4)
<223> OTHER INFORMATION: D-Cys

<400> SEQUENCE: 118

Phe Ser Ser Cys
1

<210> SEQ ID NO 119
<211> LENGTH: 8
<212> TYPE: PRT
<213> ORGANISM: Artificial Sequence
<220> FEATURE:
<223> OTHER INFORMATION: partial structure of reprogrammed peptide rP1

<400> SEQUENCE: 119

Tyr Lys Lys Tyr Lys Lys Tyr Lys
1               5

<210> SEQ ID NO 120
<211> LENGTH: 12
<212> TYPE: PRT
<213> ORGANISM: Artificial Sequence
<220> FEATURE:
<223> OTHER INFORMATION: partial structure of rP1-X2 peptide
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MOD_RES
<222> LOCATION: (10)..(11)
<223> OTHER INFORMATION: consecutive D-Ala, consecutive L-Pro,
      consecutive D-Ser, consecutive D-His, consecutive Aib

<400> SEQUENCE: 120

Met Tyr Lys Lys Tyr Lys Lys Tyr Lys Xaa Xaa Gly
1               5                   10

<210> SEQ ID NO 121
<211> LENGTH: 12
<212> TYPE: PRT
<213> ORGANISM: Artificial Sequence
<220> FEATURE:
<223> OTHER INFORMATION: partial structure of rP2-X3 peptide
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MOD_RES
<222> LOCATION: (10)..(12)
<223> OTHER INFORMATION: consecutive D-Ala, consecutive L-Pro,
      consecutive Aib

<400> SEQUENCE: 121

Met Tyr Lys Lys Tyr Lys Lys Tyr Lys Xaa Xaa Xaa
1               5                   10

<210> SEQ ID NO 122
<211> LENGTH: 15
<212> TYPE: PRT
<213> ORGANISM: Artificial Sequence
```

```
<220> FEATURE:
<223> OTHER INFORMATION: partial structure of peptide (rP3) for D-amino
      acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MOD_RES
<222> LOCATION: (10)..(11)
<223> OTHER INFORMATION: D-Ala
<220> FEATURE:
<221> NAME/KEY: MOD_RES
<222> LOCATION: (14)..(15)
<223> OTHER INFORMATION: D-Ala

<400> SEQUENCE: 122

Met Tyr Lys Lys Tyr Lys Lys Tyr Lys Ala Ala Tyr Tyr Ala Ala
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: partial structure of peptide (rP4) for D-amino
      acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MOD_RES
<222> LOCATION: (10)..(11)
<223> OTHER INFORMATION: D-Ala
<220> FEATURE:
<221> NAME/KEY: MOD_RES
<222> LOCATION: (14)..(15)
<223> OTHER INFORMATION: D-Cys

<400> SEQUENCE: 123

Met Tyr Lys Lys Tyr Lys Lys Tyr Lys Ala Ala Tyr Tyr Cys Cys
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: partial structure of peptide (rP5) for D-amino
      acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MOD_RES
<222> LOCATION: (10)..(11)
<223> OTHER INFORMATION: D-Ala
<220> FEATURE:
<221> NAME/KEY: MOD_RES
<222> LOCATION: (14)..(15)
<223> OTHER INFORMATION: D-Ser

<400> SEQUENCE: 124

Met Tyr Lys Lys Tyr Lys Lys Tyr Lys Ala Ala Tyr Tyr Ser Ser
1               5                   10                  15

<210> SEQ ID NO 125
<211> LENGTH: 16
<212> TYPE: PRT
<213> ORGANISM: Artificial Sequence
<220> FEATURE:
```

```
<223> OTHER INFORMATION: partial structure of peptide (rP6) for D-amino
      acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MOD_RES
<222> LOCATION: (10)..(10)
<223> OTHER INFORMATION: D-Ala
<220> FEATURE:
<221> NAME/KEY: MOD_RES
<222> LOCATION: (12)..(12)
<223> OTHER INFORMATION: D-Ser
<220> FEATURE:
<221> NAME/KEY: MOD_RES
<222> LOCATION: (14)..(14)
<223> OTHER INFORMATION: D-Ala
<220> FEATURE:
<221> NAME/KEY: MOD_RES
<222> LOCATION: (16)..(16)
<223> OTHER INFORMATION: D-Ser

<400> SEQUENCE: 125

Met Tyr Lys Lys Tyr Lys Lys Tyr Lys Ala Tyr Ser Tyr Ala Tyr Ser
1               5                   10                  15

<210> SEQ ID NO 126
<211> LENGTH: 14
<212> TYPE: PRT
<213> ORGANISM: Artificial Sequence
<220> FEATURE:
<223> OTHER INFORMATION: partial structure of peptide (rP7) for D-amino
      acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MOD_RES
<222> LOCATION: (10)..(10)
<223> OTHER INFORMATION: D-Ser
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (14)..(14)
<223> OTHER INFORMATION: D-Cys

<400> SEQUENCE: 126

Met Tyr Lys Lys Tyr Lys Lys Tyr Lys Ser Tyr Ala Tyr Cys
1               5                   10

<210> SEQ ID NO 127
<211> LENGTH: 14
<212> TYPE: PRT
<213> ORGANISM: Artificial Sequence
<220> FEATURE:
<223> OTHER INFORMATION: partial structure of peptide (rP8) for D-amino
      acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MOD_RES
<222> LOCATION: (10)..(10)
<223> OTHER INFORMATION: D-Cys
<220> FEATURE:
<221> NAME/KEY: MOD_RES
<222> LOCATION: (11)..(11)
<223> OTHER INFORMATION: D-Ser
<220> FEATURE:
```

```
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Ser
<220> FEATURE:
<221> NAME/KEY: MOD_RES
<222> LOCATION: (14)..(14)
<223> OTHER INFORMATION: D-Cys

<400> SEQUENCE: 127

Met Tyr Lys Lys Tyr Lys Lys Tyr Lys Cys Ser Ala Ser Cys
1               5                   10

<210> SEQ ID NO 128
<211> LENGTH: 7
<212> TYPE: PRT
<213> ORGANISM: Artificial Sequence
<220> FEATURE:
<223> OTHER INFORMATION: partial structure of peptide (rP9) for D-amino
      acid
<220> FEATURE:
<221> NAME/KEY: MOD_RES
<222> LOCATION: (1)..(1)
<223> OTHER INFORMATION: N-chloroacetyl-D-phenylalanine
<220> FEATURE:
<221> NAME/KEY: MOD_RES
<222> LOCATION: (2)..(3)
<223> OTHER INFORMATION: D-Ser
<220> FEATURE:
<221> NAME/KEY: MOD_RES
<222> LOCATION: (4)..(4)
<223> OTHER INFORMATION: D-Cys

<400> SEQUENCE: 128

Phe Ser Ser Cys Lys Lys Lys
1               5

<210> SEQ ID NO 129
<211> LENGTH: 15
<212> TYPE: PRT
<213> ORGANISM: Artificial Sequence
<220> FEATURE:
<223> OTHER INFORMATION: partial structure of reprogrammed peptide (rP8)
      for D-amino acid and beta amino acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(11)
<223> OTHER INFORMATION: L-beta-homomethionine
<220> FEATURE:
<221> NAME/KEY: MOD_RES
<222> LOCATION: (14)..(15)
<223> OTHER INFORMATION: D-Ala

<400> SEQUENCE: 129

Met Tyr Lys Lys Tyr Lys Lys Tyr Lys Xaa Xaa Tyr Tyr Ala Ala
1               5                   10                  15

<210> SEQ ID NO 130
<211> LENGTH: 14
<212> TYPE: PRT
<213> ORGANISM: Artificial Sequence
<220> FEATURE:
<223> OTHER INFORMATION: partial structure of reprogrammed peptide (rP9)
      for D-amino acid and beta amino acid
<220> FEATURE:
<221> NAME/KEY: MISC_FEATURE
```

```
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: L-beta-homophenylglycine
<220> FEATURE:
<221> NAME/KEY: MOD_RES
<222> LOCATION: (11)..(11)
<223> OTHER INFORMATION: D-Ser
<220> FEATURE:
<221> NAME/KEY: MISC_FEATURE
<222> LOCATION: (12)..(12)
<223> OTHER INFORMATION: L-beta-homomethionine
<220> FEATURE:
<221> NAME/KEY: MOD_RES
<222> LOCATION: (13)..(13)
<223> OTHER INFORMATION: D-Ser
<220> FEATURE:
<221> NAME/KEY: MISC_FEATURE
<222> LOCATION: (14)..(14)
<223> OTHER INFORMATION: L-beta-homophenylglycine

<400> SEQUENCE: 130

Met Tyr Lys Lys Tyr Lys Lys Tyr Lys Xaa Ser Xaa Ser Phe
1               5                   10

<210> SEQ ID NO 131
<211> LENGTH: 7
<212> TYPE: PRT
<213> ORGANISM: Artificial Sequence
<220> FEATURE:
<223> OTHER INFORMATION: partial structure of reprogrammed peptide
      (rP10) for D-amino acid and beta amino acid
<220> FEATURE:
<221> NAME/KEY: MOD_RES
<222> LOCATION: (1)..(1)
<223> OTHER INFORMATION: N-chloroacetyl-D-phenylalanine
<220> FEATURE:
<221> NAME/KEY: MISC_FEATURE
<222> LOCATION: (2)..(3)
<223> OTHER INFORMATION: L-beta-homomethionine
<220> FEATURE:
<221> NAME/KEY: MOD_RES
<222> LOCATION: (4)..(4)
<223> OTHER INFORMATION: D-Cys

<400> SEQUENCE: 131

Phe Xaa Xaa Cys Lys Lys Lys
1               5

<210> SEQ ID NO 132
<211> LENGTH: 8
<212> TYPE: PRT
<213> ORGANISM: Artificial Sequence
<220> FEATURE:
<223> OTHER INFORMATION: partial structure of reprogrammed peptide
      (rP11) for D-amino acid and beta amino acid
<220> FEATURE:
<221> NAME/KEY: MOD_RES
<222> LOCATION: (1)..(1)
<223> OTHER INFORMATION: N-chloroacetyl-D-phenylalanine
<220> FEATURE:
<221> NAME/KEY: MISC_FEATURE
<222> LOCATION: (2)..(4)
```

```
<223> OTHER INFORMATION: L-beta-homomethionine
<220> FEATURE:
<221> NAME/KEY: MOD_RES
<222> LOCATION: (5)..(5)
<223> OTHER INFORMATION: D-Cys

<400> SEQUENCE: 132

Phe Xaa Xaa Xaa Cys Lys Lys Lys
1               5
```